United States Patent
Weiner et al.

(10) Patent No.: US 11,021,520 B2
(45) Date of Patent: Jun. 1, 2021

(54) HUMAN RESPIRATORY SYNCYTIAL VIRUS CONSENSUS ANTIGENS, NUCLEIC ACID CONSTRUCTS AND VACCINES MADE THEREFROM, AND METHODS OF USING THE SAME

(71) Applicant: The Trustees of the University of Pennsylvania, Philadelphia, PA (US)

(72) Inventors: David B. Weiner, Merion, PA (US); Daniel Choo, Lansdale, PA (US); Kar Muthumani, Cherry Hill, NJ (US); Nyamekye Obeng-Adjei, Lansdowne, PA (US); Veronica Scott, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 75 days.

(21) Appl. No.: 16/055,425

(22) Filed: Aug. 6, 2018

(65) Prior Publication Data
US 2018/0346522 A1  Dec. 6, 2018

Related U.S. Application Data

(62) Division of application No. 14/391,921, filed as application No. PCT/US2013/036008 on Apr. 10, 2013, now Pat. No. 10,040,828.

(60) Provisional application No. 61/622,279, filed on Apr. 10, 2012.

(51) Int. Cl.
| | |
|---|---|
| C07K 14/005 | (2006.01) |
| A61K 39/12 | (2006.01) |
| A61K 39/155 | (2006.01) |
| A61K 39/39 | (2006.01) |
| A61K 39/00 | (2006.01) |

(52) U.S. Cl.
CPC ............ *C07K 14/005* (2013.01); *A61K 39/12* (2013.01); *A61K 39/155* (2013.01); *A61K 39/39* (2013.01); *A61K 2039/53* (2013.01); *A61K 2039/55522* (2013.01); *A61K 2039/57* (2013.01); *A61K 2039/70* (2013.01); *C12N 2760/18522* (2013.01); *C12N 2760/18534* (2013.01)

(58) Field of Classification Search
None
See application file for complete search history.

(56) References Cited

U.S. PATENT DOCUMENTS

| | | | |
|---|---|---|---|
| 7,041,294 B2 | 5/2006 | Staats | |
| 8,133,723 B2 | 3/2012 | Draghia-Akli | |
| 8,398,993 B2 | 3/2013 | Kalergis Parra | |
| 8,829,174 B2 | 9/2014 | Weiner | |
| 9,156,890 B2 | 10/2015 | Weiner | |
| 9,168,294 B2 | 10/2015 | Morrison | |
| 2004/0096451 A1 | 5/2004 | Young | |
| 2010/0203071 A1 | 8/2010 | Blais | |
| 2011/0014220 A1 | 1/2011 | Chow | |
| 2011/0182938 A1 | 7/2011 | Weiner | |
| 2012/0276142 A1 | 11/2012 | Weiner | |

FOREIGN PATENT DOCUMENTS

| | | |
|---|---|---|
| JP | 2002212099 | 7/2002 |
| WO | 2000020028 | 4/2000 |
| WO | 2008114149 A2 | 9/2008 |
| WO | 2008133663 A2 | 11/2008 |
| WO | 2009042794 A2 | 4/2009 |
| WO | 2010085697 A1 | 7/2010 |
| WO | 2011008974 A2 | 1/2011 |
| WO | 2012006378 | 1/2012 |
| WO | 2012021558 | 2/2012 |
| WO | 2013116965 A1 | 8/2013 |

OTHER PUBLICATIONS

Weisshaar et al. DNA and Cell Biology 2015, vol. 34, pp. 505-510 (Year: 2015).*
Murphy et al. Virus Research 1994 vol. 32, pp. 13-26 (Year: 1994).*
M Connors, P L Collins, C Y Firestone, B R Murphy Journal of Virology Mar. 1991, 65 (3) 1634-1637 (Year: 1991).*
Tang et al. J Infect Dis. Sep. 1995;172(3):734-8 (Year: 1995).*
Widjojoatmodjo, M. N. et al., Virology Journal, 2010, vol. 7, article 114, pp. 1-10.
GenBank Accession No. ACY68435 Jul. 13, 2010, pp. 1-2.
Kumaria, R. et al., "Whole genome characterization of non-tissue culture adapted HRSV strains in severely infected children", Virology Journal, 2011, 8:372, pp. 1-13.
Abdulhaqq et al., "DNA vaccines: developing new strategies to enhance immune responses," Immunol Res, 2008, 42:219-232.

(Continued)

*Primary Examiner* — Shanon A. Foley
*Assistant Examiner* — Myron G Hill
(74) *Attorney, Agent, or Firm* — Riverside Law LLP

(57) ABSTRACT

Nucleic acid molecules and compositions comprising one or more nucleic acid sequences that encode an RSV immunogen are disclosed. Nucleic acids are disclosed that comprise the sequences that encodes consensus RSV F protein or immuno-genic fragment thereof, sequences that encodes an RSV G(A) protein or immunogenic fragment thereof and sequences that encodes an RSV G(B) protein or immunogenic fragment thereof. Compositions comprising one, combinations of two or all three sequences are disclosed. The coding sequences optionally include operable linked coding sequence that encode a signal peptide. Nucleic acid molecules and compositions comprising the chemokine CC20 and/or a consensus RSV M2-1 protein or immunogenic fragment thereof are also disclosed. Immunomodulatory methods and methods of inducing an immune response against RSV are disclosed. Methods of preventing RSV infection and methods of treating individuals infected with RSV are disclosed.

20 Claims, 48 Drawing Sheets
Specification includes a Sequence Listing.

(56) References Cited

OTHER PUBLICATIONS

Wu H et al, "RSV fusion (F) protein DNA vaccine provides partial protection against viral infection", Virus Research, Amsterdam, NL, vol. 145, No. 1, doi:10.1016/J.VIRUSRES.2009.06.012, ISSN 0168-1702, (Oct. 1, 2009), pp. 39-47, (Jun. 21, 2009), XP026564433.
Venter et al., Journal of Virologyvol. 85, No. 16, 2011, pp. 8453-8457.
Yan et al., Molecular Therapyvol. 15, No. 1, 2007, pp. 411-421.
Rolland et al., Journal of Virologyvol. 81(16), 2007, pp. 8507-8514.
Weisshaar et al. DNA and Cell Biology 2015, vol. 34, pp. 505-510.
Murphy et al., Virus Research 1994 vol. 32, pp. 13-26.
Sequence 12, U.S. Appl. No. 14/075,943 comparison dated Nov. 12, 2016.
Guo et al., "Fusion of antigen to chemokine CCL20 or CXCL13 strategy to enhance DNA vaccine potency," 2009, Int Immunopharmacol 9(7-8):925-30.
Ternette et al., 2007, Vaccine, vol. 25, No. 4, pp. 7271-7279.
Lee et al., 2007, Journal of Virology, vol. 81, No. 5, pp. 2349-2358.

\* cited by examiner

Figure 1

Phylogenetic Tree of RSV-F Protein

Phylogenetic Tree of RSV-M2 Protein

Env-Pseudotyped viruses in TZM-BL Cells/ "OFF"

Figure 12

RSV-Fusion Pseudo viral production in 293T cells

1) Collect the cell free supernatant.
2) HIV-1 p24$^{Gag}$ concentration by ELISA for viral quantification Target cell infection 36-48 hrs post transfection Co transfection
- pSG3Δ Env
- RSV- F Immunization Schedule for RSV-F Neutralization Study

Figure 14

Quantification of RSV-F mediated infection in different target cells

Quantification of RSV-F neutralization activity in TZM-bl HeLa cells

Quantification of cell death activity by RSV-F pseudo virus in HeLa cells

Figure 18

Comparison of IFN-g production at different dosages of RSV-M2 vaccine 1 week after last immunization Immunization Schedule for RSV-F + CCL20 Study Comparison of IgG subtypes (IgG1 vs IgG2a) in Sera

Figure 22B

RSV-G (A)
945 bp pCMV
BGH pA
pUC ori
Kan pRSV-G (subtype A)
3944 bp

Figure 22C

RSV-G (B)
930 bp pCMV
BGH pA
pUC ori
Kan pRSV-G (subtype B)
3929 bp

Immunization Schedule for RSV-F Dosage Study

Figure 30

Immunization Schedule for RSV-G(A) and RSV-(B) Dosage Study

Total IgG in Sera after RSV-G(A) DNA immunization

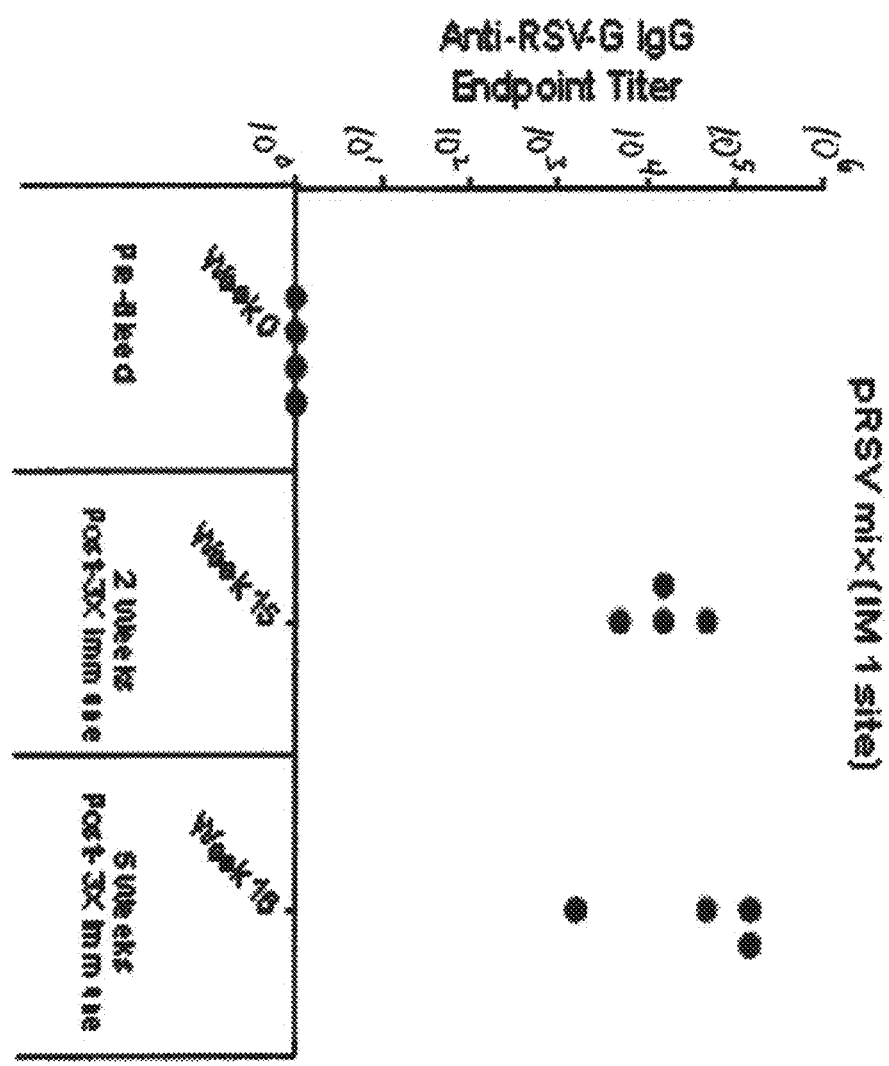

Figure 39C

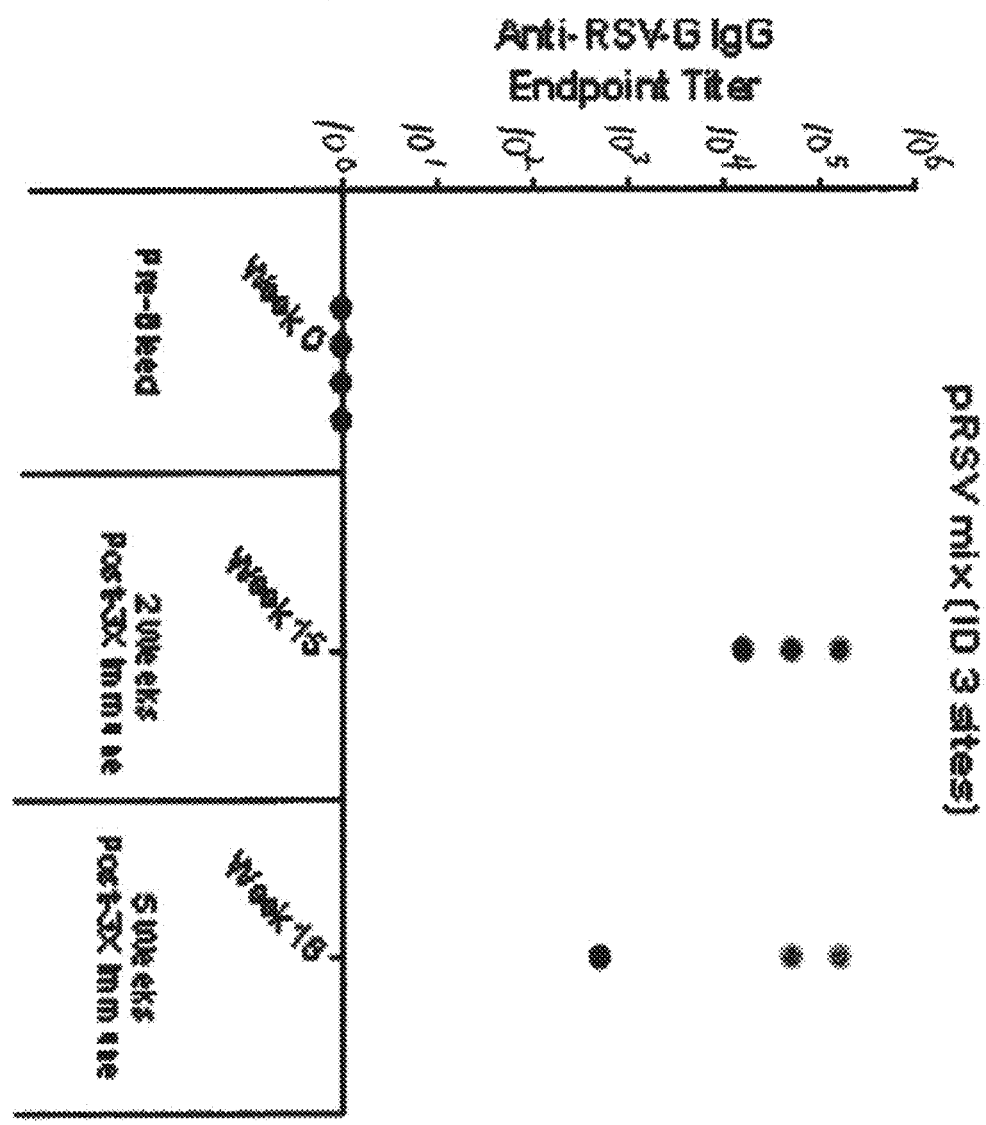

Preliminary Neutralization Results from Cocktail Vaccine in Rabbit and Non-Human Primate Studies

HUMAN RESPIRATORY SYNCYTIAL VIRUS CONSENSUS ANTIGENS, NUCLEIC ACID CONSTRUCTS AND VACCINES MADE THEREFROM, AND METHODS OF USING THE SAME

CROSS-REFERENCE TO RELATED APPLICATIONS

This application is a divisional of U.S. patent application Ser. No. 14/391,921, filed Oct. 10, 2014, which is a U.S. national phase application filed under 35 U.S.C. § 371 claiming benefit to International Patent Application No. PCT/US2013/036008, filed on Apr. 10, 2013, which is entitled to priority under 35 U.S.C. § 119(e) to U.S. provisional application No. 61/622,279, filed Apr. 10, 2012, each of which is incorporated herein by reference in its entirety.

FIELD OF THE INVENTION

The present invention relates to consensus antigenic respiratory syncytia virus proteins and nucleic acid molecules which encode the same; improved respiratory syncytia virus vaccines including such proteins and/or nucleic acid molecules; and methods for using the vaccines for inducing immune responses and preventing respiratory syncytia virus infection and/or treating individuals infected with respiratory syncytia virus.

BACKGROUND OF THE INVENTION

This application claims priority to U.S. Provisional Application No. 61/622,279, which is incorporated herein, in its entirety, by reference.

Human Respiratory Syncytial Virus (RSV) is the most common cause of upper and lower respiratory tract infections among infants and young children (premature infants especially prone to disease). World-wide, RSV is the leading cause of serious lower respiratory infections in infants (especially among those born prematurely and having chronic lung diseases or congenital heart diseases) and young children worldwide, and is responsible for a variety of illnesses, including 20-25% of pneumonia cases and 45-50% of bronchiolitis cases among hospitalized children. In the U.S., RSV invention results in approximately 120,000 hospitalization and 500+ deaths each year. In the population of <1 year old, RSV is the leading cause of infant viral death and mortality among this population is 10 times greater than mortality due to influenza infection. Global annual morbidity and mortality estimated to be 64 million and 160,000 deaths respectively. RSV-related medical costs estimated to be >$650 million/year.

While essentially all children experience an infection by two years of age, the peak age for serious RSV infection is at 2-6 months of age. The majority of infections resolve uneventfully. In some children, however, infection may predispose children for asthma and airway hyper-responsiveness later in life. Natural RSV infection does not confer lifetime immunity, and therefore, individuals may be repeatedly infected.

RSV infection raises significant issue among the elderly and other vulnerable populations. Among the elderly, RSV is the second leading cause of viral death. Transplant recipients and other immunocompromised populations as well as individuals suffering from cystic fibrosis are vulnerable to serious health consequences due to infection.

Respiratory Syncytial Virus (RSV) is an enveloped, negative-sense, single-stranded RNA virus of the family Paramyxoviridae, a family which includes common respiratory viruses such as influenza and those causing mumps and measles. In all, RSV has ten genes encoding eleven different proteins. The eleven RSV proteins include: proteins 1) protein "NS1" and 2) protein "NS2", which inhibit type I interferon activity; 3) protein "N", the nuclcocapsid protein which associates with RNA forming nucleocapsid; 4) protein "P", which is a cofactor for protein L; 5) protein "M", the matrix protein which required for viral assembly; 6) protein "SH", which is expressed on the viral surface forms the viral coat with protein G and protein F; 7) protein "G", which is highly glycosylated, expressed on the surface, involved in viral attachment and binds glycosaminoglycans (GAGs); 8) protein "F", which is expressed on the surface, viral-cell membrane fusion and mediating fusion to allow entry of virus into the cell cytoplasm; 9) protein "M2-1", which is a matrix protein and elongation factor; 10) protein "M2-2", which is a matrix protein and transcription factor; and, 11) protein "L", which is RNA polymerase. The M2 gene encodes both protein M2-1 and protein M2-2 in overlapping open reading frames. The primary CD8 T cell epitope is encoded by the M2 gene. There are two major subtypes of human RSV-A and B. The major difference between the two subtypes resides within the G protein.

RSV infection often results both immune mediated pathology and virus mediated pathology. Primary RSV infection often results in acute bronchiolitis that leads to inflammation-induced airway obstruction. RSV F binding has been shown to induce apoptosis resulting in the sloughing of ciliated epithelial cells, compromised pulmonary clearance, and consequent secondary infections.

Unfortunately, despite the immense effort, there are still no effective vaccines available for RSV. In 1966-1967, first RSV vaccine candidate, a formalin-inactivated alum-precipitated RSV preparation (FI-RSV vaccine) resulted in enhanced disease in vaccinated children upon subsequent natural infection. Histological analysis of lungs of children who died from enhanced disease caused by infection after vaccination revealed extensive mononuclear cell infiltration including pulmonary eosinophilia. The FI-RSV vaccine generated only binding antibodies without neutralizing activity because of denatured F protein and did not induce CTL activity.

Subsequent experiments have suggested that this enhanced pulmonary disease is associated with an exaggerated Th2-type cytokine response by CD4 T cells, a poor cytolytic response by CD8 T cells, and a weak neutralizing antibody response. RSV infection of FI-RSV vaccinated BALB/c and C57BL/6 mice resulted in enhanced disease observed in FI-RSV vaccinated children. Characteristic of a Th2-mediated immune response suggested immunized children were primed for Th2 immune response by vaccine. Increased levels of Th2-associated cytokines IL-5, IL-4, and IL-13 and chemokineeotaxin with a decrease in Th1-associated cytokine IL-12 were exhibited. Depletion of IL-4, IL-10, or IL-13 resulted in significant decrease in enhanced disease after RSV challenge.

Live attenuated and inactivated whole virus vaccines have also failed to protect. The candidate vaccines were either insufficiently attenuated or demonstrated the potential for enhanced disease. In 1982, a live attenuated RSV vaccine was found to be safe, but not effective for prevention of RSV illness.

In 1983, a Native American infant, "Baby Moose", who was thought to have B streptococcal disease but who actually was infected with RSV, serendipitously improved when he received IGIV. This result prompted study of IGIV for RSV disease. In the mid 1980s through 1990 studies of standard IGIV for treatment and prevention of RSV illness validated the role of antibodies in prevention of RSV disease.

In the early 1990s, RSV vaccine studies were re-initiated using various subunit varieties. These trials failed to show significant protection from disease.

From mid 1990s to early 2002, clinical trials of palivizumab (monoclonal antibody specific for RSV-F) for prevention of serious respiratory tract disease caused by RSV produced positive results. In September 2003, palivizumab was approved for prevention of RSV-associated disease in high-risk children. Prophylactic treatment with palivizumab is effective in reducing the severity of disease, but is only recommended for high-risk patients due to the high cost involved in the treatment.

Although past studies have failed to yield in effective RSV vaccines, they have convincingly demonstrated the importance of immune responses in providing a thorough protection against RSV infection. Studies have found evidence supporting the importance of humoral responses and antibodies in protection against RSV-mediated disease. The presence of IgG antibodies in the lung directly correlates with reduced viral load and children with less severe RSV disease often have significantly higher anti-RSV antibody titers before infection Antibody to fusion protein is an important correlate of immunity. Infants who did not become infected with RSV had higher mean titers of IgG than infected infants and were born to mothers who had significantly higher maternal RSV-specific IgG antibody levels than the mothers of infants who became infected. The importance of antibody in mediating protection helps explain why premature infants are at such high risk for serious illness after RSV infection. Maternal IgG is not efficiently transferred to the fetus until the third trimester of pregnancy.

Similarly, the importance of cellular immune responses in providing a thorough protection against RSV infection has also been demonstrated. Children with T cell deficiency have difficulty clearing the virus and are more susceptible to subsequent RSV infection. In animal studies, depletion of CD8 T cells alone in mice does not result in chronic infection, but does result in delayed viral clearance. Clearance requires IFN-γ, FasL, TNF-α. Deficiency in any of these results in delayed viral clearance. Further, C57BL/6 mice immunized with VV-G do not develop RSV-associated enhanced disease, but depletion of CD8 T cells before immunization results in disease.

There remains a need for an RSV vaccine, including an immunogenic antigen, that induces long-term protection against RSV. There is also a need for a cost-effective delivery system to enable mass prophylactic vaccination against RSV. There is also a need for additional therapeutic agents to treat individuals infected with RSV.

SUMMARY OF THE INVENTION

Nucleic acid molecules are provided which comprising one or more nucleic acid sequences that encode one or more consensus RSV immunogens. The RSV immunogens include the consensus RSV F immunogen, the consensus RSV-G(A) immunogen, and the consensus RSV G(B) immunogen.

Compositions are provided which comprise one or more nucleic acid sequences that encode an RSV immunogen. The nucleic acids are selected from the group consisting of: a) a nucleic acid coding sequence that encodes an RSV F immunogen, b) a nucleic acid coding sequence that encodes an RSV Ga immunogen, and c) a nucleic acid coding sequence that encodes an RSV Gb immunogen.

In some embodiments, the nucleic acid coding sequence that encodes an RSV F immunogen encodes an RSV F immunogen selected from the group consisting of: SEQ ID NO:2, a fragment of SEQ ID NO:2, a protein that is at least 98% homologous to SEQ ID NO:2 and a fragment of a protein that is at least 98% homologous to SEQ ID NO:2. In each instance, the nucleic acid coding sequence that encodes an RSV F immunogen may optionally further comprise coding sequence that encodes a signal peptide operably linked to the sequence.

In some embodiments, the nucleic acid coding sequence that encodes an RSV Ga immunogen encodes an RSV Ga immunogen selected from the group consisting of: SEQ ID NO:6, a fragment of SEQ ID NO:6, a protein that is at least 98% homologous to SEQ ID NO:6 and a fragment of a protein that is at least 98% homologous to SEQ ID NO:6. In each instance, the nucleic acid coding sequence that encodes an RSV Ga immunogen may optionally further comprise coding sequence that encodes a signal peptide operably linked to the sequence.

In some embodiments, the nucleic acid coding sequence that encodes an RSV Gb immunogen encodes an RSV Gb immunogen selected from the group consisting of: SEQ ID NO:8, a fragment of SEQ ID NO:8, a protein that is at least 98% homologous to SEQ ID NO:8 and a fragment of a protein that is at least 98% homologous to SEQ ID NO:8. In each instance, the nucleic acid coding sequence that encodes an RSV Gb immunogen may optionally further comprise coding sequence that encodes a signal peptide operably linked to the sequence.

In some embodiments, the nucleic acid coding sequence that encodes an RSV F immunogen is selected from the group consisting of: nucleic acid sequences comprising SEQ ID NO:1, nucleic acid sequences comprising a fragment of SEQ ID NO:1, nucleic acid sequences comprising sequences that is at least 98% homologous to SEQ ID NO:1, and nucleic acid sequences comprising a fragment of a sequence that is at least 98% homologous to SEQ ID NO:1. In each instance, the nucleic acid coding sequence that encodes an RSV F immunogen may optionally further comprise coding sequence that encodes a signal peptide operably linked to the sequence. Nucleic acid sequences comprising sequences that is at least 98% homologous to SEQ ID NO:1 preferable encode a protein that is at least 98% homologous to SEQ ID NO:2. Nucleic acid sequences comprising a fragment of a sequence that is at least 98% homologous to SEQ ID NO:1 preferable encode a fragment of a protein that is at least 98% homologous to SEQ ID NO:2.

In some embodiments, the nucleic acid coding sequence that encodes an RSV Ga immunogen is selected from the group consisting of: nucleic acid sequences comprising SEQ ID NO:5, nucleic acid sequences comprising a fragment of SEQ ID NO:5, nucleic acid sequences comprising sequences that is at least 98% homologous to SEQ ID NO:5, and nucleic acid sequences comprising a fragment of a sequence that is at least 98% homologous to SEQ ID NO:5. In each instance, the nucleic acid coding sequence that encodes an RSV Ga immunogen may optionally further comprise coding sequence that encodes a signal peptide operably linked to the sequence. Nucleic acid sequences comprising sequences that is at least 98% homologous to SEQ ID NO:5 preferable encode a protein that is at least 98% homologous to SEQ ID NO:6. Nucleic acid sequences comprising a fragment of a sequence that is at least 98% homologous to SEQ ID NO:5 preferable encode a fragment of a protein that is at least 98% homologous to SEQ ID NO:6.

In some embodiments, the nucleic acid coding sequence that encodes an RSV Gb immunogen is selected from the group consisting of: nucleic acid sequences comprising SEQ ID NO:7, nucleic acid sequences comprising a fragment of SEQ ID NO:7, nucleic acid sequences comprising sequences that is at least 98% homologous to SEQ ID NO:7, and nucleic acid sequences comprising a fragment of a sequence that is at least 98% homologous to SEQ ID NO:7. In each instance, the nucleic acid coding sequence that encodes an RSV Gb immunogen may optionally further comprise coding sequence that encodes a signal peptide operably linked to the sequence. Nucleic acid sequences comprising sequences that is at least 98% homologous to SEQ ID NO:7 preferable encode a protein that is at least 98% homologous to SEQ ID NO:8. Nucleic acid sequences comprising a fragment of a sequence that is at least 98% homologous to SEQ ID NO:7 preferable encode a fragment of a protein that is at least 98% homologous to SEQ ID NO:8.

In some embodiments, the compositions comprises one or more nucleic acid sequences selected from the group consisting of: a nucleic acid sequence that encodes SEQ ID NO:10; a nucleic acid sequence that encodes SEQ ID NO:14; and a nucleic acid sequence that encodes SEQ ID NO:16.

In some embodiments, the compositions comprise one or more nucleic acid sequences selected from the group consisting of: a nucleic acid sequence comprising SEQ ID NO:9; a nucleic acid sequence comprising SEQ ID NO:13; and a nucleic acid sequence comprising SEQ ID NO:15.

In some embodiments, the compositions comprises nucleic acid sequences selected from the group consisting of:

a nucleic acid coding sequence that encodes an RSV F immunogen, a nucleic acid coding sequence that encodes an RSV Ga immunogen, a nucleic acid coding sequence that encodes an RSV Gb immunogen, a nucleic acid coding sequence that encodes an RSV F immunogen and a nucleic acid coding sequence that encodes an RSV Ga immunogen, a nucleic acid coding sequence that encodes an RSV F immunogen and a nucleic acid coding sequence that encodes an RSV Gb immunogen, a nucleic acid coding sequence that encodes an RSV Ga immunogen and a nucleic acid coding sequence that encodes an RSV Gb immunogen, a nucleic acid coding sequence that encodes an RSV F immunogen, a nucleic acid coding sequence that encodes an RSV Ga immunogen and a nucleic acid coding sequence that encodes an RSV Gb immunogen, The composition may further comprise a nucleic acid coding sequence that encodes CCL20 and/or be formulated for delivery to an individual using electroporation and/or further comprising nucleic acid sequences that encode one or more proteins selected from the group consisting of: IL-12, IL-15 and IL-28.

In some embodiments, one or more nucleic acid coding sequences are part of one or more plasmids. In some embodiments, one or more nucleic acid coding sequences are each incorporated into a separate plasmid.

Method are provided for inducing an immune response against RSV comprising administering a composition to an individual in an amount effective to induce an immune response in said individual.

Method are provided for treating an individual who has been diagnosed with RSV comprising administering a therapeutically effective amount of a composition to an individual.

Method are provided for preventing RSV infection an individual comprising administering a prophylactically effective amount of the composition to an individual.

Novel "RSV F immunogen", "RSV Ga immunogen", and "RSV Gb immunogen" are provided. In some embodiments, proteins selected from the group consisting of: SEQ ID NO:2; SEQ ID NO:6; SEQ ID NO:8; SEQ ID NO:10; SEQ ID NO:14; and SEQ ID NO:16 are provided.

Methods of modulating immune responses using a nucleic acid coding sequence that encodes the chemokine CCL20 are also provided.

In addition, provided herein is a nucleic acid coding sequence that encodes a consensus RSV M2-1 immunogen. In some embodiments, the nucleic acid coding sequence that encodes an RSV M2-1 immunogen encodes an RSV M2-1 immunogen selected from the group consisting of: SEQ ID NO:4, a fragment of SEQ ID NO:4, a protein that is at least 98% homologous to SEQ ID NO:4 and a fragment of a protein that is at least 98% homologous to SEQ ID NO:4. In each instance, the nucleic acid coding sequence that encodes an RSV M2-1 immunogen may optionally further comprise coding sequence that encodes a signal peptide operably linked to the sequence.

In some embodiments, the nucleic acid coding sequence that encodes an RSV M2-1 immunogen is selected from the group consisting of: nucleic acid sequences comprising SEQ ID NO:3, nucleic acid sequences comprising a fragment of SEQ ID NO:3, nucleic acid sequences comprising sequences that is at least 98% homologous to SEQ ID NO:3, and nucleic acid sequences comprising a fragment of a sequence that is at least 98% homologous to SEQ ID NO:3. In each instance, the nucleic acid coding sequence that encodes an RSV M2-1 immunogen may optionally further comprise coding sequence that encodes a signal peptide operably linked to the sequence. Nucleic acid sequences comprising sequences that is at least 98% homologous to SEQ ID NO:3 preferable encode a protein that is at least 98% homologous to SEQ ID NO:4. Nucleic acid sequences comprising a fragment of a sequence that is at least 98% homologous to SEQ ID NO:3 preferable encode a fragment of a protein that is at least 98% homologous to SEQ ID NO:4.

In some embodiments, compositions are provided which comprises one or more nucleic acid sequences including a nucleic acid sequence that encodes SEQ ID NO:12.

In some embodiments, the compositions are provided which comprise one or more nucleic acid sequences including a nucleic acid sequence comprising SEQ ID NO:11.

In some embodiments, the compositions comprises nucleic acid sequences selected from the group consisting of: a nucleic acid coding sequence that encodes an RSV M2-1 immunogen, a nucleic acid coding sequence that encodes an RSV F immunogen and a nucleic acid coding sequence that encodes an RSV M2-1 immunogen, a nucleic acid coding sequence that encodes an RSV M2-1 immunogen and a nucleic acid coding sequence that encodes an RSV Ga immunogen, a nucleic acid coding sequence that encodes an RSV M2-1 immunogen and a nucleic acid coding sequence that encodes an RSV Gb immunogen, a nucleic acid coding sequence that encodes an RSV F immunogen, a nucleic acid coding sequence that encodes an RSV M2-1 immunogen and a nucleic acid coding sequence that encodes an RSV Ga immunogen, a nucleic acid coding sequence that encodes an RSV F immunogen, a nucleic acid coding sequence that encodes an RSV M2-1 immunogen and a nucleic acid coding sequence that encodes an RSV Gb immunogen, a nucleic acid coding sequence that encodes an RSV M2-1 immunogen, a nucleic acid coding sequence that encodes an RSV Ga immunogen and a nucleic acid coding sequence that encodes an RSV Gb immunogen, and a nucleic acid coding sequence that encodes an RSV F immunogen, a nucleic acid coding sequence that encodes an RSV M2-1 immunogen, a nucleic acid coding sequence that encodes an RSV Ga immunogen and a nucleic acid coding sequence that encodes an RSV Gb immunogen.

Novel ""RSV M2-1 immunogen is also provided. In some embodiments, proteins selected from the group consisting of: SEQ ID NO:4 and SEQ ID NO:12 are provided.

BRIEF DESCRIPTION OF THE DRAWINGS

FIG. 1 shows the phylogenetic tree of RSV-F Protein, the consensus RSV F protein amino acid sequence is set forth in SEQ ID NO:2.

FIG. 12 depicts RSV-Fusion Pseudo viral production in 293T cells.

FIG. 14 shows data from quantification of RSV-F mediated infection in different target cells.

FIG. 18 shows data collected from that study including a comparison of IFN-g production at different dosages of RSV-M2 vaccine 1 week after last immunization.

FIGS. 22A-22C show plasmid designs and construction of RSV-F, RSV-G(A), and RSV-G(B) constructs. FIG. 22A shows plasmid design and construction of RSV-F construct. FIG. 22B shows plasmid design and construction of RSV-G(A) construct. FIG. 22C shows plasmid design and construction of RSV-G(B) construct.

FIG. 30 shows the immunization schedule for an RSV-G (A) and RSV-(B) Dosage Study.

FIG. 38A-38D show data from the RSV Non-Human Primate Study of measured humoral immunity against RSV-F. FIG. 38A shows data from measured humoral immunity against RSV-F in naïve animals. FIG. 38B shows data from measured humoral immunity against RSV-F in animals who received the cocktail vaccine IM at one site. FIG. 38C shows data from measured humoral immunity against RSV-F in animals who received the cocktail vaccine plus rhMEC construct IM at one site. FIG. 38D shows data from measured humoral immunity against RSV-F in animals who received the cocktail vaccine ID at three sites.

FIG. 39A-39D show data from the RSV Non-Human Primate Study of measured humoral immunity against RSV-G. FIG. 39A shows data from measured humoral immunity against RSV-G in naïve animals. FIG. 39B shows data from measured humoral immunity against RSV-G in animals who received the cocktail vaccine IM at one site. FIG. 39C shows data from measured humoral immunity against RSV-G in animals who received the cocktail vaccine plus rhMEC construct IM at one site. FIG. 39D shows data from measured humoral immunity against RSV-G in animals who received the cocktail vaccine ID at three sites.

DETAILED DESCRIPTION OF THE PREFERRED EMBODIMENT

Figure 2:
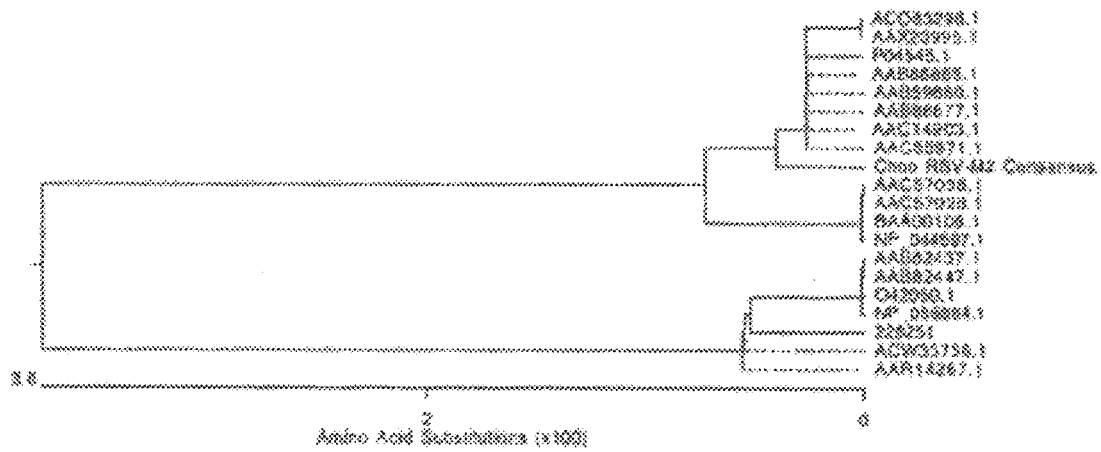
FIG. 2 shows the phylogenetic tree of RSV M2-1 Protein, the consensus RSV M2-1 protein amino acid sequence is set forth in SEQ ID NO:4.

In one aspect of the invention, it is desired that the consensus antigen provides for improved transcription and translation, including having one or more of the following: low GC content leader sequence to increase transcription; mRNA stability and codon optimization; eliminating to the extent possible cis-acting sequence motifs (i.e., internal TATA-boxes).

In some aspects of the invention, it is desired to generate a consensus antigen that generates a broad immune response across multiple strains, including having one or more of the following: incorporate all available full-length sequences; computer generate sequences that utilize the most commonly occurring amino acid at each position; and increase cross-reactivity between strains.

The attached Sequence Listing includes SEQ ID NOs:1-16 which are various RSV sequences and embodiments.

SEQ ID NO:1 shows a nucleotide sequence encoding an RSV F without start codon (ATG) or signal peptide.

SEQ ID NO:2 shows an amino sequence encoding an RSV F without Met encoded by a start codon (ATG) or signal peptide.

SEQ ID NO:3 shows a nucleotide sequence encoding an RSV M2-1 without start codon (ATG) or signal peptide.

SEQ ID NO:4 shows an amino sequence encoding an RSV M2-1 without Met encoded by a start codon (ATG) or signal peptide.

SEQ ID NO:5 shows a nucleotide sequence encoding an RSV Ga without start codon (ATG) or signal peptide.

SEQ ID NO:6 shows an amino sequence encoding RSV Ga without Met encoded by a start codon (ATG) or signal peptide.

SEQ ID NO:7 shows a nucleotide sequence encoding an RSV Gb without start codon (ATG) or signal peptide.

SEQ ID NO:8 shows an amino sequence encoding an RSV Gb without Met encoded by a start codon (ATG) or signal peptide.

SEQ ID NO:9 shows a nucleotide sequence encoding an RSV F including start codon (ATG)/sequences encoding IgE signal peptide.

SEQ ID NO:10 shows an amino sequence encoding an RSV F with Met encoded by start codon/IgE signal peptide.

SEQ ID NO:11 shows a nucleotide sequence encoding an RSV M2-1 including start codon (ATG)/sequences encoding IgE signal peptide.

SEQ ID NO:12 shows an amino sequence encoding an RSV M2-1 with Met encoded by start codon/IgE signal peptide.

SEQ ID NO:13 shows a nucleotide sequence encoding an RSV Ga including start codon (ATG)/sequences encoding IgE signal peptide.

SEQ ID NO:14 shows an amino sequence encoding an RSV Ga with Met encoded by start codon/IgE signal peptide.

SEQ ID NO:15 shows a nucleotide sequence encoding an RSV Gb including start codon (ATG)/sequences encoding IgE signal peptide.

SEQ ID NO:16 shows an amino sequence encoding an RSV Gb with Met encoded by start codon/IgE signal peptide.

The attached Sequence Listing includes SEQ ID NO:17 which is the amino acid sequence of the IgE signal peptide.

SEQ ID NO:17 shows and amino acid sequence of an IgE signal peptide.

The attached Sequence Listing includes SEQ ID NOs:18-21 which are various CCL20 sequences and embodiments.

SEQ ID NO:18 shows a nucleotide sequence encoding an CCL20 without start codon (ATG) or signal peptide SEQ ID NO:19 CCL20 without Met encoded by a start codon (ATG) or signal peptide SEQ ID NO:20 shows a nucleotide sequence encoding an CCL20 including start codon (ATG)/sequences encoding IgE signal peptide SEQ ID NO:21 CCL20 with Met encoded by start codon/IgE signal peptide The attached Sequence Listing includes SEQ ID NO:22-31 which are amino acid sequences of derived from RSV immunogens.

SEQ ID NO:22 is a T cell epitope of RSV F Immunogen.
SEQ ID NO:23 is a T cell epitope of RSV F Immunogen.
SEQ ID NO:24 is a T cell epitope of RSV F Immunogen.
SEQ ID NO:25 is a T cell epitope of RSV F Immunogen.
SEQ ID NO:26 is a RSV F Immunogen protease cleavage site.
SEQ ID NO:27 is a RSV F Immunogen protease cleavage site.
SEQ ID NO:28 is a RSV F Immunogen fusion peptide.
SEQ ID NO:29 is a RSV F Immunogen binding site for palivizumab.
SEQ ID NO:30 is a RSV M2-1 Immunodominant T cell epitope.
SEQ ID NO:31 is a RSV M2-1 Subdominant T cell epitope.

In some aspects of the invention. RSV F immunogen and sequences that encode the RSV F immunogen are provided. In some aspects of the invention, RSV Ga immunogen and sequences that encode the RSV Ga immunogen are provided. In some aspects of the invention, RSV Gb immunogen and sequences that encode the RSV Gb immunogen are provided. Compositions comprising combinations sequences that encode the RSV F immunogen, sequences that encode the RSV Ga immunogen and sequences that encode the RSV Gb immunogen are provided, including each of sequences that encode the RSV F immunogen, sequences that encode the RSV Ga immunogen and sequences that encode the RSV Gb immunogen.

RSV M2-1 immunogen and sequences that encode the RSV M2-1 immunogen are also provided and my be used alone or in combination with other proteins and/or nucleic acid sequences.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

a. Adjuvant

"Adjuvant" as used herein may mean any molecule added to the DNA plasmid vaccines described herein to enhance antigenicity of the one or more Respiratory Syncytial Virus (RSV) antigens encoded by the DNA plasmids and encoding nucleic acid sequences described hereinafter.

b. Antibody

"Antibody" may mean an antibody of classes IgG, IgM, IgA, IgD or IgE, or fragments, fragments or derivatives thereof, including Fab, F(ab')2, Fd, and single chain antibodies, diabodies, bispecific antibodies, bifunctional antibodies and derivatives thereof. The antibody may be an antibody isolated from the serum sample of mammal, a polyclonal antibody, affinity purified antibody, or mixtures thereof which exhibits sufficient binding specificity to a desired epitope or a sequence derived therefrom.

c. Coding Sequence

"Coding sequence" or "encoding nucleic acid" as used herein may mean refers to the nucleic acid (RNA or DNA molecule) that comprise a nucleotide sequence which encodes a protein. The coding sequence may further include initiation and termination signals operably linked to regulatory elements including a promoter and polyadenylation signal capable of directing expression in the cells of an individual or mammal to whom the nucleic acid is administered.

In some embodiments, the coding sequence for the amino acid sequence of consensus RSV F immunogen, which is set forth in SEQ ID NO:2, is SEQ ID NO:1. Such coding sequence may optionally further comprise a start codon that encodes an N terminal methionine or a signal peptide such as an IgE or IgG signal peptide. SEQ ID NO:10 corresponds to SEQ ID NO:2 with an IgE signal peptide (SEQ ID NO:17). SEQ ID NO:9 encodes SEQ ID NO:10.

In some embodiments, the coding sequence for the amino acid sequence of consensus RSV Ga immunogen, which is set forth in SEQ ID NO:6, is SEQ ID NO:5. Such coding sequence may optionally further comprise a start codon that encodes an N terminal methionine or a signal peptide such as an IgE or IgG signal peptide. SEQ ID NO:14 corresponds to SEQ ID NO:6 with an IgE signal peptide (SEQ ID NO:17). SEQ ID NO:13 encodes SEQ ID NO:14.

In some embodiments, the coding sequence for the amino acid sequence of consensus RSV Gb immunogen, which is set forth in SEQ ID NO:8, is SEQ ID NO:7. Such coding sequence may optionally further comprise a start codon that encodes an N terminal methionine or a signal peptide such as an IgE or IgG signal peptide. SEQ ID NO:16 corresponds to SEQ ID NO:8 with an IgE signal peptide (SEQ ID NO:17). SEQ ID NO:15 encodes SEQ ID NO:16.

Also provides is a coding sequence, SEQ ID NO:3, which encodes the amino acid sequence of consensus RSV M2-1 immunogen, which is set forth in SEQ ID NO:4. Such coding sequence may optionally further comprise a start codon that encodes an N terminal methionine or a signal peptide such as an IgE or IgG signal peptide. SEQ ID NO:12 corresponds to SEQ ID NO:4 with an IgE signal peptide (SEQ ID NO:17). SEQ ID NO:11 encodes SEQ ID NO:12.

d. Complement

"Complement" or "complementary" as used herein may mean a nucleic acid may mean Watson-Crick (e.g., A-T/U and C-G) or Hoogsteen base pairing between nucleotides or nucleotide analogs of nucleic acid molecules.

e. Consensus or Consensus Sequence

"Consensus" or "consensus sequence" as used herein may mean a synthetic nucleic acid sequence, or corresponding polypeptide sequence, constructed based on analysis of an alignment of multiple subtypes of a particular RSV antigen, that can be used to induce broad immunity against multiple subtypes or serotypes of a particular RSV antigen. Consensus RSV antigens may include consensus amino acid sequences of protein F, protein G and protein M2. Nucleotide sequences that encode the consensus amino acid sequences are also provided. Also, synthetic antigens such as fusion proteins may be manipulated to include consensus sequences (or consensus antigens).

The amino acid sequence of consensus RSV F immunogen is set forth in SEQ ID NO:2. Such sequence may optionally comprise an N terminal methionine or a signal peptide such as an IgE or IgG signal peptide. SEQ ID NO:10 corresponds to SEQ ID NO:2 with an IgE signal peptide (SEQ ID NO:17).

The amino acid sequence of consensus RSV Ga immunogen is set forth in SEQ ID NO:6. Such sequence may optionally comprise an N terminal methionine or a signal peptide such as an IgE or IgG signal peptide. SEQ ID NO:14 corresponds to SEQ ID NO:6 with an IgE signal peptide (SEQ ID NO:17).

The amino acid sequence of consensus RSV Gb immunogen is set forth in SEQ ID NO:8. Such sequence may optionally comprise an N terminal methionine or a signal peptide such as an IgE or IgG signal peptide. SEQ ID NO:16 corresponds to SEQ ID NO:8 with an IgE signal peptide (SEQ ID NO:17).

Also provided is the amino acid sequence of consensus RSV M2-1 immunogen which is set forth in SEQ ID NO:4. Such sequence may optionally comprise an N terminal methionine or a signal peptide such as an IgE or IgG signal peptide. SEQ ID NO:12 corresponds to SEQ ID NO:4 with an IgE signal peptide (SEQ ID NO:17).

f. Constant Current

"Constant current" as used herein to define a current that is received or experienced by a tissue, or cells defining said tissue, over the duration of an electrical pulse delivered to same tissue. The electrical pulse is delivered from the electroporation devices described herein. This current remains at a constant amperage in said tissue over the life of an electrical pulse because the electroporation device provided herein has a feedback element, preferably having instantaneous feedback. The feedback element can measure the resistance of the tissue (or cells) throughout the duration of the pulse and cause the electroporation device to alter its electrical energy output (e.g., increase voltage) so current in same tissue remains constant throughout the electrical pulse (on the order of microseconds), and from pulse to pulse. In some embodiments, the feedback element comprises a controller.

g. Current Feedback or Feedback

"Current feedback" or "feedback" as used herein may be used interchangeably and may mean the active response of the provided electroporation devices, which comprises measuring the current in tissue between electrodes and altering the energy output delivered by the EP device accordingly in order to maintain the current at a constant level. This constant level is preset by a user prior to initiation of a pulse sequence or electrical treatment. The feedback may be accomplished by the electroporation component, e.g., controller, of the electroporation device, as the electrical circuit therein is able to continuously monitor the current in tissue between electrodes and compare that monitored current (or current within tissue) to a preset current and continuously make energy-output adjustments to maintain the monitored current at preset levels. The feedback loop may be instantaneous as it is an analog closed-loop feedback.

h. Decentralized Current

"Decentralized current" as used herein may mean the pattern of electrical currents delivered from the various needle electrode arrays of the electroporation devices described herein, wherein the patterns minimize, or preferably eliminate, the occurrence of electroporation related heat stress on any area of tissue being electroporated.

i. Electroporation

"Electroporation," "electro-permeabilization," or "electro-kinetic enhancement" ("EP") as used interchangeably herein may refer to the use of a transmembrane electric field pulse to induce microscopic pathways (pores) in a bio-membrane; their presence allows biomolecules such as plasmids, oligonucleotides, siRNA, drugs, ions, and water to pass from one side of the cellular membrane to the other.

j. Feedback Mechanism

"Feedback mechanism" as used herein may refer to a process performed by either software or hardware (or firmware), which process receives and compares the impedance of the desired tissue (before, during, and/or after the delivery of pulse of energy) with a present value, preferably current, and adjusts the pulse of energy delivered to achieve the preset value. A feedback mechanism may be performed by an analog closed loop circuit.

k. Fragment

"Fragment" may mean a polypeptide fragment of an RSV Immunogen that is capable of eliciting an immune response in a mammal against RSV by recognizing the particular RSV antigen. An RSV Immunogen is refers to the consensus sequences set forth herein for RSV F Immunogen, RSV M2-1 Immunogen, RSV Ga Immunogen, RSV Gb Immunogen, in each case with or without signal peptides and/or a methionine at position 1, proteins 98% or more homologous to the consensus sequences set forth herein, proteins 99% or more homologous to the consensus sequences set forth herein, and proteins 100% identical to the consensus sequences set forth herein, in each case with or without signal peptides and/or a methionine at position 1. A fragment may or may not for example comprise a fragments of an RSV Immunogen linked to a signal peptide such as an immunoglobulin signal peptide for example IgE signal peptide (SEQ ID NO:17) or IgG signal peptide.

A fragment of RSV F consensus Immunogen may be a fragment of SEQ ID NO:2, of SEQ ID NO:10, of a protein 98% or more homologous to the RSV F consensus Immunogen sequences set forth herein, of a protein 99% or more homologous to the RSV F consensus Immunogen sequences set forth herein, or of RSV F consensus Immunogen 100% identical to the consensus sequences set forth herein, in each case with or without signal peptides and/or a methionine at position 1. Such fragments may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length RSV F consensus Immunogen sequence set forth herein, excluding any non-RSV signal peptide added. Fragments refer to fragments of a polypeptide that is 98% or more, or 99% or more homologous to the sequences of the RSV F consensus Immunogen set forth herein and 100% identical to such sequence, in each case with or without signal peptides and/or a methionine at position 1. The fragment may comprise a fragment of a polypeptide that is 98% or more homologous, 99% or more homologous, or 100% identical to the RSV F consensus Immunogen and additionally comprise a signal peptide such as an immunoglobulin signal peptide which is not included when calculating percent homology. In some embodiments, a fragment of RSV F Immunogen may comprise a fragment of a SEQ ID NO:2. The fragment may comprise a fragments of SEQ ID NO:2 linked to a signal peptide such as an immunoglobulin signal peptide for example IgE signal peptide (SEQ ID NO:17) or IgG signal peptide. Thus in some embodiments, the fragment is a fragment of SEQ ID NO:10 which comprises SEQ ID NO:17. The fragment may comprise fragments of SEQ ID NO:2 linked to an N terminal methionine. Fragments also refer to fragments of a polypeptide that is 98% or more, or 99% or more homologous to SEQ ID NO:2. The fragment may comprise a fragment of a polypeptide that is 98% or more homologous to SEQ ID NO:2 and additionally comprise a signal peptide such as an immunoglobulin signal peptide which is not included when calculating percent homology. The fragment may comprise a fragment of a polypeptide that is 99% or more homologous to SEQ ID NO:2 and additionally comprise a signal peptide such as an immunoglobulin signal peptide which is not included when calculating percent homology. The fragment may comprise a fragment of a polypeptide that is 98% or more homologous to SEQ ID NO:2 and additionally comprise an N terminal methionine which is not included when calculating percent homology. The fragment may comprise a fragment of a polypeptide that is 99% or more homologous to SEQ ID NO:2 and additionally comprise an N terminal methionine which is not included when calculating percent homology. The RSV F Immunogen is 575 amino acids. In some embodiments, the fragments thereof may be 115 or more amino acids in length, 163 or more, 230 or more, 288 or more, 345 or more, 403 or more, 460 or more, 515 or more, 520 or more, 525 or more, 530 or more, 535 or more, 540 or more, 545 or more, 550 or more, 555 or more, 560 or more, 565 or more, 570 or more, 574 or more in length. Polypeptide fragments may be fewer than 140 amino acids, fewer than 190, fewer than 250, fewer than 283, fewer than 300, fewer than 365, fewer than 425, fewer than 495, fewer than 518, fewer than 523, fewer than 528, fewer than 533, fewer than 547, fewer than 552, fewer than 563, or fewer than 572 in length. Fragments may further comprise an N terminal methionine and/or a signal peptide such as an immunoglobulin signal peptide, for example an IgE or IgG signal peptide. The N terminal methionine and/or signal peptide may be linked to a 574 amino acid or smaller fragment thereof. The N terminal methionine and/or signal peptide may be linked to a polypeptide that is 98% homologous to the 574 amino acid or to a smaller fragment of a polypeptide that is 98% homologous to the 574 amino acid sequence. The N terminal methionine and/or signal peptide may be linked to a polypeptide that is 99% homologous to the 574 amino acid sequence or to a smaller fragment of a polypeptide that is 99% homologous to the 574 amino acid sequence. In calculating degrees of homology a polypeptide has to SEQ ID NO:2 or a fragment thereof, an N terminal methionine and/or any signal peptide is not included in such calculation. The sequences of the signal peptide are not used in determining homology. Thus, for example, although SEQ ID NO:10 comprises SEQ ID NO:2 operably linked to a signal peptide SEQ ID NO:17, SEQ ID NO:10 comprises a fragment of SEQ ID NO:2, that is 100% homologous to a fragment of SEQ ID NO:2, notwithstanding the signal peptide which is absent in SEQ ID NO:2. Thus, proteins which comprise fragments of a polypeptide that is at least 98% homologous to a fragment of SEQ ID NO:2 intended to refer to proteins which fragments of a polypeptide that is at least 98% homologous to a fragment of SEQ ID NO:2 that are at least 115 amino acids and may optionally be linked to a, for example, a signal peptide. SEQ ID NO:22, SEQ ID NO:23, SEQ ID NO:24, and SEQ ID NO:25 correspond to T cell epitopes of RSV F immunogen set forth in SEQ ID NO:2. In some embodiments, fragments comprise all or part of one or more of these sequences or sequences 98% or more or 99% or more homologous to them. SEQ ID NO:26 and SEQ ID NO:27 are RSV F Immunogen protease cleavage sites. SEQ ID NO:28 is an RSV F Immunogen fusion peptide. SEQ ID NO:29 is the RSV F Immunogen binding site for palivizumab.

A fragment of RSV Ga consensus Immunogen may be a fragment of SEQ ID NO:6, of SEQ ID NO:14, of a protein 98% or more homologous to the RSV Ga consensus Immunogen sequences set forth herein, of a protein 99% or more homologous to the RSV Ga consensus Immunogen sequences set forth herein, or of RSV Ga consensus Immunogen 100% identical to the consensus sequences set forth herein, in each case with or without signal peptides and/or a methionine at position 1. Such fragments may comprise may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length RSV Ga consensus Immunogen sequence set forth herein, excluding any non-RSV signal peptide added. Fragments refer to fragments of a polypeptide that is 98% or more, or 99% or more homologous to the sequences of the RSV Ga consensus immunogen set forth herein and 100% identical to such sequence, in each case with or without signal peptides and/or a methionine at position 1. The fragment may comprise a fragment of a polypeptide that is 98% or more homologous, 99% or more homologous, or 100% identical to the RSV Ga consensus Immunogen and additionally comprise a signal peptide such as an immunoglobulin signal peptide which is not included when calculating percent homology. In some embodiments, a fragment of RSV Ga Immunogen may comprise a fragment of SEQ ID NO:6. The fragment may comprise a fragments of SEQ ID NO:6 linked to a signal peptide such as an immunoglobulin signal peptide for example IgE signal peptide (SEQ ID NO:17) or IgG signal peptide. Thus in some embodiments, the fragment is a fragment of SEQ ID NO:14 which comprises SEQ ID NO:17. The fragment may comprise fragments of SEQ ID NO:6 linked to an N terminal methionine. Fragments also refer to fragments of a polypeptide that is 98% or more, or 99% or more homologous to SEQ ID NO:6. The fragment may comprise a fragment of a polypeptide that is 98% or more homologous to SEQ ID NO:6 and additionally comprise a signal peptide such as an immunoglobulin signal peptide which is not included when calculating percent homology. The fragment may comprise a fragment of a polypeptide that is 99% or more homologous to SEQ ID NO:6 and additionally comprise a signal peptide such as an immunoglobulin signal peptide which is not included when calculating percent homology. The fragment may comprise a fragment of a polypeptide that is 98% or more homologous to SEQ ID NO:6 and additionally comprise an N terminal methionine which is not included when calculating percent homology. The fragment may comprise a fragment of a polypeptide that is 99% or more homologous to SEQ ID NO:6 and additionally comprise an N terminal methionine which is not included when calculating percent homology. The RSV Ga Immunogen is 297 amino acids excluding an N terminal methionine and/or signal peptide. In some embodiments, the fragments thereof may be 125 or more amino acids in length, 130 or more, 140 or more, 150 or more, 160 or more, 170 or more, 180 or more, 190 or more, 200 or more, 210 or more, 220 or more, 230 or more, 240 or more, 250 or more, 260 or more, 270 or more, 280 or more, 285 or more, 290 or more, 295 or more in length. Polypeptide fragments may be fewer than 135 amino acids, fewer than 145, fewer than 155, fewer than 165, fewer than 175, fewer than 185, fewer than 195, fewer than 205, fewer than 215, fewer than 225, fewer than 235, fewer than 245, fewer than 255, fewer than 265, fewer than 275, fewer than 285, fewer than 288, fewer than 292, or fewer than 296 in length. Fragments may further comprise an N terminal methionine and/or a signal peptide such as an immunoglobulin signal peptide, for example an IgE or IgG signal peptide. The N terminal methionine and/or signal peptide may be linked to a 296 amino acid or smaller fragment thereof. The N terminal methionine and/or signal peptide may be linked to a polypeptide that is 98% homologous to the 296 amino acid or to a smaller fragment of a polypeptide that is 98% homologous to the 296 amino acid sequence. The N terminal methionine and/or signal peptide may be linked to a polypeptide that is 99% homologous to the 296 amino acid sequence or to a smaller fragment of a polypeptide that is 99% homologous to the 296 amino acid sequence. In calculating degrees of homology a polypeptide has to SEQ ID NO:6 or a fragment thereof, an N terminal methionine and/or any signal peptide is not included in such calculation. The sequences of the signal peptide are not used in determining homology. Thus, for example, although SEQ ID NO:14 comprises SEQ ID NO:6 operably linked to a signal peptide SEQ ID NO:17, SEQ ID NO:14 comprises a fragment of SEQ ID NO:6, that is 100% homologous to a fragment of SEQ ID NO:6, notwithstanding the signal peptide which is absent in SEQ ID NO:6. Thus, proteins which comprise fragments of a polypeptide that is at least 98% homologous to a fragment of SEQ ID NO:6 intended to refer to proteins which fragments of a polypeptide that is at least 98% homologous to a fragment of SEQ ID NO:6 that are at least 125 amino acids and may optionally be linked to a, for example, a signal peptide.

A fragment of RSV Gb consensus Immunogen such as that which is disclosed in SEQ ID NO:8, SEQ ID NO:16, proteins 98% or more homologous to the RSV Gb consensus Immunogen sequences set forth herein, proteins 99% or more homologous to the RSV Gb consensus Immunogen sequences set forth herein, and RSV Gb consensus Immunogen 100% identical to the consensus sequences set forth herein, in each case with or without signal peptides and/or a methionine at position 1, may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length RSV Gb consensus Immunogen sequence set forth herein, excluding any non-RSV signal peptide added. Fragments refer to fragments of a polypeptide that is 98% or more, or 99% or more homologous to the sequences of the RSV Gb consensus Immunogen set forth herein and 100% identical to such sequence, in each case with or without signal peptides and/or a methionine at position 1. The fragment may comprise a fragment of a polypeptide that is 98% or more homologous, 99% or more homologous, or 100% identical to the RSV Gb consensus Immunogen and additionally comprise a signal peptide such as an immunoglobulin signal peptide which is not included when calculating percent homology. In some embodiments, a fragment of RSV Gb Immunogen may comprise a fragment of SEQ ID NO:8. The fragment may comprise a fragments of SEQ ID NO:8 linked to a signal peptide such as an immunoglobulin signal peptide for example IgE signal peptide (SEQ ID NO:17) or IgG signal peptide. Thus in some embodiments, the fragment is a fragment of SEQ ID NO:16 which comprises SEQ ID NO:17. The fragment may comprise fragments of SEQ ID NO:8 linked to an N terminal methionine. Fragments also refer to fragments of a polypeptide that is 98% or more, or 99% or more homologous to SEQ ID NO:8. The fragment may comprise a fragment of a polypeptide that is 98% or more homologous to SEQ ID NO:8 and additionally comprise a signal peptide such as an immunoglobulin signal peptide which is not included when calculating percent homology. The fragment may comprise a fragment of a polypeptide that is 99% or more homologous to SEQ ID NO:8 and additionally comprise a signal peptide such as an immunoglobulin signal peptide which is not included when calculating percent homology. The fragment may comprise a fragment of a polypeptide that is 98% or more homologous to SEQ ID NO:8 and additionally comprise an N terminal methionine which is not included when calculating percent homology. The fragment may comprise a fragment of a polypeptide that is 99% or more homologous to SEQ ID NO:8 and additionally comprise an N terminal methionine which is not included when calculating percent homology. The RSV Gb Immunogen is 291 amino acids excluding an N terminal methionine and/or signal peptide. In some embodiments, the fragments thereof may be 125 or more amino acids in length, 130 or more, 140 or more, 150 or more, 160 or more, 170 or more, 180 or more, 190 or more, 200 or more, 210 or more, 220 or more, 230 or more, 240 or more, 250 or more, 260 or more, 270 or more, 280 or more, 285 or more, 288 or more in length. Polypeptide fragments may be fewer than 135 amino acids, fewer than 145, fewer than 155, fewer than 165, fewer than 175, fewer than 185, fewer than 195, fewer than 205, fewer than 215, fewer than 225, fewer than 235, fewer than 245, fewer than 255, fewer than 265, fewer than 275, fewer than 285, fewer than 288, fewer than 290 in length. Fragments may further comprise an N terminal methionine and/or a signal peptide such as an immunoglobulin signal peptide, for example an IgE or IgG signal peptide. The N terminal methionine and/or signal peptide may be linked to a 290 amino acid or smaller fragment thereof. The N terminal methionine and/or signal peptide may be linked to a polypeptide that is 98% homologous to the 290 amino acid or to a smaller fragment of a polypeptide that is 98% homologous to the 290 amino acid sequence. The N terminal methionine and/or signal peptide may be linked to a polypeptide that is 99% homologous to the 290 amino acid sequence or to a smaller fragment of a polypeptide that is 99% homologous to the 290 amino acid sequence. In calculating degrees of homology a polypeptide has to SEQ ID NO:6 or a fragment thereof, an N terminal methionine and/or any signal peptide is not included in such calculation. The sequences of the signal peptide are not used in determining homology. Thus, for example, although SEQ ID NO:16 comprises SEQ ID NO:8 operably linked to a signal peptide SEQ ID NO:17. SEQ ID NO:16 comprises a fragment of SEQ ID NO:8, that is 100% homologous to a fragment of SEQ ID NO:8, notwithstanding the signal peptide which is absent in SEQ ID NO:8. Thus, proteins which comprise fragments of a polypeptide that is at least 98% homologous to a fragment of SEQ ID NO:8 intended to refer to proteins which fragments of a polypeptide that is at least 98% homologous to a fragment of SEQ ID NO:8 that are at least 125 amino acids and may optionally be linked to a, for example, a signal peptide.

In addition, a fragment of RSV M2-1 consensus Immunogen may be a fragment of SEQ ID NO:4, of SEQ ID NO:12, of a protein 98% or more homologous to the RSV M2-1 consensus Immunogen sequences set forth herein, of a protein 99% or more homologous to the RSV M2-1 consensus Immunogen sequences set forth herein, or of RSV M2-1 consensus Immunogen 100% identical to the consensus sequences set forth herein, in each case with or without signal peptides and/or a methionine at position 1. Such fragments may comprise may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length RSV M2-1 consensus Immunogen sequence set forth herein, excluding any non-RSV signal peptide added. Fragments refer to fragments of a polypeptide that is 98% or more, or 99% or more homologous to the sequences of the RSV M2-1 consensus Immunogen set forth herein and 100% identical to such sequence, in each case with or without signal peptides and/or a methionine at position 1. The fragment may comprise a fragment of a polypeptide that is 98% or more homologous, 99% or more homologous, or 100% identical to the RSV M2-1 consensus Immunogen and additionally comprise a signal peptide such as an immunoglobulin signal peptide which is not included when calculating percent homology. In some embodiments, a fragment of RSV M2-1 Immunogen may comprise a fragment of a SEQ ID NO:4. The fragment may comprise a fragments of SEQ ID NO:4 linked to a signal peptide such as an immunoglobulin signal peptide for example IgE signal peptide (SEQ ID NO:17) or IgG signal peptide. Thus in some embodiments, the fragment is a fragment of SEQ ID NO:12 which comprises SEQ ID NO:17. The fragment may comprise fragments of SEQ ID NO:4 linked to an N terminal methionine. Fragments also refer to fragments of a polypeptide that is 98% or more, or 99% or more homologous to SEQ ID NO:4. The fragment may comprise a fragment of a polypeptide that is 98% or more homologous to SEQ ID NO:4 and additionally comprise a signal peptide such as an immunoglobulin signal peptide which is not included when calculating percent homology. The fragment may comprise a fragment of a polypeptide that is 99% or more homologous to SEQ ID NO:4 and additionally comprise a signal peptide such as an immunoglobulin signal peptide which is not included when calculating percent homology. The fragment may comprise a fragment of a polypeptide that is 98% or more homologous to SEQ ID NO:4 and additionally comprise an N terminal methionine which is not included when calculating percent homology. The fragment may comprise a fragment of a polypeptide that is 99% or more homologous to SEQ ID NO:4 and additionally comprise an N terminal methionine which is not included when calculating percent homology. The RSV M2-1 Immunogen is 195 amino acids. In some embodiments, the fragments thereof may be 25 or more amino acids in length, 30 or more, 40 or more, 50 or more, 60 or more, 70 or more, 80 or more, 90 or more, 100 or more, 10 or more, 120 or more, 130 or more, 140 or more, 150 or more, 160 or more, 170 or more, 180 or more, 184 or more, 190 or more, 193 or more in length. Polypeptide fragments may be fewer than 35 amino acids, fewer than 45, fewer than 55, fewer than 65, fewer than 75, fewer than 85, fewer than 95, fewer than 105, fewer than 115, fewer than 125, fewer than 135, fewer than 145, fewer than 155, fewer than 165, fewer than 175, fewer than 185, fewer than 188, fewer than 192, or fewer than 194 in length. Fragments may further comprise an N terminal methionine and/or a signal peptide such as an immunoglobulin signal peptide, for example an IgE or IgG signal peptide. The N terminal methionine and/or signal peptide may be linked to a 194 amino acid or smaller fragment thereof. The N terminal methionine and/or signal peptide may be linked to a polypeptide that is 98% homologous to the 194 amino acid or to a smaller fragment of a polypeptide that is 98% homologous to the 194 amino acid sequence. The N terminal methionine and/or signal peptide may be linked to a polypeptide that is 99% homologous to the 194 amino acid sequence or to a smaller fragment of a polypeptide that is 99% homologous to the 194 amino acid sequence. In calculating degrees of homology a polypeptide has to SEQ ID NO:4 or a fragment thereof, an N terminal methionine and/or any signal peptide is not included in such calculation. The sequences of the signal peptide are not used in determining homology. Thus, for example, although SEQ ID NO:12 comprises SEQ ID NO:4 operably linked to a signal peptide SEQ ID NO:17, SEQ ID NO:12 comprises a fragment of SEQ ID NO:4, that is 100% homologous to a fragment of SEQ ID NO:4, notwithstanding the signal peptide which is absent in SEQ ID NO:4. Thus, proteins which comprise fragments of a polypeptide that is at least 98% homologous to a fragment of SEQ ID NO:4 intended to refer to proteins which fragments of a polypeptide that is at least 98% homologous to a fragment of SEQ ID NO:4 that are at least 25 amino acids and may optionally be linked to a, for example, a signal peptide. SEQ ID NO:30 corresponds to an immunodominant T cell epitope of RSV M2-1 immunogen set forth in SEQ ID NO:4. SEQ ID NO:31 refers to a subdominant T cell epitope corresponds to an immunodominant T cell epitope of RSV M2-1 immunogen set forth in SEQ ID NO:4. In some embodiments, fragments comprise all or part of one or more of these sequences or sequences 98% or more or 99% or more homologous to them.

"Fragment" may also mean a nucleic acid fragment of that encodes an RSV Immunogen fragment set forth above, i.e. RSV F Immunogen, RSV M2-1 Immunogen, RSV Ga Immunogen, RSV Gb Immunogen, in each case with or without signal peptides and/or a methionine at position 1, proteins 98% or more homologous to the consensus sequences set forth herein, proteins 99% or more homologous to the consensus sequences set forth herein, and proteins 100% identical to the consensus sequences set forth herein, in each case with or without signal peptides and/or a methionine at position 1. A fragment may or may not for example comprise a fragments of nucleic acid sequences that encode an RSV Immunogen linked to coding sequence for an N terminal methionine (i.e. a start codon) or coding sequences encoding a signal peptide such as an immunoglobulin signal peptide for example IgE signal peptide (SEQ ID NO:17) or IgG signal peptide. A fragment of a coding sequence that encodes an RSV Immunogen may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of coding sequence of the particular full length RSV Immunogen sequence set forth herein, excluding any coding sequence that encodes non-RSV signal peptide added. Fragments also refer to fragments of coding sequences which encode a polypeptide that is 98% or more, or 99% or more homologous to the sequences of the RSV Immunogen set forth herein. The fragment may comprise a fragment of a polypeptide that is 98% or more homologous to and additionally comprise a signal peptide such as an immunoglobulin signal peptide which is not included when calculating percent homology.

In some embodiments, the fragments are fragments of a nucleic acid sequence 98% or more homologous to SEQ ID NO1. In some embodiments, the fragments are fragments of a nucleic acid sequence 99% or more homologous to SEQ ID NO:1. In some embodiments, the fragments are fragments of SEQ ID NO:1. It is intended that nucleic acid sequences encoding the polypeptide fragments described herein are expressly disclosed, i.e. fragments of nucleic acid sequences that encode the proteins having the size and homology of the peptide fragments. In some embodiments, fragments of nucleic acid sequences that encode the proteins having the size and homology of the peptide fragments are fragments of SEQ ID NO:1. A fragment of a coding sequence that encodes RSV F consensus Immunogen such as that which is disclosed in SEQ ID NO:2, SEQ ID NO:10, proteins 98% or more homologous to the RSV F consensus Immunogen sequences set forth herein, proteins 99% or more homologous to the RSV F consensus Immunogen sequences set forth herein, and RSV F consensus Immunogen 100% identical to the consensus sequences set forth herein, in each case with or without signal peptides and/or a methionine at position 1, such as for example SEQ ID NO:1 or SEQ ID NO:9, may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length RSV F consensus Immunogen sequence set forth herein, excluding any non-RSV signal peptide added. Fragments may encode fragments of a polypeptide that is 98% or more, or 99% or more homologous to the sequences of the RSV F consensus Immunogen set forth herein and 100% identical to such sequence, in each case with or without signal peptides and/or a methionine at position 1. The fragment may encode a fragment of a polypeptide that is 98% or more homologous, 99% or more homologous, or 100% identical to the RSV F consensus Immunogen and additionally comprise a signal peptide such as an immunoglobulin signal peptide which is not included when calculating percent homology. In some embodiments, a fragment that encodes RSV F Immunogen may encode a fragment of a SEQ ID NO:2 and comprise a fragment of SEQ ID NO:1. The fragment may encode fragments of SEQ ID NO:2 linked to a signal peptide such as an immunoglobulin signal peptide for example IgE signal peptide (SEQ ID NO:17) or IgG signal peptide. Thus in some embodiments, the fragment is a fragment of SEQ ID NO:10 which comprises SEQ ID NO:17 and may be encoded by SEQ ID NO:9. The fragment may comprise fragments of SEQ ID NO:1 linked to start codon. Fragments also encode fragments of a polypeptide that is 98% or more, or 99% or more homologous to SEQ ID NO:2. The fragment may encode a fragment of a polypeptide that is 98% or more homologous to SEQ ID NO:2 and additionally comprise a signal peptide such as an immunoglobulin signal peptide which is not included when calculating percent homology. The fragment may encode a fragment of a polypeptide that is 99% or more homologous to SEQ ID NO:2 and additionally comprise a signal peptide such as an immunoglobulin signal peptide which is not included when calculating percent homology.

The fragment may encode a fragment of a polypeptide that is 98% or more homologous to SEQ ID NO:2 and additionally comprise an N terminal methionine which is not included when calculating percent homology. The fragment may encode a fragment of a polypeptide that is 99% or more homologous to SEQ ID NO:2 and additionally comprise an N terminal methionine which is not included when calculating percent homology. Fragments may be 98% or more, or 99% or more homologous to SEQ ID NO:1. The fragment may be 98% or more homologous to SEQ ID NO:1 and additionally comprise a signal peptide such as an immunoglobulin signal peptide which is not included when calculating percent homology. The fragment may be 99% or more homologous to SEQ ID NO:1 and additionally comprise a signal peptide such as an immunoglobulin signal peptide which is not included when calculating percent homology. The fragment may be 98% or more homologous to SEQ ID NO:1 and additionally comprise an N terminal methionine which is not included when calculating percent homology. The fragment may be 99% or more homologous to SEQ ID NO:1 and additionally comprise an N terminal methionine which is not included when calculating percent homology. Fragments of SEQ ID NO:1, fragments of nucleic acid sequence 98% or more homologous to SEQ ID NO:1, and fragments of nucleic acid sequence 99% or more homologous to SEQ ID NO:1, in each case with or without start codons or coding sequences that encode signal peptides may encode fragments of RSV F immunogen that may be 115 or more amino acids in length, 163 or more, 230 or more, 288 or more, 345 or more, 403 or more, 460 or more, 515 or more, 520 or more, 525 or more, 530 or more, 535 or more, 540 or more, 545 or more, 550 or more, 555 or more, 560 or more, 565 or more, 570 or more, 574 or more in length. Polypeptide fragments may be fewer than 140 amino acids, fewer than 190, fewer than 250, fewer than 283, fewer than 300, fewer than 365, fewer than 425, fewer than 495, fewer than 518, fewer than 523, fewer than 528, fewer than 533, fewer than 547, fewer than 552, fewer than 563, or fewer than 572 in length. Fragments may further encode an N terminal methionine and/or a signal peptide such as an immunoglobulin signal peptide, for example an IgE or IgG signal peptide. The N terminal methionine and/or signal peptide may be linked to sequences that encode a 574 amino acid or smaller fragment thereof. The fragment may encode an N terminal methionine and/or signal peptide linked to a polypeptide that is 98% homologous to the 574 amino acid or to a smaller fragment of a polypeptide that is 98% homologous to the 574 amino acid sequence. The fragment may encode an N terminal methionine and/or signal peptide linked to a polypeptide that is 99% homologous to the 574 amino acid sequence or to a smaller fragment of a polypeptide that is 99% homologous to the 574 amino acid sequence. In calculating degrees of homology a polypeptide has to SEQ ID NO:2 or a fragment thereof, an N terminal methionine and/or any signal peptide is not included in such calculation. The sequences of the signal peptide are not used in determining homology. Thus, for example, although SEQ ID NO:7 comprises SEQ ID NO:1 operably linked to a coding sequences that encode signal peptide SEQ ID NO:17, SEQ ID NO:7 comprises a fragment of SEQ ID NO:1 that is 100% homologous to a fragment of SEQ ID NO:1, notwithstanding the signal peptide coding sequence which is absent in SEQ ID NO:1. SEQ ID NO:22, SEQ ID NO:23, SEQ ID NO:24, and SEQ ID NO:25 correspond to T cell epitopes of RSV F immunogen set forth in SEQ ID NO:2. In some embodiments, fragments comprise coding sequences that encode all or part of one or more of these sequences or sequences 98% or more or 99% or more homologous to them including fragments of SEQ ID NO:1 or sequences that are 98% or more or 99% or more homologous to SEQ ID NO:1.

In some embodiments, the fragments are fragments of a nucleic acid sequence 98% or more homologous to SEQ ID NO:5. In some embodiments, the fragments are fragments of a nucleic acid sequence 99% or more homologous to SEQ ID NO:5. In some embodiments, the fragments are fragments of SEQ ID NO:5. It is intended that nucleic acid sequences encoding the polypeptide fragments described herein are expressly disclosed, i.e. fragments of nucleic acid sequences that encode the proteins having the size and homology of the peptide fragments. In some embodiments, fragments of nucleic acid sequences that encode the proteins having the size and homology of the peptide fragments are fragments of SEQ ID NO:5. A fragment of a coding sequence that encodes RSV Ga consensus Immunogen such as that which is disclosed in SEQ ID NO:6, SEQ ID NO:14, proteins 98% or more homologous to the RSV Ga consensus Immunogen sequences set forth herein, proteins 99% or more homologous to the RSV Ga consensus Immunogen sequences set forth herein, and RSV Ga consensus Immunogen 100% identical to the consensus sequences set forth herein, in each case with or without signal peptides and/or a methionine at position 1, such as for example SEQ ID NO:5 or SEQ ID NO:13, may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length RSV Ga consensus Immunogen sequence set forth herein, excluding any non-RSV signal peptide added. Fragments may encode fragments of a polypeptide that is 98% or more, or 99% or more homologous to the sequences of the RSV Ga consensus Immunogen set forth herein and 100% identical to such sequence, in each case with or without signal peptides and/or a methionine at position 1. The fragment may encode a fragment of a polypeptide that is 98% or more homologous, 99% or more homologous, or 100% identical to the RSV Ga consensus Immunogen and additionally comprise a signal peptide such as an immunoglobulin signal peptide which is not included when calculating percent homology. In some embodiments, a fragment that encodes RSV Ga Immunogen may encode a fragment of a SEQ ID NO:6 and comprise a fragment of SEQ ID NO:5. The fragment may encode fragments of SEQ ID NO:6 linked to a signal peptide such as an immunoglobulin signal peptide for example IgE signal peptide (SEQ ID NO:17) or IgG signal peptide. Thus in some embodiments, the fragment is a fragment of SEQ ID NO:14 which comprises SEQ ID NO:17 and may be encoded by SEQ ID NO:13. The fragment may comprise fragments of SEQ ID NO:5 linked to start codon. Fragments also encode fragments of a polypeptide that is 98% or more, or 99% or more homologous to SEQ ID NO:6. The fragment may encode a fragment of a polypeptide that is 98% or more homologous to SEQ ID NO:6 and additionally comprise a signal peptide such as an immunoglobulin signal peptide which is not included when calculating percent homology. The fragment may encode a fragment of a polypeptide that is 99% or more homologous to SEQ ID NO:6 and additionally comprise a signal peptide such as an immunoglobulin signal peptide which is not included when calculating percent homology. The fragment may encode a fragment of a polypeptide that is 98% or more homologous to SEQ ID NO:6 and additionally comprise an N terminal methionine which is not included when calculating percent homology. The fragment may encode a fragment of a polypeptide that is 99% or more homologous to SEQ ID NO:6 and additionally comprise an N terminal methionine which is not included when calculating percent homology. Fragments may be 98% or more, or 99% or more homologous to SEQ ID NO:5. The fragment may be 98% or more homologous to SEQ ID NO:5 and additionally comprise a signal peptide such as an immunoglobulin signal peptide which is not included when calculating percent homology. The fragment may be 99% or more homologous to SEQ ID NO:5 and additionally comprise a signal peptide such as an immunoglobulin signal peptide which is not included when calculating percent homology. The fragment may be 98% or more homologous to SEQ ID NO:5 and additionally comprise an N terminal methionine which is not included when calculating percent homology. The fragment may be 99% or more homologous to SEQ ID NO:5 and additionally comprise an N terminal methionine which is not included when calculating percent homology. Fragments of SEQ ID NO:5, fragments of nucleic acid sequence 98% or more homologous to SEQ ID NO:5, and fragments of nucleic acid sequence 99% or more homologous to SEQ ID NO:5, in each case with or without start codons or coding sequences that encode signal peptides may encode fragments of RSV Ga immunogen that may be In some embodiments, the fragments thereof may be 125 or more amino acids in length, 130 or more, 140 or more, 150 or more, 160 or more, 170 or more, 180 or more, 190 or more, 200 or more, 210 or more, 220 or more, 230 or more, 240 or more, 250 or more, 260 or more, 270 or more, 280 or more, 285 or more, 290 or more, 295 or more in length. Polypeptide fragments may be fewer than 135 amino acids, fewer than 145, fewer than 155, fewer than 165, fewer than 175, fewer than 185, fewer than 195, fewer than 205, fewer than 215, fewer than 225, fewer than 235, fewer than 245, fewer than 255, fewer than 265, fewer than 275, fewer than 285, fewer than 288, fewer than 292, or fewer than 296 in length. Fragments may further encode an N terminal methionine and/or a signal peptide such as an immunoglobulin signal peptide, for example an IgE or IgG signal peptide. The N terminal methionine and/or signal peptide may be linked to sequences that encode a 296 amino acid or smaller fragment thereof. The fragment may encode an N terminal methionine and/or signal peptide linked to a polypeptide that is 98% homologous to the 296 amino acid or to a smaller fragment of a polypeptide that is 98% homologous to the 296 amino acid sequence. The fragment may encode an N terminal methionine and/or signal peptide linked to a polypeptide that is 99% homologous to the 296 amino acid sequence or to a smaller fragment of a polypeptide that is 99% homologous to the 296 amino acid sequence. In calculating degrees of homology a polypeptide has to SEQ ID NO:6 or a fragment thereof, an N terminal methionine and/or any signal peptide is not included in such calculation. The sequences of the signal peptide are not used in determining homology. Thus, for example, although SEQ ID NO:13 comprises SEQ ID NO:5 operably linked to a coding sequences that encode signal peptide SEQ ID NO:17, SEQ ID NO:13 comprises a fragment of SEQ ID NO:5 that is 100% homologous to a fragment of SEQ ID NO:5, notwithstanding the signal peptide coding sequence which is absent in SEQ ID NO:5.

In some embodiments, the fragments are fragments of a nucleic acid sequence 98% or more homologous to SEQ ID NO:7. In some embodiments, the fragments are fragments of a nucleic acid sequence 99% or more homologous to SEQ ID NO:7. In some embodiments, the fragments are fragments of SEQ ID NO:7. It is intended that nucleic acid sequences encoding the polypeptide fragments described herein are expressly disclosed, i.e. fragments of nucleic acid sequences that encode the proteins having the size and homology of the peptide fragments. In some embodiments, fragments of nucleic acid sequences that encode the proteins having the size and homology of the peptide fragments are fragments of SEQ ID NO:7. A fragment of a coding sequence that encodes RSV Gb consensus Immunogen such as that which is disclosed in SEQ ID NO:8, SEQ ID NO:16, proteins 98% or more homologous to the RSV Gb consensus Immunogen sequences set forth herein, proteins 99% or more homologous to the RSV Gb consensus Immunogen sequences set forth herein, and RSV Gb consensus Immunogen 100% identical to the consensus sequences set forth herein, in each case with or without signal peptides and/or a methionine at position 1, such as for example SEQ ID NO:7 or SEQ ID NO:15, may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length RSV Gb consensus Immunogen sequence set forth herein, excluding any non-RSV signal, peptide added. Fragments may encode fragments of a polypeptide that is 98% or more, or 99% or more homologous to the sequences of the RSV Gb consensus Immunogen set forth herein and 100% identical to such sequence, in each case with or without signal peptides and/or a methionine at position 1. The fragment may encode a fragment of a polypeptide that is 98% or more homologous, 99% or more homologous, or 100% identical to the RSV Gb consensus Immunogen and additionally comprise a signal peptide such as an immunoglobulin signal peptide which is not included when calculating percent homology. In some embodiments, a fragment that encodes RSV Gb Immunogen may encode a fragment of a SEQ ID NO:8 and comprise a fragment of SEQ ID NO:7. The fragment may encode fragments of SEQ ID NO:8 linked to a signal peptide such as an immunoglobulin signal peptide for example IgE signal peptide (SEQ ID NO:17) or IgG signal peptide. Thus in some embodiments, the fragment is a fragment of SEQ ID NO:16 which comprises SEQ ID NO:17 and may be encoded by SEQ ID NO:15. The fragment may comprise fragments of SEQ ID NO:7 linked to start codon. Fragments also encode fragments of a polypeptide that is 98% or more, or 99% or more homologous to SEQ ID NO:8. The fragment may encode a fragment of a polypeptide that is 98% or more homologous to SEQ ID NO:8 and additionally comprise a signal peptide such as an immunoglobulin signal peptide which is not included when calculating percent homology. The fragment may encode a fragment of a polypeptide that is 99% or more homologous to SEQ ID NO:8 and additionally comprise a signal peptide such as an immunoglobulin signal peptide which is not included when calculating percent homology. The fragment may encode a fragment of a polypeptide that is 98% or more homologous to SEQ ID NO:8 and additionally comprise an N terminal methionine which is not included when calculating percent homology. The fragment may encode a fragment of a polypeptide that is 99% or more homologous to SEQ ID NO:8 and additionally comprise an N terminal methionine which is not included when calculating percent homology. Fragments may be 98% or more, or 99% or more homologous to SEQ ID NO:7. The fragment may be 98% or more homologous to SEQ ID NO:7 and additionally comprise a signal peptide such as an immunoglobulin signal peptide which is not included when calculating percent homology. The fragment may be 99% or more homologous to SEQ ID NO:7 and additionally comprise a signal peptide such as an immunoglobulin signal peptide which is not included when calculating percent homology. The fragment may be 98% or more homologous to SEQ ID NO:7 and additionally comprise an N terminal methionine which is not included when calculating percent homology. The fragment may be 99% or more homologous to SEQ ID NO:7 and additionally comprise an N terminal methionine which is not included when calculating percent homology. Fragments of SEQ ID NO:7, fragments of nucleic acid sequence 98% or more homologous to SEQ ID NO:7, and fragments of nucleic acid sequence 99% or more homologous to SEQ ID NO:7, in each case with or without start codons or coding sequences that encode signal peptides may encode fragments of RSV Gb immunogen that may be In some embodiments, the fragments thereof may be 125 or more amino acids in length, 130 or more, 140 or more, 150 or more, 160 or more, 170 or more, 180 or more, 190 or more, 200 or more, 210 or more, 220 or more, 230 or more, 240 or more, 250 or more, 260 or more, 270 or more, 280 or more, 285 or more, 288 or more in length. Polypeptide fragments may be fewer than 135 amino acids, fewer than 145, fewer than 155, fewer than 165, fewer than 175, fewer than 185, fewer than 195, fewer than 205, fewer than 215, fewer than 225, fewer than 235, fewer than 245, fewer than 255, fewer than 265, fewer than 275, fewer than 285, fewer than 288, fewer than 290 in length. Fragments may further encode an N terminal methionine and/or a signal peptide such as an immunoglobulin signal peptide, for example an IgE or IgG signal peptide. The N terminal methionine and/or signal peptide may be linked to sequences that encode a 290 amino acid or smaller fragment thereof. The fragment may encode an N terminal methionine and/or signal peptide linked to a polypeptide that is 98% homologous to the 290 amino acid or to a smaller fragment of a polypeptide that is 98% homologous to the 290 amino acid sequence. The fragment may encode an N terminal methionine and/or signal peptide linked to a polypeptide that is 99% homologous to the 290 amino acid sequence or to a smaller fragment of a polypeptide that is 99% homologous to the 290 amino acid sequence. In calculating degrees of homology a polypeptide has to SEQ ID NO:8 or a fragment thereof, an N terminal methionine and/or any signal peptide is not included in such calculation. The sequences of the signal peptide are not used in determining homology. Thus, for example, although SEQ ID NO:15 comprises SEQ ID NO:7 operably linked to a coding sequences that encode signal peptide SEQ ID NO:17, SEQ ID NO:15 comprises a fragment of SEQ ID NO:7 that is 100% homologous to a fragment of SEQ ID NO:7, notwithstanding the signal peptide coding sequence which is absent in SEQ ID NO:7.

Also provides are sequences related to RSV M2-1 including fragments of a nucleic acid sequence 98% or more homologous to SEQ ID NO:3. In some embodiments, the fragments are fragments of a nucleic acid sequence 99% or more homologous to SEQ ID NO:3. In some embodiments, the fragments are fragments of SEQ ID NO:3. It is intended that nucleic acid sequences encoding the polypeptide fragments described herein are expressly disclosed, i.e. fragments of nucleic acid sequences that encode the proteins having the size and homology of the peptide fragments. In some embodiments, fragments of nucleic acid sequences that encode the proteins having the size and homology of the peptide fragments am fragments of SEQ ID NO:3. A fragment of a coding sequence that encodes RSV M2-1 consensus Immunogen such as that which is disclosed in SEQ ID NO:4, SEQ ID NO:12, proteins 98% or more homologous to the RSV M2-1 consensus Immunogen sequences set forth herein, proteins 99% or more homologous to the RSV M2-1 consensus Immunogen sequences set forth herein, and RSV M2-1 consensus Immunogen 100% identical to the consensus sequences set forth herein, in each case with or without signal peptides and/or a methionine at position 1, such as for example SEQ ID NO:3 or SEQ ID NO:11, may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length RSV M2-1 consensus Immunogen sequence set forth herein, excluding any non-RSV signal peptide added. Fragments may encode fragments of a polypeptide that is 98% or more, or 99% or more homologous to the sequences of the RSV M2-1 consensus Immunogen set forth herein and 100% identical to such sequence, in each case with or without signal peptides and/or a methionine at position 1. The fragment may encode a fragment of a polypeptide that is 98% or more homologous, 99% or more homologous, or 100% identical to the RSV M2-1 consensus Immunogen and additionally comprise a signal peptide such as an immunoglobulin signal peptide which is not included when calculating percent homology. In some embodiments, a fragment that encodes RSV M2-1 Immunogen may encode a fragment of a SEQ ID NO:4 and comprise a fragment of SEQ ID NO:3. The fragment may encode fragments of SEQ ID NO:4 linked to a signal peptide such as an immunoglobulin signal peptide for example IgE signal peptide (SEQ ID NO:17) or IgG signal peptide. Thus in some embodiments, the fragment is a fragment of SEQ ID NO:12 which comprises SEQ ID NO:17 and may be encoded by SEQ ID NO:11. The fragment may comprise fragments of SEQ ID NO:3 linked to start codon. Fragments also encode fragments of a polypeptide that is 98% or more, or 99% or more homologous to SEQ ID NO:4. The fragment may encode a fragment of a polypeptide that is 98% or more homologous to SEQ ID NO:4 and additionally comprise a signal peptide such as an immunoglobulin signal peptide which is not included when calculating percent homology. The fragment may encode a fragment of a polypeptide that is 99% or more homologous to SEQ ID NO:4 and additionally comprise a signal peptide such as an immunoglobulin signal peptide which is not included when calculating percent homology. The fragment may encode a fragment of a polypeptide that is 98% or more homologous to SEQ ID NO:4 and additionally comprise an N terminal methionine which is not included when calculating percent homology. The fragment may encode a fragment of a polypeptide that is 99% or more homologous to SEQ ID NO:4 and additionally comprise an N terminal methionine which is not included when calculating percent homology. Fragments may be 98% or more, or 99% or more homologous to SEQ ID NO:3. The fragment may be 98% or more homologous to SEQ ID NO:3 and additionally comprise a signal peptide such as an immunoglobulin signal peptide which is not included when calculating percent homology. The fragment may be 99% or more homologous to SEQ ID NO:3 and additionally comprise a signal peptide such as an immunoglobulin signal peptide which is not included when calculating percent homology. The fragment may be 98% or more homologous to SEQ ID NO:3 and additionally comprise an N terminal methionine which is not included when calculating percent homology. The fragment may be 99% or more homologous to SEQ ID NO:3 and additionally comprise an N terminal methionine which is not included when calculating percent homology. Fragments of SEQ ID NO:3, fragments of nucleic acid sequence 98% or more homologous to SEQ ID NO:3, and fragments of nucleic acid sequence 99% or more homologous to SEQ ID NO:3, in each case with or without start codons or coding sequences that encode signal peptides may encode fragments of RSV M2-1 immunogen that may be In some embodiments, the fragments thereof may be 25 or more amino acids in length, 30 or more, 40 or more, 50 or more, 60 or more, 70 or more, 80 or more, 90 or more, 100 or more, 110 or more, 120 or more, 130 or more, 140 or more, 150 or more, 160 or more, 170 or more, 180 or more, 184 or more, 190 or more, 193 or more in length. Polypeptide fragments may be fewer than 35 amino acids, fewer than 45, fewer than 55, fewer than 65, fewer than 75, fewer than 85, fewer than 95, fewer than 105, fewer than 115, fewer than 125, fewer than 135, fewer than 145, fewer than 155, fewer than 165, fewer than 175, fewer than 185, fewer than 188, fewer than 192, or fewer than 194 in length. Fragments may further encode an N terminal methionine and/or a signal peptide such as an immunoglobulin signal peptide, for example an IgE or IgG signal peptide. The N terminal methionine and/or signal peptide may be linked to sequences that encode a 194 amino acid or smaller fragment thereof. The fragment may encode an N terminal methionine and/or signal peptide linked to a polypeptide that is 98% homologous to the 194 amino acid or to a smaller fragment of a polypeptide that is 98% homologous to the 194 amino acid sequence. The fragment may encode an N terminal methionine and/or signal peptide linked to a polypeptide that is 99% homologous to the 194 amino acid sequence or to a smaller fragment of a polypeptide that is 99% homologous to the 194 amino acid sequence. In calculating degrees of homology a polypeptide has to SEQ ID NO:4 or a fragment thereof, an N terminal methionine and/or any signal peptide is not included in such calculation. The sequences of the signal peptide are not used in determining homology. Thus, for example, although SEQ ID NO:9 comprises SEQ ID NO:3 operably linked to a coding sequences that encode signal peptide SEQ ID NO:17, SEQ ID NO:9 comprises a fragment of SEQ ID NO:3 that is 100% homologous to a fragment of SEQ ID NO:3, notwithstanding the signal peptide coding sequence which is absent in SEQ ID NO:3. SEQ ID NO:30 corresponds to an immunodominant T cell epitope of RSV M2-1 immunogen set forth in SEQ ID NO:4. SEQ ID NO:31 refers to a subdominant T cell epitope corresponds to an immunodominant T cell epitope of RSV M2-1 immunogen set forth in SEQ ID NO:4. In some embodiments, fragments comprise coding sequences that encode all or part of one or more of these sequences or sequences 98% or more or 99% or more homologous to them including fragments of SEQ ID NO:3 or sequences that are 98% or more or 99% or more homologous to SEQ ID NO:3.

l. Identical

"Identical" or "identity" as used herein in the context of two or more nucleic acids or polypeptide sequences, may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

m. Impedance

"Impedance" as used herein may be used when discussing the feedback mechanism and can be converted to a current value according to Ohm's law, thus enabling comparisons with the preset current.

n. Immune Response

"Immune response" as used herein may mean the activation of a host's immune system, e.g., that of a mammal, in response to the introduction of one or more RSV consensus antigen via the provided DNA plasmid vaccines. The immune response can be in the form of a cellular or humoral response, or both.

o. Nucleic Acid

"Nucleic acid" or "oligonucleotide" or "polynucleotide" as used herein may mean at least two nucleotides covalently linked together. The depiction of a single strand also defines the sequence of the complementary strand. Thus, a nucleic acid also encompasses the complementary strand of a depicted single strand. Many variants of a nucleic acid may be used for the same purpose as a given nucleic acid. Thus, a nucleic acid also encompasses substantially identical nucleic acids and complements thereof. A single strand provides a probe that may hybridize to a target sequence under stringent hybridization conditions. Thus, a nucleic acid also encompasses a probe that hybridizes under stringent hybridization conditions.

Nucleic acids may be single stranded or double stranded, or may contain portions of both double stranded and single stranded sequence. The nucleic acid may be DNA, both genomic and cDNA, RNA, or a hybrid, where the nucleic acid may contain combinations of deoxyribo- and ribonucleotides, and combinations of bases including uracil, adenine, thymine, cytosine, guanine, inosine, xanthine hypoxanthine, isocytosine and isoguanine. Nucleic acids may be obtained by chemical synthesis methods or by recombinant methods.

p. Operably Linked

"Operably linked" as used herein may mean that expression of a gene is under the control of a promoter with which it is spatially connected. A promoter may be positioned 5' (upstream) or 3' (downstream) of a gene under its control. The distance between the promoter and a gene may be approximately the same as the distance between that promoter and the gene it controls in the gene from which the promoter is derived. As is known in the art, variation in this distance may be accommodated without loss of promoter function.

q. Promoter

"Promoter" as used herein may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. A promoter may be derived from sources including viral, bacterial, fungal, plants, insects, and animals. A promoter may regulate the expression of a gene component constitutively, or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter and the CMV IE promoter.

r. Stringent Hybridization Conditions

"Stringent hybridization conditions" as used herein may mean conditions under which a first nucleic acid sequence (e.g., probe) will hybridize to a second nucleic acid sequence (e.g., target), such as in a complex mixture of nucleic acids. Stringent conditions are sequence-dependent and will be different in different circumstances. Stringent conditions may be selected to be about 5-10° C. lower than the thermal melting point ($T_m$) for the specific sequence at a defined ionic strength pH. The $T_m$ may be the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may be those in which the salt concentration is less than about 1.0M sodium ion, such as about 0.01-1.0M sodium ion concentration (or other salts) at pH 7.0 to 8.3 and the temperature is at least about 30° C. for short probes (e.g., about 10-50 nucleotides) and at least about 60° C. for long probes (e.g., greater than about 50 nucleotides). Stringent conditions may also be achieved with the addition of destabilizing agents such as formamide. For selective or specific hybridization, a positive signal may be at least 2 to 10 times background hybridization. Exemplary stringent hybridization conditions include the following: 50% formamide, 5×SSC, and 1% SDS, incubating at 42° C., or, 5×SSC, 1% SDS, incubating at 65° C., with wash in 0.2×SSC, and 0.1% SDS at 65° C.

s. Substantially Complementary

"Substantially complementary" as used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or that the two sequences hybridize under stringent hybridization conditions.

t. Substantially Identical

"Substantially identical" as used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

u. Variant

"Variant" used herein with respect to a nucleic acid may mean (i) a portion or fragment of a referenced nucleotide sequence; (ii) the complement of a referenced nucleotide sequence or portion thereof; (iii) a nucleic acid that is substantially identical to a referenced nucleic acid or the complement thereof; or (iv) a nucleic acid that hybridizes under stringent conditions to the referenced nucleic acid, complement thereof, or a sequences substantially identical thereto.

"Variant" with respect to a peptide or polypeptide that differs in amino acid sequence by the insertion, deletion, or conservative substitution of amino acids, but retain at least one biological activity. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

v. Vector

"Vector" used herein may mean a nucleic acid sequence containing an origin of replication. A vector may be a plasmid, bacteriophage, bacterial artificial chromosome or yeast artificial chromosome. A vector may be a DNA or RNA vector. A vector may be either a self-replicating extrachromosomal vector or a vector which integrates into a host genome.

2. RSV Proteins

Provided herein are RSV proteins, also referred to herein as "RSV immunogens", are consensus antigens capable of eliciting an immune response against RSV. Three of the consensus RSV immunogens are: RSV F immunogen, and two forms of RSV G immunogen, referred to herein as RSV Ga immunogen and RSV Gb immunogen. Two RSV G immunogen forms are provided due to the diversity among RSV G proteins. In some embodiments, the RSV immunogens may comprise a signal peptide from a different protein such as an immunoglobulin protein, for example an IgE signal peptide (SEQ ID NO:17) or an IgG signal peptide. RSV immunogen include RSV F immunogen, RSV Ga immunogen and RSV Gb immunogen. Also provided herein is the "RSV immunogens" that is a consensus antigens capable of eliciting an immune response against RSV M2-1, i.e. RSV M2-1 immunogen which may optionally comprise a signal peptide from a different protein such as an immunoglobulin protein, for example an IgE signal peptide (SEQ ID NO:17) or an IgG signal peptide.

"RSV F immunogens" refer to proteins comprising immunogenic fragments of proteins that are at least 98% homologous to SEQ ID NO:2. The RSV F immunogen may comprise immunogenic fragments of proteins that are at least 99% homologous to SEQ ID NO:2. The RSV F immunogen may comprise immunogenic fragments of SEQ ID NO:2. In each instance the immunogenic fragments may optionally further comprise a signal peptide such as SEQ ID NO:17. The RSV F immunogen that comprises an immunogenic fragment of SEQ ID NO:2 and signal peptide SEQ ID NO:17 may be an immunogenic fragments of SEQ ID NO:10 that comprises SEQ ID NO:17. RSV F immunogen may comprise a protein that is at least 98% homologous to SEQ ID NO:2, and in some embodiments may comprise a protein that is at least 99% homologous to SEQ ID NO:2. The RSV F immunogen may comprise SEQ ID NO:2. In each instance the RSV F immunogen may optionally further comprise a signal peptide such as SEQ ID NO:17. The RSV F immunogen that comprises SEQ ID NO:2 and signal peptide SEQ ID NO:17 may comprise SEQ ID NO:10.

"RSV Ga immunogens" refer to proteins comprising immunogenic fragments of proteins that are at least 98% homologous to SEQ ID NO:6. The RSV Ga immunogen may comprise immunogenic fragments of proteins that are at least 99% homologous to SEQ ID NO:6. The RSV Ga immunogen may comprise immunogenic fragments of SEQ ID NO:6. In each instance the immunogenic fragments may optionally further comprise a signal peptide such as SEQ ID NO:17. The RSV Ga immunogen that comprises an immunogenic fragment of SEQ ID NO:6 and signal peptide SEQ ID NO:17 may be an immunogenic fragments of SEQ ID NO:14 that comprises SEQ ID NO:17. RSV Ga immunogen may comprise a protein that is at least 98% homologous to SEQ ID NO:6, and in some embodiments may comprise a protein that is at least 99% homologous to SEQ ID NO:6. The RSV Ga immunogen may comprise SEQ ID NO:6. In each instance the RSV Ga immunogen may optionally further comprise a signal peptide such as SEQ ID NO:17. The RSV Ga immunogen that comprises SEQ ID NO:6 and signal peptide SEQ ID NO:17 may comprise SEQ ID NO:14.

"RSV Gb immunogens" refer to proteins comprising immunogenic fragments of proteins that are at least 98% homologous to SEQ ID NO:8. The RSV Gb immunogen may comprise immunogenic fragments of proteins that are at least 99% homologous to SEQ ID NO:8. The RSV Gb immunogen may comprise immunogenic fragments of SEQ ID NO:8. In each instance the immunogenic fragments may optionally further comprise a signal peptide such as SEQ ID NO:17. The RSV Gb immunogen that comprises an immunogenic fragment of SEQ ID NO:8 and signal peptide SEQ ID NO:17 may be an immunogenic fragments of SEQ ID NO:16 that comprises SEQ ID NO:17. RSV Gb immunogen may comprise a protein that is at least 98% homologous to SEQ ID NO:8, and in some embodiments may comprise a protein that is at least 99% homologous to SEQ ID NO:8. The RSV Gb immunogen may comprise SEQ ID NO:8. In each instance the RSV Gb immunogen may optionally further comprise a signal peptide such as SEQ ID NO:17. The RSV Gb immunogen that comprises SEQ ID NO:8 and signal peptide SEQ ID NO:17 may comprise SEQ ID NO:16.

In some embodiments, fusion proteins are provided which comprise a combination of two or more of the RSV proteins set forth herein. For example, fusion proteins may comprise: SEQ ID NO:2 or an immunogenic fragment thereof and SEQ ID NO:6 or an immunogenic fragment thereof; SEQ ID NO:2 or an immunogenic fragment thereof and SEQ ID NO:8 or an immunogenic fragment thereof; or SEQ ID NO:6 or an immunogenic fragment thereof and SEQ ID NO:8 or an immunogenic fragment thereof. Fusion proteins may comprise: SEQ ID NO:2 or an immunogenic fragment thereof, SEQ ID NO:6 or an immunogenic fragment thereof and SEQ ID NO:8 or an immunogenic fragment thereof. Alternatively one or more of the fusion proteins above may comprise a sequence at least 98% or at least 99% homologous to SEQ ID NO:2 or an immunogenic fragment thereof in place of the portion of the fusion protein described above corresponding to SEQ ID NO:2 or an immunogenic fragment. Likewise, one or more of the fusion proteins above may comprise a sequence at least 98% or at least 99% homologous to SEQ ID NO:6 or an immunogenic fragment thereof in place of the portion of the fusion protein described above corresponding to SEQ ID NO:6 or an immunogenic fragment; and/or one or more of the fusion proteins above may comprise a sequence at least 98% or at least 99% homologous to SEQ ID NO:8 or an immunogenic fragment thereof in place of the portion of the fusion protein described above corresponding to SEQ ID NO:8 or an immunogenic fragment. Fusion proteins may include combinations of consensus proteins and/or fragments of consensus protein and/or variants of consensus protein and/or fragments of variants consensus proteins. The consensus proteins and/or fragments of consensus protein and/or variants of consensus protein and/or fragments of variants consensus proteins may be linked directly adjacent to each other or linked with a spacer or one more amino acids in between. In some embodiments, the space may be a proteolytic cleavage site. In some embodiments, the space may be a proteolytic cleavage site recognized by a protease found in cells to which the vaccine is intended to be administered and/or taken up.

"RSV M2-1 immunogens" refer to proteins comprising immunogenic fragments of proteins that are at least 98% homologous to SEQ ID NO:4. The RSV M2-1 immunogen may comprise immunogenic fragments of proteins that are at least 99% homologous to SEQ ID NO:4. The RSV M2-1 immunogen may comprise immunogenic fragments of SEQ ID NO:4. In each instance the immunogenic fragments may optionally further comprise a signal peptide such as SEQ ID NO:17. The RSV M2-1 immunogen that comprises an immunogenic fragment of SEQ ID NO:4 and signal peptide SEQ ID NO:17 may be an immunogenic fragments of SEQ ID NO:12 that comprises SEQ ID NO:17. RSV M2-1 immunogen may comprise a protein that is at least 98% homologous to SEQ ID NO:4, and in some embodiments may comprise a protein that is at least 99% homologous to SEQ ID NO:4. The RSV M2-1 immunogen may comprise SEQ ID NO:4. In each instance the RSV M2-1 immunogen may optionally further comprise a signal peptide such as SEQ ID NO:17. The RSV M2-1 immunogen that comprises SEQ ID NO:4 and signal peptide SEQ ID NO:17 may comprise SEQ ID NO:12. In some embodiments, fusion proteins are provided which comprise a combination of RSV M2-1 and another RSV immunogen proteins set forth herein. For example, fusion proteins may comprise: SEQ ID NO:2 or an immunogenic fragment thereof and SEQ ID NO:4 or an immunogenic fragment thereof; SEQ ID NO:4 or an immunogenic fragment thereof and SEQ ID NO:6 or an immunogenic fragment thereof, SEQ ID NO:4 or an immunogenic fragment thereof and SEQ ID NO:8 or an immunogenic fragment thereof; or SEQ ID NO:6 or an immunogenic fragment thereof and SEQ ID NO:8 or an immunogenic fragment thereof. Fusion proteins may comprise: SEQ ID NO:4 or an immunogenic fragment thereof. Alternatively one or more of the fusion proteins above may comprise a sequence at least 98% or at least 99% homologous to SEQ ID NO:4 or an immunogenic fragment thereof in place of the portion of the fusion protein described above corresponding to SEQ ID NO:4 or an immunogenic fragment.

3. Coding Sequences Encoding RSV Proteins

Provided herein are nucleic acid sequences that encode the "RSV immunogens" set forth herein. Administration of nucleic acid molecules comprising the nucleic acid sequences when taken up and expressed by cells results in a broad immune response against RSV. Coding sequences for RSV immunogens are provided, i.e. nucleic acid sequences that encode RSV F immunogen, nucleic acid sequences that encode RSV Ga immunogen and nucleic acid sequences that encode RSV Gb immunogen as well as for nucleic acid sequences that encode RSV M2-1 immunogen. In some embodiments, the nucleic acid sequences that encode RSV immunogens may comprise nucleic acid sequences that encode a signal peptide from a different protein such as an immunoglobulin protein, for example an IgE signal peptide (SEQ ID NO:17) or an IgG signal peptide.

Nucleic acid sequences that encode RSV F immunogens may encode proteins comprising immunogenic fragments of proteins that are at least 98% homologous to SEQ ID NO:2. Nucleic acid sequences that encode RSV F immunogens may encode proteins that comprise immunogenic fragments of proteins that are at least 99% homologous to SEQ ID NO:2. Nucleic acid sequences that encode RSV F immunogens may encode proteins that comprise immunogenic fragments of SEQ ID NO:2. In each instance the nucleic acid sequences that encode proteins that comprise the immunogenic fragments may optionally further comprise nucleic acid sequences that encode a signal peptide such as nucleic acid sequences that encode SEQ ID NO:17. Nucleic acid sequences that encode RSV F immunogens may encode proteins that comprises an immunogenic fragment of SEQ ID NO:2 and signal peptide SEQ ID NO:17. Nucleic acid sequences that encode RSV F immunogens may encode proteins that may be an immunogenic fragment of SEQ ID NO:10 that comprises SEQ ID NO:17. Nucleic acid sequences that encode RSV F immunogens may encode proteins that comprise a protein that is at least 98% homologous to SEQ ID NO:2, and in some embodiments may encode a protein that is at least 99% homologous to SEQ ID NO:2. Nucleic acid sequences that encode RSV F immunogens may encode proteins that comprise SEQ ID NO:2. In each instance nucleic acid sequences that encode RSV F immunogens may optionally further comprise nucleic acid sequences that encode a signal peptide such as SEQ ID NO:17. Nucleic acid sequences that encode RSV F immunogens may encode a protein that comprises SEQ ID NO:2 and signal peptide SEQ ID NO:17. Nucleic acid sequences that encode RSV F immunogens may encode a protein that comprises SEQ ID NO:10.

Nucleic acid sequences that encode RSV F immunogens may comprise fragments of a nucleic acid sequence that is at least 98% homologous to SEQ ID NO:1. The nucleic acid sequence that is at least 98% homologous to SEQ ID NO:1 encodes a protein that is at least 98% homologous to SEQ ID NO:2. The fragment encodes an immunogenic fragment of the protein that is at least 98% homologous to SEQ ID NO:2. In some embodiments, the nucleic acid sequences that encodes the RSV F immunogen may comprise fragments of a nucleic acid sequence that is at least 98% homologous to SEQ ID NO:1 wherein the nucleic acid sequence encodes a protein that is at least 99% homologous to SEQ ID NO:2, in some embodiments nucleic acid sequence encodes a protein that comprises SEQ ID NO:2, and the fragment of the nucleic acid sequence encodes an immunogenic fragment of the protein that is at least 99% homologous to SEQ ID NO:2 such as an immunogenic fragment SEQ ID NO:2. In some such embodiments, the nucleic acid sequences that encodes the RSV F immunogen may comprise fragments of a nucleic acid sequence that is at least 99% homologous to SEQ ID NO:1 and in some embodiments, fragments of SEQ ID NO:1. In some embodiments, the nucleic acid sequences that encode RSV F immunogens may optionally further comprise nucleic acid sequences that encode a signal peptide such as SEQ ID NO:17. Nucleic acid sequences that encode RSV F immunogens may comprise fragments of SEQ ID NO:2 and coding sequence encoding signal peptide SEQ ID NO:17. Nucleic acid sequences that encode RSV F immunogens may comprise fragments of SEQ ID NO:9 that include coding sequence encoding signal peptide SEQ ID NO:17.

Nucleic acid sequences that encode RSV Ga immunogens may encode proteins comprising immunogenic fragments of proteins that are at least 98% homologous to SEQ ID NO:6. Nucleic acid sequences that encode RSV Ga immunogens may encode proteins that comprise immunogenic fragments of proteins that are at least 99% homologous to SEQ ID NO:6. Nucleic acid sequences that encode RSV Ga immunogens may encode proteins that comprise immunogenic fragments of SEQ ID NO:6. In each instance the nucleic acid sequences that encode proteins that comprise the immunogenic fragments may optionally further comprise nucleic acid sequences that encode a signal peptide such as nucleic acid sequences that encode SEQ ID NO:17. Nucleic acid sequences that encode RSV Ga immunogens may encode proteins that comprises an immunogenic fragment of SEQ ID NO:6 and signal peptide SEQ ID NO:17. Nucleic acid sequences that encode RSV Ga immunogens may encode proteins that may be an immunogenic fragment of SEQ ID NO:14 that comprises SEQ ID NO:17. Nucleic acid sequences that encode RSV Ga immunogens may encode proteins that comprise a protein that is at least 98% homologous to SEQ ID NO:6, and in some embodiments may encode a protein that is at least 99% homologous to SEQ ID NO:6. Nucleic acid sequences that encode RSV Ga immunogens may encode proteins that comprise SEQ ID NO:6. In each instance nucleic acid sequences that encode RSV Ga immunogens may optionally further comprise nucleic acid sequences that encode a signal peptide such as SEQ ID NO:17. Nucleic acid sequences that encode RSV Ga immunogens may encode a protein that comprises SEQ ID NO:6 and signal peptide SEQ ID NO:17. Nucleic acid sequences that encode RSV Ga immunogens may encode a protein that comprises SEQ ID NO:14.

Nucleic acid sequences that encode RSV Ga immunogens may comprise fragments of a nucleic acid sequence that is at least 98% homologous to SEQ ID NO:5. The nucleic acid sequence that is at least 98% homologous to SEQ ID NO:5 encodes a protein that is at least 98% homologous to SEQ ID NO:6. The fragment encodes an immunogenic fragment of the protein that is at least 98% homologous to SEQ ID NO:6. In some embodiments, the nucleic acid sequences that encodes the RSV Ga immunogen may comprise fragments of a nucleic acid sequence that is at least 98% homologous to SEQ ID NO:5 wherein the nucleic acid sequence encodes a protein that is at least 99% homologous to SEQ ID NO:6, in some embodiments nucleic acid sequence encodes a protein that comprises SEQ ID NO:6, and the fragment of the nucleic acid sequence encodes an immunogenic fragment of the protein that is at least 99% homologous to SEQ ID NO:6 such as an immunogenic fragment SEQ ID NO:6. In some such embodiments, the nucleic acid sequences that encodes the RSV Ga immunogen may comprise fragments of a nucleic acid sequence that is at least 99% homologous to SEQ ID NO:5 and in some embodiments, fragments of SEQ ID NO:5. In some embodiments, the nucleic acid sequences that encode RSV Ga immunogens may optionally further comprise nucleic acid sequences that encode a signal peptide such as SEQ ID NO:17. Nucleic acid sequences that encode RSV Ga immunogens may comprise fragments of SEQ ID NO:6 and coding sequence encoding signal peptide SEQ ID NO:17. Nucleic acid sequences that encode RSV Ga immunogens may comprise fragments of SEQ ID NO:13 that include coding sequence encoding signal peptide SEQ ID NO:17.

Nucleic acid sequences that encode RSV Gb immunogens may encode proteins comprising immunogenic fragments of proteins that are at least 98% homologous to SEQ ID NO:8. Nucleic acid sequences that encode RSV Gb immunogens may encode proteins that comprise immunogenic fragments of proteins that are at least 99% homologous to SEQ ID NO:8. Nucleic acid sequences that encode RSV Gb immunogens may encode proteins that comprise immunogenic fragments of SEQ ID NO:8. In each instance the nucleic acid sequences that encode proteins that comprise the immunogenic fragments may optionally further comprise nucleic acid sequences that encode a signal peptide such as nucleic acid sequences that encode SEQ ID NO:17. Nucleic acid sequences that encode RSV Gb immunogens may encode proteins that comprises an immunogenic fragment of SEQ ID NO:8 and signal peptide SEQ ID NO:17. Nucleic acid sequences that encode RSV Gb immunogens may encode proteins that may be an immunogenic fragment of SEQ ID NO:16 that comprises SEQ ID NO:17. Nucleic acid sequences that encode RSV Gb immunogens may encode proteins that comprise a protein that is at least 98% homologous to SEQ ID NO:8, and in some embodiments may encode a protein that is at least 99% homologous to SEQ ID NO:8. Nucleic acid sequences that encode RSV Gb immunogens may encode proteins that comprise SEQ ID NO:8. In each instance nucleic acid sequences that encode RSV Gb immunogens may optionally further comprise nucleic acid sequences that encode a signal peptide such as SEQ ID NO:17. Nucleic acid sequences that encode RSV Gb immunogens may encode a protein that comprises SEQ ID NO:8 and signal peptide SEQ ID NO:17. Nucleic acid sequences that encode RSV Gb immunogens may encode a protein that comprises SEQ ID NO:16.

Nucleic acid sequences that encode RSV Gb immunogens may comprise fragments of a nucleic acid sequence that is at least 98% homologous to SEQ ID NO:7. The nucleic acid sequence that is at least 98% homologous to SEQ ID NO:7 encodes a protein that is at least 98% homologous to SEQ ID NO:8. The fragment encodes an immunogenic fragment of the protein that is at least 98% homologous to SEQ ID NO:8. In some embodiments, the nucleic acid sequences that encodes the RSV Gb immunogen may comprise fragments of a nucleic acid sequence that is at least 98% homologous to SEQ ID NO:7 wherein the nucleic acid sequence encodes a protein that is at least 99% homologous to SEQ ID NO:8, in some embodiments nucleic acid sequence encodes a protein that comprises SEQ ID NO:8, and the fragment of the nucleic acid sequence encodes an immunogenic fragment of the protein that is at least 99% homologous to SEQ ID NO:8 such as an immunogenic fragment SEQ ID NO:8. In some such embodiments, the nucleic acid sequences that encodes the RSV Gb immunogen may comprise fragments of a nucleic acid sequence that is at least 99% homologous to SEQ ID NO:7 and in some embodiments, fragments of SEQ ID NO:7. In some embodiments, the nucleic acid sequences that encode RSV Gb immunogens may optionally further comprise nucleic acid sequences that encode a signal peptide such as SEQ ID NO:17. Nucleic acid sequences that encode RSV Gb immunogens may comprise fragments of SEQ ID NO:8 and coding sequence encoding signal peptide SEQ ID NO:17. Nucleic acid sequences that encode RSV Gb immunogens may comprise fragments of SEQ ID NO:15 that include coding sequence encoding signal peptide SEQ ID NO:17.

Nucleic acid sequences that encode RSV M2-1 immunogens may encode proteins comprising immunogenic fragments of proteins that are at least 98% homologous to SEQ ID NO:4. Nucleic acid sequences that encode RSV M2-1 immunogens may encode proteins that comprise immunogenic fragments of proteins that are at least 99% homologous to SEQ ID NO:4. Nucleic acid sequences that encode RSV M2-1 immunogens may encode proteins that comprise immunogenic fragments of SEQ ID NO:4. In each instance the nucleic acid sequences that encode proteins that comprise the immunogenic fragments may optionally further comprise nucleic acid sequences that encode a signal peptide such as nucleic acid sequences that encode SEQ ID NO:17. Nucleic acid sequences that encode RSV M2-1 immunogens may encode proteins that comprises an immunogenic fragment of SEQ ID NO:4 and signal peptide SEQ ID NO:17. Nucleic acid sequences that encode RSV F immunogens may encode proteins that may be an immunogenic fragment of SEQ ID NO:12 that comprises SEQ ID NO:17. Nucleic acid sequences that encode RSV M2-1 immunogens may encode proteins that comprise a protein that is at least 98% homologous to SEQ ID NO:4, and in some embodiments may encodes a protein that is at least 99% homologous to SEQ ID NO:4. Nucleic acid sequences that encode RSV M2-1 immunogens may encode proteins that comprise SEQ ID NO:4. In each instance nucleic acid sequences that encode RSV M2-1 immunogens may optionally further comprise nucleic acid sequences that encode a signal peptide such as SEQ ID NO:17. Nucleic acid sequences that encode RSV M2-1 immunogens may encode a protein that comprises SEQ ID NO:4 and signal peptide SEQ ID NO:17. Nucleic acid sequences that encode RSV M2-1 immunogens may encode a protein that comprises SEQ ID NO:12.

Nucleic acid sequences that encode RSV M2-1 immunogens may comprise fragments of a nucleic acid sequence that is at least 98% homologous to SEQ ID NO:3. The nucleic acid sequence that is at least 98% homologous to SEQ ID NO:3 encodes a protein that is at least 98% homologous to SEQ ID NO:4. The fragment encodes an immunogenic fragment of the protein that is at least 98% homologous to SEQ ID NO:4. In some embodiments, the nucleic acid sequences that encodes the RSV M2-1 immunogen may comprise fragments of a nucleic acid sequence that is at least 98% homologous to SEQ ID NO:3 wherein the nucleic acid sequence encodes a protein that is at least 99% homologous to SEQ ID NO:4, in some embodiments nucleic acid sequence encodes a protein that comprises SEQ ID NO:4, and the fragment of the nucleic acid sequence encodes an immunogenic fragment of the protein that is at least 99% homologous to SEQ ID NO:4 such as an immunogenic fragment SEQ ID NO:4. In some such embodiments, the nucleic acid sequences that encodes the RSV M2-1 immunogen may comprise fragments of a nucleic acid sequence that is at least 99% homologous to SEQ ID NO:3 and in some embodiments, fragments of SEQ ID NO:3. In some embodiments, the nucleic acid sequences that encode RSV M2-1 immunogens may optionally further comprise nucleic acid sequences that encode a signal peptide such as SEQ ID NO:17. Nucleic acid sequences that encode RSV M2-1 immunogens may comprise fragments of SEQ ID NO:4 and coding sequence encoding signal peptide SEQ ID NO:17. Nucleic acid sequences that encode RSV M2-1 immunogens may comprise fragments of SEQ ID NO:1 that include coding sequence encoding signal peptide SEQ ID NO:17.

Coding sequences may encode fusion proteins which comprise a combination of two or more of the RSV proteins set forth herein. Coding sequences may encode fusion proteins that include combinations of consensus proteins and/or fragments of consensus protein and/or variants of consensus protein and/or fragments of variants consensus proteins. The consensus proteins and/or fragments of consensus protein and/or variants of consensus protein and/or fragments of variants consensus proteins may be linked directly adjacent to each other or linked with a spacer or one or more amino acids in between. In some embodiments, the space may be a proteolytic cleavage site. In some embodiments, the space may be a proteolytic cleavage site recognized by a protease found in cells to which the vaccine is intended to be administered and/or taken up.

In some embodiments, coding sequences encode fusion proteins which comprise a combination of two or more of the RSV proteins set forth herein. For example, coding sequences may encode fusion proteins that comprise: SEQ ID NO:2 or an immunogenic fragment thereof and SEQ ID NO:4 or an immunogenic fragment thereof, such as SEQ ID NO:1 or an immunogenic fragment-encoding fragment thereof and SEQ ID NO:3 or an immunogenic fragment thereof-encoding fragment thereof; SEQ ID NO:2 or an immunogenic fragment thereof and SEQ ID NO:6 or an immunogenic fragment thereof, such as SEQ ID NO:1 or an immunogenic fragment-encoding fragment thereof and SEQ ID NO:5 or an immunogenic fragment thereof-encoding fragment thereof; SEQ ID NO:2 or an immunogenic fragment thereof and SEQ ID NO:8 or an immunogenic fragment thereof, such as SEQ ID NO:1 or an immunogenic fragment-encoding fragment thereof and SEQ ID NO:7 or an immunogenic fragment thereof-encoding fragment thereof; SEQ ID NO:4 or an immunogenic fragment thereof and SEQ ID NO:6 or an immunogenic fragment thereof, such as SEQ ID NO:3 or an immunogenic fragment-encoding fragment thereof and SEQ ID NO:5 or an immunogenic fragment thereof-encoding fragment thereof; SEQ ID NO:4 or an immunogenic fragment thereof and SEQ ID NO:8 or an immunogenic fragment thereof, such as SEQ ID NO:3 or an immunogenic fragment-encoding fragment thereof and SEQ ID NO:5 or an immunogenic fragment thereof-encoding fragment thereof; and SEQ ID NO:6 or an immunogenic fragment thereof and SEQ ID NO:8 or an immunogenic fragment thereof, such as SEQ ID NO:5 or an immunogenic fragment-encoding fragment thereof and SEQ ID NO:7 or an immunogenic fragment thereof-encoding fragment thereof. Coding sequences may encode fusion proteins which comprise a combination of three RSV proteins set forth herein. For example, coding sequences may encode fusion proteins that comprise: SEQ ID NO:2 or an immunogenic fragment thereof, SEQ ID NO:4 or an immunogenic fragment thereof and SEQ ID NO:6 or an immunogenic fragment thereof, such as SEQ ID NO:1 or an immunogenic fragment-encoding fragment thereof, SEQ ID NO:3 or an immunogenic fragment thereof-encoding fragment thereof and SEQ ID NO:5 or an immunogenic fragment-encoding fragment thereof; SEQ ID NO:2 or an immunogenic fragment thereof, SEQ ID NO:4 or an immunogenic fragment thereof and SEQ ID NO:8 or an immunogenic fragment thereof, such as SEQ ID NO:1 or an immunogenic fragment-encoding fragment thereof, SEQ ID NO:3 or an immunogenic fragment thereof-encoding fragment thereof and SEQ ID NO:7 or an immunogenic fragment-encoding fragment thereof; and SEQ ID NO:4 or an immunogenic fragment thereof, SEQ ID NO:6 or an immunogenic fragment thereof and SEQ ID NO:8 or an immunogenic fragment thereof, such as SEQ ID NO:3 or an immunogenic fragment-encoding fragment thereof, SEQ ID NO:5 or an immunogenic fragment thereof-encoding fragment thereof and SEQ ID NO:7 or an immunogenic fragment-encoding fragment thereof. Coding sequences may encode fusion proteins which comprise a combination of the four RSV proteins set forth herein such as coding sequences that encode SEQ ID NO:2 or an immunogenic fragment thereof, SEQ ID NO:4 or an immunogenic fragment thereof, SEQ ID NO:6 or an immunogenic fragment thereof, and SEQ ID NO:8 or an immunogenic fragment thereof, such as SEQ ID NO:1 or an immunogenic fragment-encoding fragment thereof, SEQ ID NO:3 or an immunogenic fragment thereof-encoding fragment thereof, SEQ ID NO:5 or an immunogenic fragment-encoding fragment thereof and SEQ ID NO:7 or an immunogenic fragment-encoding fragment thereof. Alternatively coding sequence encode one or more of the fusion proteins above may comprise a sequence that encodes a protein that is at least 98% or at least 99% homologous to SEQ ID NO:2 or an immunogenic fragment thereof in place of the portion of the fusion protein described above corresponding to SEQ ID NO:2 or an immunogenic fragment. Likewise, coding sequences for one or more of the fusion proteins above comprise coding sequence at least 98% or at least 99% homologous to SEQ ID NO:4 or an immunogenic fragment thereof in place of the portion of the fusion protein described above corresponding to SEQ ID NO:4 or an immunogenic fragment; one or more of the fusion proteins above may comprise a sequence at least 98% or at least 99% homologous to SEQ ID NO:6 or an immunogenic fragment thereof in place of the portion of the fusion protein described above corresponding to SEQ ID NO:6 or an immunogenic fragment; and/or one or more of the fusion proteins above may comprise a sequence at least 98% or at least 99% homologous to SEQ ID NO:8 or an immunogenic fragment thereof in place of the portion of the fusion protein described above corresponding to SEQ ID NO:8 or an immunogenic fragment. In some embodiments, coding sequence encode one or more of the fusion proteins above may comprise a sequence that c is at least 98% or at least 99% homologous to SEQ ID NO:1 or fragment thereof that is at least 98% or at least 99% homologous to an immunogenic fragment of SEQ ID NO:2 in place of the portion of the coding sequence of the fusion protein described above corresponding to portion that encodes SEQ ID NO:2 or an immunogenic fragment. Coding sequence encode one or more of the fusion proteins above may comprise a sequence that is at least 98% or at least 99% homologous to SEQ ID NO:3 or fragment thereof that is at least 98% or at least 99% homologous to an immunogenic fragment of SEQ ID NO:4 in place of the portion of the coding sequence of the fusion protein described above corresponding to portion that encodes SEQ ID NO:4 or an immunogenic fragment. Coding sequence encode one or more of the fusion proteins above may comprise a sequence that is at least 98% or at least 99% homologous to SEQ ID NO:5 or fragment thereof that is at least 98% or at least 99% homologous to an immunogenic fragment of SEQ ID NO:6 in place of the portion of the coding sequence of the fusion protein described above corresponding to portion that encodes SEQ ID NO:6 or an immunogenic fragment. Coding sequence encode one or more of the fusion proteins above may comprise a sequence that is at least 98% or at least 99% homologous to SEQ ID NO:7 or fragment thereof that is at least 98% or at least 99% homologous to an immunogenic fragment of SEQ ID NO:8 in place of the portion of the coding sequence of the fusion protein described above corresponding to portion that encodes SEQ ID NO:8 or an immunogenic fragment. Fusion proteins may include combinations of consensus proteins and/or fragments of consensus protein and/or variants of consensus protein and/or fragments of variants consensus proteins. The consensus proteins and/or fragments of consensus protein and/or variants of consensus protein and/or fragments of variants consensus proteins may be linked directly adjacent to each other or linked with a spacer or one or more amino acids in between. In some embodiments, the space may be a proteolytic cleavage site. In some embodiments, the space may be a proteolytic cleavage site recognized by a protease found in cells to which the vaccine is intended to be administered and/or taken up.

4. Plasmid

Provided herein is a vector that is capable of expressing one or more RSV proteins in the cell of a mammal in a quantity effective to elicit an immune response in the mammal. The vector may comprise heterologous nucleic acid encoding the one or more RSV antigens. The vector may be a plasmid. The plasmid may be useful for transfecting cells with nucleic acid encoding an RSV antigen, which the transformed host cell is cultured and maintained under conditions wherein expression of the RSV antigen takes place.

The plasmid may comprise a nucleic acid sequence that encodes one or more of the various RSV proteins disclosed above including coding sequences that encode synthetic, consensus antigen capable of eliciting an immune response against RSV are provided for each of the following three proteins: F, Ga and Gb, fragments of such proteins, variants of such proteins, fragments of variants or fusion proteins which are made up of combinations of consensus proteins and/or fragments of consensus protein and/or variants of consensus protein and/or fragments of variants consensus proteins. The plasmid may comprise a nucleic acid sequence that encodes RSV M2-1 proteins disclosed above including coding sequences that encode synthetic, consensus antigen capable of eliciting an immune response against RSV M2-1, fragments of such proteins, variants of such proteins, fragments of variants or fusion proteins which are made up of combinations of consensus proteins and/or fragments of consensus protein and/or variants of consensus protein and/or fragments of variants consensus proteins.

A single plasmid may contain coding sequence for a single RSV Immunogen, coding sequence for two RSV Immunogens, or coding sequence for three RSV Immunogens. In some embodiments, a coding sequence for a fourth RSV Immunogen may be provided. A single plasmid may contain coding sequence for RSV F Immunogen. A single plasmid may contain coding sequence for RSV Ga Immunogen. A single plasmid may contain coding sequence for RSV Gb Immunogen. A single plasmid may contain coding sequence for RSV F Immunogen and coding sequence for RSV Ga Immunogen. A single plasmid may contain coding sequence for RSV F Immunogen and coding sequence for RSV Gb Immunogen. A single plasmid may contain coding sequence for RSV Ga Immunogen and coding sequence for RSV Gb Immunogen. A single plasmid may contain coding sequence for RSV F Immunogen, coding sequence for RSV Ga Immunogen and coding sequence for RSV Gb Immunogen.

If RSV M2-1 coding sequence is provided, a single plasmid may contain coding sequence for RSV M2-1 Immunogen. A single plasmid may contain coding sequence for RSV F Immunogen and coding sequence for RSV M2-1 Immunogen. A single plasmid may contain coding sequence for RSV M2-1 Immunogen and coding sequence for RSV Ga Immunogen. A single plasmid may contain coding sequence for RSV M2-1 Immunogen and coding sequence for RSV Gb Immunogen. A single plasmid may contain coding sequence for RSV F Immunogen, coding sequence for RSV M2-1 Immunogen and coding sequence for RSV Ga Immunogen. A single plasmid may contain coding sequence for RSV F Immunogen, coding sequence for RSV M2-1 Immunogen and coding sequence for RSV Gb Immunogen. A single plasmid may contain coding sequence for RSV M2-1 Immunogen, coding sequence for RSV Ga Immunogen and coding sequence for RSV Gb Immunogen. A single plasmid may contain coding sequence for RSV F Immunogen, coding sequence for RSV M2-1 Immunogen, coding sequence for RSV Ga Immunogen and coding sequence for RSV Gb Immunogen.

In some embodiments, a plasmid may comprise coding sequence that encodes CCR20 alone or as part of one these plasmids. Similarly, plasmids may further comprise coding sequences for IL-12, IL-15 and/or IL-28.

The plasmid may further comprise an initiation codon, which may be upstream of the coding sequence, and a stop codon, which may be downstream of the coding sequence. The initiation and termination codon may be in frame with the coding sequence.

The plasmid may also comprise a promoter that is operably linked to the coding sequence The promoter operably linked to the coding sequence may be a promoter from simian virus 40 (SV40), a mouse mammary tumor virus (MMTV) promoter, a human immunodeficiency virus (HIV) promoter such as the bovine immunodeficiency virus (BIV) long terminal repeat (LTR) promoter, a Moloney virus promoter, an avian leukosis virus (ALV) promoter, a cytomegalovirus (CMV) promoter such as the CMV immediate early promoter, Epstein Barr virus (EBV) promoter, or a Rous sarcoma virus (RSV) promoter. The promoter may also be a promoter from a human gene such as human actin, human myosin, human hemoglobin, human muscle creatine, or human metallothionein. The promoter may also be a tissue specific promoter, such as a muscle or skin specific promoter, natural or synthetic. Examples of such promoters are described in US patent application publication no. US20040175727, the contents of which are incorporated herein in its entirety.

The plasmid may also comprise a polyadenylation signal, which may be downstream of the coding sequence. The polyadenylation signal may be a SV40 polyadenylation signal, LTR polyadenylation signal, bovine growth hormone (bGH) polyadenylation signal, human growth hormone (hGH) polyadenylation signal, or human β-globin polyadenylation signal. The SV40 polyadenylation signal may be a polyadenylation signal from a pCEP4 plasmid (Invitrogen. San Diego, Calif.).

The plasmid may also comprise an enhancer upstream of the coding sequence. The enhancer may be human actin, human myosin, human hemoglobin, human muscle creatine or a viral enhancer such as one from CMV, FMDV, RSV or EBV. Polynucleotide function enhances are described in U.S. Pat. Nos. 5,593,972, 5,962,428, and WO94/016737, the contents of each are fully incorporated by reference.

The plasmid may also comprise a mammalian origin of replication in order to maintain the plasmid extrachromosomally and produce multiple copies of the plasmid in a cell. The plasmid may be pVAX1, pCEP4 or pREP4 from Invitrogen (San Diego, Calif.), which may comprise the Epstein Barr virus origin of replication and nuclear antigen EBNA-1 coding region, which may produce high copy episomal replication without integration. The backbone of the plasmid may be pAV0242. The plasmid may be a replication defective adenovirus type 5 (Ad5) plasmid.

The plasmid may also comprise a regulatory sequence, which may be well suited for gene expression in a cell into which the plasmid is administered. The coding sequence may comprise a codon that may allow more efficient transcription of the coding sequence in the host cell.

The coding sequence may also comprise an Ig leader sequence. The leader sequence may be 5' of the coding sequence. The consensus antigens encoded by this sequence may comprise an N-terminal Ig leader followed by a consensus antigen protein. The N-terminal Ig leader may be IgE or IgG.

The plasmid may be pSE420 (Invitrogen, San Diego, Calif.), which may be used for protein production in *Escherichia coli* (*E. coli*). The plasmid may also be pYES2 (Invitrogen, San Diego, Calif.), which may be used for protein production in *Saccharomyces cerevisiae* strains of yeast. The plasmid may also be of the MAXBAC™ complete baculovirus expression system (Invitrogen, San Diego, Calif.), which may be used for protein production in insect cells. The plasmid may also be pcDNA 1 or pcDNA3 (Invitrogen, San Diego, Calif.), which may be used for protein production in mammalian cells such as Chinese hamster ovary (CHO) cells.

5. Compositions

Compositions are provided which comprise nucleic acid molecules. The compositions may comprise a plurality of copies of a single nucleic acid molecule such a single plasmid, a plurality of copies of a two or more different nucleic acid molecules such as two or more different plasmids. For example a compositions may comprise plurality of two, three, four, five, six, seven, eight, nine or ten or more different nucleic acid molecules. Such a compositions may comprise plurality of two, three, four, five, six, seven, eight, nine or ten or more different plasmids.

Compositions may comprise nucleic acid molecules, such as plasmids, that collectively contain coding sequence for a single RSV Immunogen, coding sequence for two RSV Immunogens, or coding sequence for three RSV Immunogens. In some instances, coding sequence for a fourth RSV Immunogen may be provided.

Compositions comprising coding sequence of two RSV Immunogens may be on a single nucleic acid molecule such as a single plasmid or the compositions may comprise two different nucleic acid molecule such as two different plasmids wherein one nucleic acid molecule comprises the coding sequence one RSV Immunogen and the other nucleic acid molecule comprises the coding sequence different RSV Immunogen. Similarly, compositions comprising coding sequence three RSV Immunogens may comprise a single nucleic acid molecule such as a single plasmid, two different nucleic acid molecules or three different nucleic acid molecules. Likewise, compositions comprising coding sequence four RSV Immunogens may comprise a single nucleic acid molecule such as a single plasmid, two different nucleic acid molecules, three different nucleic acid molecules or four different nucleic acid molecule.

In some embodiments, a composition comprises a plurality single nucleic acid molecule encoding one RSV Immunogen such as RSV F Immunogen, RSV Ga Immunogen or RSV Gb Immunogen. In some embodiments, a composition comprises a plurality single nucleic acid molecule, such a single plasmid encoding two RSV Immunogen such as RSV F Immunogen and RSV Ga Immunogen. RSV F Immunogen and RSV Gb Immunogen, and RSV Ga Immunogen and RSV Gb Immunogen. In some embodiments, a composition comprises a plurality single nucleic acid molecule, such a single plasmid encoding three RSV Immunogen such as RSV Ga Immunogen, RSV F Immunogen and RSV Gb Immunogen.

In some embodiments, a composition comprises a plurality two different nucleic acid molecules, such as two plasmids, each different nucleic acid molecule comprising a single different coding sequence for a different RSV Immunogen wherein pairs of different nucleic acid molecule comprise RSV F Immunogen and RSV Ga Immunogen, RSV F Immunogen and RSV Gb Immunogen, and RSV Ga Immunogen and RSV Gb Immunogen.

In some embodiments, a composition comprises a plurality two different nucleic acid molecules, such as two plasmids, which collectively comprising coding sequence for three different RSV Immunogen. In some embodiments, one encodes RSV F Immunogen and RSV Ga Immunogen, and the second encodes RSV Gb Immunogen. In some embodiments, one encodes RSV F Immunogen and RSV Gb Immunogen, and the second encodes RSV Ga Immunogen. In some embodiments, one encodes Ga Immunogen and RSV Gb Immunogen, and the second encodes RSV F Immunogen.

In some embodiments, a composition comprises a plurality single nucleic acid molecule encoding RSV M2-1 Immunogen.

In some embodiments in which coding sequences for RSV M2-1 are provided, a composition comprises a plurality single nucleic acid molecules, such a single plasmid encoding two RSV Immunogen such as RSV F Immunogen and RSV M2-1 Immunogen, RSV M2-1 Immunogen and RSV Ga Immunogen, and RSV M2-1 Immunogen and RSV Gb Immunogen.

In some embodiments in which coding sequences for RSV M2-1 are provided, a plurality single nucleic acid molecules, such a single plasmid encoding three RSV Immunogen such as RSV F Immunogen. RSV M2-1 Immunogen and RSV Ga Immunogen, RSV F Immunogen, RSV M2-1 Immunogen and RSV Gb Immunogen, RSV M2-1 Immunogen, RSV Ga Immunogen and RSV Gb Immunogen. In some embodiments, a composition comprises a plurality single nucleic acid molecule, such a single plasmid encoding three RSV Immunogen such as RSV F Immunogen, RSV M2-1 Immunogen, RSV Ga Immunogen and RSV Gb Immunogen.

In some embodiments in which coding sequences for RSV M2-1 are provided, a composition comprises a plurality two different nucleic acid molecules, such as two plasmids, each different nucleic acid molecule comprising a single different coding sequence for a different RSV Immunogen wherein pairs of different nucleic acid molecule comprise RSV F Immunogen and RSV M2-1 Immunogen, RSV M2-1 Immunogen and RSV Ga Immunogen, and RSV M2-1 Immunogen and RSV Gb Immunogen.

In some embodiments in which coding sequences for RSV M2-1 are provided, a composition comprises a plurality two different nucleic acid molecules, such as two plasmids, which collectively comprising coding sequence for three different RSV Immunogen or which one is RSV M2-1. Embodiments may be selected from the group consisting of: one nucleic acid molecule encodes RSV F Immunogen and RSV M2-1 Immunogen and the second encodes RSV Ga Immunogen; one nucleic acid molecule encodes RSV F Immunogen and RSV M2-1 Immunogen and the second encodes RSV Gb Immunogen; one encodes RSV F Immunogen and RSV Ga Immunogen, and the second encodes RSV M2-L Immunogen; one encodes RSV F Immunogen and RSV Gb Immunogen, and the second encodes RSV M2-1 Immunogen; one encodes RSV M2-1 Immunogen and RSV Ga Immunogen, and the second encodes RSV F Immunogen; one encodes RSV M2-1 Immunogen and RSV Ga Immunogen, and the second encodes RSV Gb Immunogen; one encodes RSV M2-1 Immunogen and RSV Gb Immunogen, and the second encodes RSV F Immunogen; one encodes RSV M2-1 Immunogen and RSV Gb Immunogen, and the second encodes RSV Ga Immunogen; and one encodes Ga Immunogen and RSV Gb Immunogen, and the second encodes RSV M2-1 Immunogen.

In some embodiments in which coding sequences for RSV M2-1 are provided, a composition comprises a plurality two different nucleic acid molecules, such as two plasmids, which collectively comprising coding sequence for four different RSV Immunogen. In some embodiments; one nucleic acid molecule encodes RSV F Immunogen and the second encodes RSV M2-1 Immunogen, RSV Ga Immunogen and RSV Gb Immunogen; one nucleic acid molecule encodes RSV M2-1 Immunogen and the second encodes RSV F Immunogen, RSV Ga Immunogen and RSV Gb Immunogen; one encodes RSV Ga Immunogen and the second encodes RSV F Immunogen, RSV M2-1 Immunogen and RSV Gb Immunogen, one encodes RSV Gb Immunogen and the second encodes RSV F Immunogen, RSV M2-1 Immunogen and RSV Ga Immunogen, one encodes RSV F and RSV M2-1 Immunogen the second encodes RSV Ga Immunogen and RSV Gb Immunogen, one encodes RSV F and RSV Ga Immunogen the second encodes RSV M2-1 Immunogen and RSV Gb Immunogen, and one encodes RSV F and RSV Gb Immunogen the second encodes RSV M2-1 Immunogen and RSV Ga Immunogen. In some embodiments, a composition comprises a plurality three different nucleic acid molecules, such as three plasmids, which collectively comprising coding sequence for three different RSV Immunogen. In some embodiments: one nucleic acid molecule encodes RSV F Immunogen, one encodes RSV M2-1 Immunogen and the third second encodes RSV Ga Immunogen; one nucleic acid molecule encodes RSV F Immunogen, one encodes RSV M2-1 Immunogen and the third second encodes RSV Gb Immunogen; one nucleic acid molecule encodes RSV F Immunogen, one encodes RSV Ga Immunogen and the third second encodes RSV Gb Immunogen; and one nucleic acid molecule encodes RSV M2-1 Immunogen, one encodes RSV Ga Immunogen and the third second encodes RSV Gb Immunogen. In some embodiments, a composition comprises a plurality three different nucleic acid molecules, such as three plasmids, which collectively comprising coding sequence for four different RSV Immunogens. In some embodiments: one nucleic acid molecule encodes RSV F Immunogen, the second encodes RSV M2-1 Immunogen and the third encodes RSV Ga Immunogen and RSV Gb Immunogen; one nucleic acid molecule encodes RSV F Immunogen, the second encodes RSV Ga Immunogen and the third encodes RSV M2-1 Immunogen and RSV Gb Immunogen; one nucleic acid molecule encodes RSV F Immunogen, the second encodes RSV Gb Immunogen and the third encodes RSV M2-1 Immunogen and RSV Ga Immunogen; one nucleic acid molecule encodes RSV M2-1 Immunogen, the second encodes RSV Ga Immunogen and the third encodes RSV F Immunogen and RSV Gb Immunogen; one nucleic acid molecule encodes RSV M2-1 Immunogen, the second encodes RSV Gb Immunogen, and the third encodes RSV F Immunogen and RSV Ga Immunogen; and one encodes RSV Ga Immunogen, the second encodes RSV Gb Immunogen, and the third encodes RSV F Immunogen and RSV M2-1. In some embodiments, a composition comprises a plurality four different nucleic acid molecules, such as four plasmids, which collectively comprising coding sequence for four different RSV Immunogens, i.e. one nucleic acid molecule encodes RSV F Immunogen, the second encodes RSV M2-1 Immunogen, the third encodes RSV Ga Immunogen and the fourth encodes RSV Gb Immunogen.

In some embodiments, a composition further comprises coding sequence for chemokine CCL20, IL-12, IL-15 and/or IL-28. Coding sequence for chemokine CCL20, IL-12, IL-15 and/or IL-28 may be included on one or more nucleic acid molecules that comprise coding sequence for one or more RSV Immunogens. Coding sequence for chemokine (CCL20, IL-12, IL-15 and/or IL-28 may be included on a separate nucleic acid molecules such as a separate plasmid.

6. Vaccine

Provided herein is a vaccine capable of generating in a mammal an immune response against RSV. The vaccine may comprise each plasmid as discussed above. The vaccine may comprise a plurality of the plasmids, or combinations thereof. The vaccine may be provided to induce a therapeutic or prophylactic immune response.

In some embodiments, the vaccine is preferably Th1 biased so as not to play into prior Th2 related pathogenesis and it should be able to function in a neutralization sensitive environment. Preferably, it should be non-live.

Vaccines may be used to deliver one or more immunogenic targets selected from the group consisting of: F, Ga and Gb, fragments of such proteins, variants of such proteins, fragments of variants. In the case of delivery of multiple targets, vaccines may include multiple compositions or a single compositions. Plasmids may be used which encode multiple proteins on a single plasmid or compositions which comprise different plasmids that encode different proteins. In some embodiments, vaccines may be used to deliver M2, fragments thereof, variants of M2-1, fragments of variants, alone or in combination with one or more immunogenic targets selected from the group consisting of: F, Ga and Gb, fragments of such proteins, variants of such proteins, fragments of variants. In the case of delivery of multiple targets, vaccines may include multiple compositions or a single compositions. Plasmids may be used which encode multiple proteins on a single plasmid or compositions which comprise different plasmids that encode different proteins.

The vaccine may further comprise a pharmaceutically acceptable excipient. The pharmaceutically acceptable excipient may be functional molecules as vehicles, adjuvants, carriers, or diluents. The pharmaceutically acceptable excipient may be a transfection facilitating agent, which may include surface active agents, such as immune-stimulating complexes (ISCOMS). Freunds incomplete adjuvant, LPS analog including monophosphoryl lipid A, muramyl peptides, quinone analogs, vesicles such as squalene and squalene, hyaluronic acid, lipids, liposomes, calcium ions, viral proteins, polyanions, polycations, or nanoparticles, or other known transfection facilitating agents.

The transfection facilitating agent is a polyanion, polycation, including poly-L-glutamate (LGS), or lipid. The transfection facilitating agent is poly-L-glutamate, and more preferably, the poly-L-glutamate is present in the vaccine at a concentration less than 6 mg/ml. The transfection facilitating agent may also include surface active agents such as immune-stimulating complexes (ISCOMS), Freunds incomplete adjuvant, LPS analog including monophosphoryl lipid A, muramyl peptides, quinone analogs and vesicles such as squalene and squalene, and hyaluronic acid may also be used administered in conjunction with the genetic construct. In some embodiments, the DNA plasmid vaccines may also include a transfection facilitating agent such as lipids, liposomes, including lecithin liposomes or other liposomes known in the art, as a DNA-liposome mixture (see for example W09324640), calcium ions, viral proteins, polyanions, polycations, or nanoparticles, or other known transfection facilitating agents. Preferably, the transfection facilitating agent is a polyanion, polycation, including poly-L-glutamate (LGS), or lipid. Concentration of the transfection agent in the vaccine is less than 4 mg/ml, less than 2 mg/ml, less than 1 mg/ml, less than 0.750 mg/ml, less than 0.500 mg/ml, less than 0.250 mg/ml, less than 0.100 mg/ml, less than 0.050 mg/ml, or less than 0.010 mg/ml.

The pharmaceutically acceptable excipient may be one or more adjuvants. An adjuvant may be other genes that are expressed from the same or from an alternative plasmid or are delivered as proteins in combination with the plasmid above in the vaccine. The one or more adjuvants may be proteins and/or nucleic acid molecules that encode proteins selected from the group consisting of: CCL20, α-interferon (IFN-α), β-interferon (IFN-β), γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence or coding sequence that encodes the signal sequence deleted and optionally including a different signal peptide such as that from IgE or coding sequence that encodes a difference signal peptide such as that from IgE, IL-28, MHC, CD80, CD86, IL-1, IL-2, IL-4, IL-5, IL-6, IL-10, IL-18, MCP-1, MIP-1α, MIP-1β, IL-8, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2F, TAP1, TAP2 and functional fragments thereof, or a combination thereof. In some embodiments adjuvant may be one or more proteins and/or nucleic acid molecules that encode proteins selected from the group consisting of: CCL-20, IL-12, IL-15, IL-28, CTACK, TECK, MEC or RANTES. Examples of IL-12 constructs and sequences are disclosed in PCT application no. PCT/US1997/019502 and corresponding U.S. application Ser. No. 08/956,865, and U.S. Provisional Application Ser. No. 61/569,600 filed Dec. 12, 2011, which are each incorporated herein by reference. Examples of IL-15 constructs and sequences are disclosed in PCT application no. PCT/US04/18962 and corresponding U.S. application Ser. No. 10/560, 650, and in PCT application no. PCT/US07/00886 and corresponding U.S. application Ser. No. 12/160,766, and in PCT application no. PCT/US10/048827, which are each incorporated herein by reference. Examples of IL-28 constructs and sequences are disclosed in PCT application no. PCT/US09/039648 and corresponding U.S. application Ser. No. 12/936,192, which are each incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of RANTES and other constructs and sequences are disclosed in PCT application no. PCT/US1999/004332 and corresponding U.S. application Ser. No. 09/622,452, which are each incorporated herein by reference. Other examples of RANTES constructs and sequences are disclosed in PCT application no. PCT/US11/024098, which is incorporated herein by reference. Examples of chemokines CTACK, TECK and MEC constructs and sequences are disclosed in PCT application no. PCT/US2005/042231 and corresponding U.S. application Ser. No. 11/719,646, which are each incorporated herein by reference. Examples of OX40 and other immunomodulators are disclosed in U.S. application Ser. No. 10/560,653, which is incorporated herein by reference. Examples of DR5 and other immunomodulators are disclosed in U.S. application Ser. No. 09/622,452, which is incorporated herein by reference.

The vaccine may further comprise a genetic vaccine facilitator agent as described in U.S. Ser. No. 021,579 filed Apr. 1, 1994, which is fully incorporated by reference.

The vaccine may comprise the consensus antigens and plasmids at quantities of from about 1 nanogram to 100 milligrams; about 1 microgram to about 10 milligrams; or preferably about 0.1 microgram to about 10 milligrams; or more preferably about 1 milligram to about 2 milligram. In some preferred embodiments, pharmaceutical compositions according to the present invention comprise about 5 nanogram to about 1000 micrograms of DNA. In some preferred embodiments, the pharmaceutical compositions contain about 10 nanograms to about 800 micrograms of DNA. In some preferred embodiments, the pharmaceutical compositions contain about 0.1 to about 500 micrograms of DNA. In some preferred embodiments, the pharmaceutical compositions contain about 1 to about 350 micrograms of DNA. In some preferred embodiments, the pharmaceutical compositions contain about 25 to about 250 micrograms, from about 100 to about 200 microgram, from about 1 nanogram to 100 milligrams; from about 1 microgram to about 10 milligrams; from about 0.1 microgram to about 10 milligrams; from about 1 milligram to about 2 milligram, from about 5 nanogram to about 1000 micrograms, from about 10 nanograms to about 800 micrograms, from about 0.1 to about 500 micrograms, from about 1 to about 350 micrograms, from about 25 to about 250 micrograms, from about 100 to about 200 microgram of the consensus antigen or plasmid thereof.

The vaccine may be formulated according to the mode of administration to be used. An injectable vaccine pharmaceutical composition may be sterile, pyrogen free and particulate free. An isotonic formulation or solution may be used. Additives for isotonicity may include sodium chloride, dextrose, mannitol, sorbitol, and lactose. The vaccine may comprise a vasoconstriction agent. The isotonic solutions may include phosphate buffered saline. Vaccine may further comprise stabilizers including gelatin and albumin. The stabilizing may allow the formulation to be stable at room or ambient temperature for extended periods of time such as LGS or polycations or polyanions to the vaccine formulation.

7. Methods of Delivery the Vaccine

Provided herein is a method for delivering the vaccine for providing genetic constructs and proteins of the consensus antigen which comprise epitopes that make them particular effective against immunogens of RSV against which an immune response can be induced. The method of delivering the vaccine or vaccination may be provided to induce a therapeutic and prophylactic immune response. The vaccination process may generate in the mammal an immune response against RSV. The vaccine may be delivered to an individual to modulate modulate the activity of the mammal's immune system and enhance the immune response. The delivery of the vaccine may be the transfection of the consensus antigen as a nucleic acid molecule that is expressed in the cell and delivered to the surface of the cell upon which the immune system recognized and induces a cellular, humoral, or cellular and humoral response. The delivery of the vaccine may be used to induce or elicit and immune response in mammals against RSV by administering to the mammals the vaccine as discussed above.

Upon delivery of the vaccine and plasmid into the cells of the mammal, the transfected cells will express and secrete consensus antigens for each of the plasmids injected from the vaccine. These proteins will be recognized as foreign by the immune system and antibodies will be made against them. These antibodies will be maintained by the immune system and allow for an effective response to subsequent RSV infections.

The vaccine may be administered to a mammal to elicit an immune response in a mammal. The mammal may be human, primate, non-human primate, cow, cattle, sheep, goat, antelope, bison, water buffalo, bison, bovids, deer, hedgehogs, elephants, llama, alpaca, mice, rats, and chicken.

a. Combination Treatments

The vaccine may be administered in combination with other proteins and/or genes encoding CCL20, α-interferon, γ-interferon, platelet derived growth factor (PDGF), TNFα, TNFβ, GM-CSF, epidermal growth factor (EGF), cutaneous T cell-attracting chemokine (CTACK), epithelial thymus-expressed chemokine (TECK), mucosae-associated epithelial chemokine (MEC), IL-12, IL-15 including IL-15 having the signal sequence deleted and optionally including the different signal peptide such as the IgE signal peptide, MHC, CD80, CD86, IL-28, IL-1, IL-2, IL-4, IL-5, IL-6, IL-10, IL-18, MCP-1, MIP-1α, MIP-1β, IL-8, RANTES, L-selectin, P-selectin, E-selectin, CD34, GlyCAM-1, MadCAM-1, LFA-1, VLA-1, Mac-1, p150.95, PECAM, ICAM-1, ICAM-2, ICAM-3, CD2, LFA-3, M-CSF, G-CSF, mutant forms of IL-18, CD40, CD40L, vascular growth factor, fibroblast growth factor, IL-7, nerve growth factor, vascular endothelial growth factor, Fas, TNF receptor, Flt, Apo-1, p55, WSL-1, DR3, TRAMP, Apo-3, AIR, LARD, NGRF, DR4, DR5, KILLER, TRAIL-R2, TRICK2, DR6, Caspase ICE, Fos, c-jun, Sp-1, Ap-1, Ap-2, p38, p65Rel, MyD88, IRAK, TRAF6, IkB, Inactive NIK, SAP K, SAP-1, JNK, interferon response genes, NFkB, Bax, TRAIL, TRAILrec, TRAILrecDRC5, TRAIL-R3, TRAIL-R4, RANK, RANK LIGAND, Ox40, Ox40 LIGAND, NKG2D, MICA, MICB, NKG2A, NKG2B, NKG2C, NKG2E, NKG2E, NKG2F, TAP1, TAP2 and functional fragments thereof or combinations thereof. In some embodiments, the vaccine is administered in combination with one or more of the following nucleic acid molecules and/or proteins: nucleic acid molecules selected from the group consisting of nucleic acid molecules comprising coding sequence that encode one or more of CCL20, IL-12, IL-15, IL-28, CTACK, TECK, MEC and RANTES or functional fragments thereof, and proteins selected from the group consisting of: CCL02, IL-12 protein, IL-15 protein, IL-28 protein, CTACK protein, TECK protein, MEC protein or RANTES protein or functional fragments thereof.

The vaccine may be administered by different routes including orally, parenterally, sublingually, transdermally, rectally, transmucosally, topically, via inhalation, via buccal administration, intrapleurally, intravenous, intraarterial, intraperitoneal, subcutaneous, intramuscular, intranasal intrathecal, and intraarticular or combinations thereof. For veterinary use, the composition may be administered as a suitably acceptable formulation in accordance with normal veterinary practice. The veterinarian can readily determine the dosing regimen and route of administration that is most appropriate for a particular animal. The vaccine may be administered by traditional syringes, needleless injection devices, "microprojectile bombardment gone guns", or other physical methods such as electroporation ("EP"), "hydrodynamic method", or ultrasound.

The plasmid of the vaccine may be delivered to the mammal by several well known technologies including DNA injection (also referred to as DNA vaccination) with and without in vivo electroporation, liposome mediated, nanoparticle facilitated, recombinant vectors such as recombinant adenovirus, recombinant adenovirus associated virus and recombinant vaccinia. The consensus antigen may be delivered via DNA injection and along with in vivo electroporation.

b. Electroporation

Administration of the vaccine via electroporation of the plasmids of the vaccine may be accomplished using electroporation devices that can be configured to deliver to a desired tissue of a mammal a pulse of energy effective to cause reversible pores to form in cell membranes, and preferable the pulse of energy is a constant current similar to a preset current input by a user. The electroporation device may comprise an electroporation component and an electrode assembly or handle assembly. The electroporation component may include and incorporate one or more of the various elements of the electroporation devices, including: controller, current waveform generator, impedance tester, waveform logger, input element, status reporting element, communication port, memory component, power source, and power switch. The electroporation may be accomplished using an in vivo electroporation device, for example CELLECTRA EP system (VGX Pharmaceuticals, Blue Bell, Pa.) or Elgen electroporator (Genetronics, San Diego, Calif.) to facilitate transfection of cells by the plasmid.

The electroporation component may function as one element of the electroporation devices, and the other elements are separate elements (or components) in communication with the electroporation component. The electroporation component may function as more than one element of the electroporation devices, which may be in communication with still other elements of the electroporation devices separate from the electroporation component. The elements of the electroporation devices existing as parts of one electromechanical or mechanical device may not limited as the elements can function as one device or as separate elements in communication with one another. The electroporation component may be capable of delivering the pulse of energy that produces the constant current in the desired tissue, and includes a feedback mechanism. The electrode assembly may include an electrode array having a plurality of electrodes in a spatial arrangement, wherein the electrode assembly receives the pulse of energy from the electroporation component and delivers same to the desired tissue through the electrodes. At least one of the plurality of electrodes is neutral during delivery of the pulse of energy and measures impedance in the desired tissue and communicates the impedance to the electroporation component. The feedback mechanism may receive the measured impedance and can adjust the pulse of energy delivered by the electroporation component to maintain the constant current.

A plurality of electrodes may deliver the pulse of energy in a decentralized pattern. The plurality of electrodes may deliver the pulse of energy in the decentralized pattern through the control of the electrodes under a programmed sequence, and the programmed sequence is input by a user to the electroporation component. The programmed sequence may comprise a plurality of pulses delivered in sequence, wherein each pulse of the plurality of pulses is delivered by at least two active electrodes with one neutral electrode that measures impedance, and wherein a subsequent pulse of the plurality of pulses is delivered by a different one of at least two active electrodes with one neutral electrode that measures impedance.

The feedback mechanism may be performed by either hardware or software. The feedback mechanism may be performed by an analog closed-loop circuit. The feedback occurs every 50 µs, 20 µs, 10 µs or 1 µs, but is preferably a real-time feedback or instantaneous (i.e., substantially instantaneous as determined by available techniques for determining response time). The neutral electrode may measure the impedance in the desired tissue and communicates the impedance to the feedback mechanism, and the feedback mechanism responds to the impedance and adjusts the pulse of energy to maintain the constant current at a value similar to the preset current. The feedback mechanism may maintain the constant current continuously and instantaneously during the delivery of the pulse of energy.

Examples of electroporation devices and electroporation methods that may facilitate delivery of the DNA vaccines of the present invention, include those described in U.S. Pat. No. 7,245,963 by Draghia-Akli, et al., U.S. Patent Pub. 2005/0052630 submitted by Smith, et al., the contents of which are hereby incorporated by reference in their entirety. Other electroporation devices and electroporation methods that may be used for facilitating delivery of the DNA vaccines include those provided in co-pending and co-owned U.S. patent application Ser. No. 11/874,072, filed Oct. 17, 2007, which claims the benefit under 35 USC 119(e) to U.S. Provisional Application Ser. Nos. 60/852,149, filed Oct. 17, 2006, and 60/978,982, filed Oct. 10, 2007, all of which are hereby incorporated in their entirety.

U.S. Pat. No. 7,245,963 by Draghia-Akli, et al. describes modular electrode systems and their use for facilitating the introduction of a biomolecule into cells of a selected tissue in a body or plant. The modular electrode systems may comprise a plurality of needle electrodes; a hypodermic needle; an electrical connector that provides a conductive link from a programmable constant-current pulse controller to the plurality of needle electrodes; and a power source. An operator can grasp the plurality of needle electrodes that are mounted on a support structure and firmly insert them into the selected tissue in a body or plant. The biomolecules are then delivered via the hypodermic needle into the selected tissue. The programmable constant-current pulse controller is activated and constant-current electrical pulse is applied to the plurality of needle electrodes. The applied constant-current electrical pulse facilitates the introduction of the biomolecule into the cell between the plurality of electrodes. The entire content of U.S. Pat. No. 7,245,963 is hereby incorporated by reference.

U.S. Patent Pub. 2005/0052630 submitted by Smith, et al. describes an electroporation device which may be used to effectively facilitate the introduction of a biomolecule into cells of a selected tissue in a body or plant. The electroporation device comprises an electro-kinetic device ("EKD device") whose operation is specified by software or firmware. The EKD device produces a series of programmable constant-current pulse patterns between electrodes in an array based on user control and input of the pulse parameters, and allows the storage and acquisition of current waveform data. The electroporation device also comprises a replaceable electrode disk having an array of needle electrodes, a central injection channel for an injection needle, and a removable guide disk. The entire content of U.S. Patent Pub. 2005/0052630 is hereby incorporated by reference.

The electrode arrays and methods described in U.S. Pat. No. 7,245,963 and U.S. Patent Pub. 2005/0052630 may be adapted for deep penetration into not only tissues such as muscle, but also other tissues or organs. Because of the configuration of the electrode array, the injection needle (to deliver the biomolecule of choice) is also inserted completely into the target organ, and the injection is administered perpendicular to the target issue, in the area that is pre-delineated by the electrodes The electrodes described in U.S. Pat. No. 7,245,963 and U.S. Patent Pub. 2005/005263 are preferably 20 mm long and 21 gauge.

Additionally, contemplated in some embodiments that incorporate electroporation devices and uses thereof, there are electroporation devices that are those described in the following patents: U.S. Pat. No. 5,273,525 issued Dec. 28, 1993, U.S. Pat. No. 6,110,161 issued Aug. 29, 2000, U.S. Pat. No. 6,261,281 issued Jul. 17, 2001, and U.S. Pat. No. 6,958,060 issued Oct. 25, 2005, and U.S. Pat. No. 6,939,862 issued Sep. 6, 2005. Furthermore, patents covering subject matter provided in U.S. Pat. No. 6,697,669 issued Feb. 24, 2004, which concerns delivery of DNA using any of a variety of devices, and U.S. Pat. No. 7,328,064 issued Feb. 5, 2008, drawn to method of injecting DNA are contemplated herein. The above-patents are incorporated by reference in their entirety.

c. Method of Preparing DNA Plasmids

Provided herein is methods for preparing the DNA plasmids that comprise the DNA vaccines discussed herein. The DNA plasmids, after the final subcloning step into the mammalian expression plasmid, can be used to inoculate a cell culture in a large scale fermentation tank, using known methods in the art.

The DNA plasmids for use with the EP devices of the present invention can be formulated or manufactured using a combination of known devices and techniques, but preferably they are manufactured using an optimized plasmid manufacturing technique that is described in a licensed, U.S. provisional application Ser. No. 60/939,792, which was filed on May 23, 2007. In some examples, the DNA plasmids used in these studies can be formulated at concentrations greater than or equal to 10 mg/mL. The manufacturing techniques also include or incorporate various devices and protocols that are commonly known to those of ordinary skill in the art, in addition to those described in U.S. Ser. No. 60/939,792, including those described in a licensed patent, U.S. Pat. No. 7,238,522, which issued on Jul. 3, 2007. The above-referenced application and patent, U.S. Ser. No. 60/939,792 and U.S. Pat. No. 7,238,522, respectively, are hereby incorporated in their entirety.

EXAMPLES

The present invention is further illustrated in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. Thus, various modifications of the invention in addition to those shown and described herein will be apparent to those skilled in the art from the foregoing description. Such modifications are also intended to fall within the scope of the appended claims Example 1

With expected continued increases in the number of individuals at high risk for RSV infection in the coming years (e.g., young infants and the elderly), there is a dire need for the development of an efficacious and financially manageable treatment for RSV infection. DNA vaccines, small bacterial plasmids genetically engineered to express an encoded protein of interest upon immunization, offer several significant advantages that may help in circumventing many of the hurdles involved in designing an efficacious RSV vaccine. For instance, to prevent clinically significant illness and re-infection, the vaccine would have to confer greater and longer lasting immunity than that which occurs from natural RSV infection. DNA vaccines not only elicit both humoral (e.g., neutralization antibody) and cellular (e.g., cytotoxic T lymphocytes) immune response, but can also elicit lifelong immunity against many viruses. In addition, the primary targets for RSV vaccination are neonates and young infants. Neonatal immune system is functionally immature and thus, develops only a weak immune response to conventional vaccines (e.g., live attenuated or inactivated virus). DNA vaccines, on the other hand, have been shown to be safe and immunogenic in neonatal animal models. Furthermore, the presence of maternal antibody at the time of immunization has been known to suppress or inhibit immune responses to a variety of conventional vaccines. With DNA vaccine, however, the immunizing protein is not present in the vaccine preparation and therefore, should not be susceptible to direct inactivation by maternal antibodies.

Currently, there are three main RSV vaccines in or near early stages of clinical trials: 1) live attenuated RSV (MedImmune, Philadelphia, Pa.); 2) Sendai virus expressing the RSV F and/or G proteins (AmVac, Switzerland); and 3) virus-like particles containing the G protein of RSV (Novavax, Rockville, Md.) (http://www.clinicaltrials.gov/ct2/results?term=RSV&pg=1). Although these approaches have shown some degree of efficacy in the prevention of RSV infection, there are other inherent disadvantages associated with such vaccine designs. For instance, the biggest issues with live attenuated virus are under-attenuation or mutations leading to reversion to virulence and therefore, should not be administered to immunocompromised individuals. A common drawback to all viral vectors is the host immune response as recognition of viral proteins leads to the generation of neutralizing antibodies that may significantly reduce the efficacy of the vaccine upon subsequent immunization. Lastly, the G protein of RSV is highly variable between the two subtypes of RSV and therefore, any vaccine targeting the G protein is not likely to provide cross protection.

In contrast, DNA vaccines have been shown to be highly immunogenic and lack many of the disadvantages associated with the above described vaccine approach. When delivered via electroporation, DNA vaccine immunogenicity further improves. DNA vaccines contain less than a complete set of viral components and like protein subunit vaccines have no risk for virulence reversion or infection of the host making them safe to use in both infants and in immunocompromised individuals.

Figure 1:
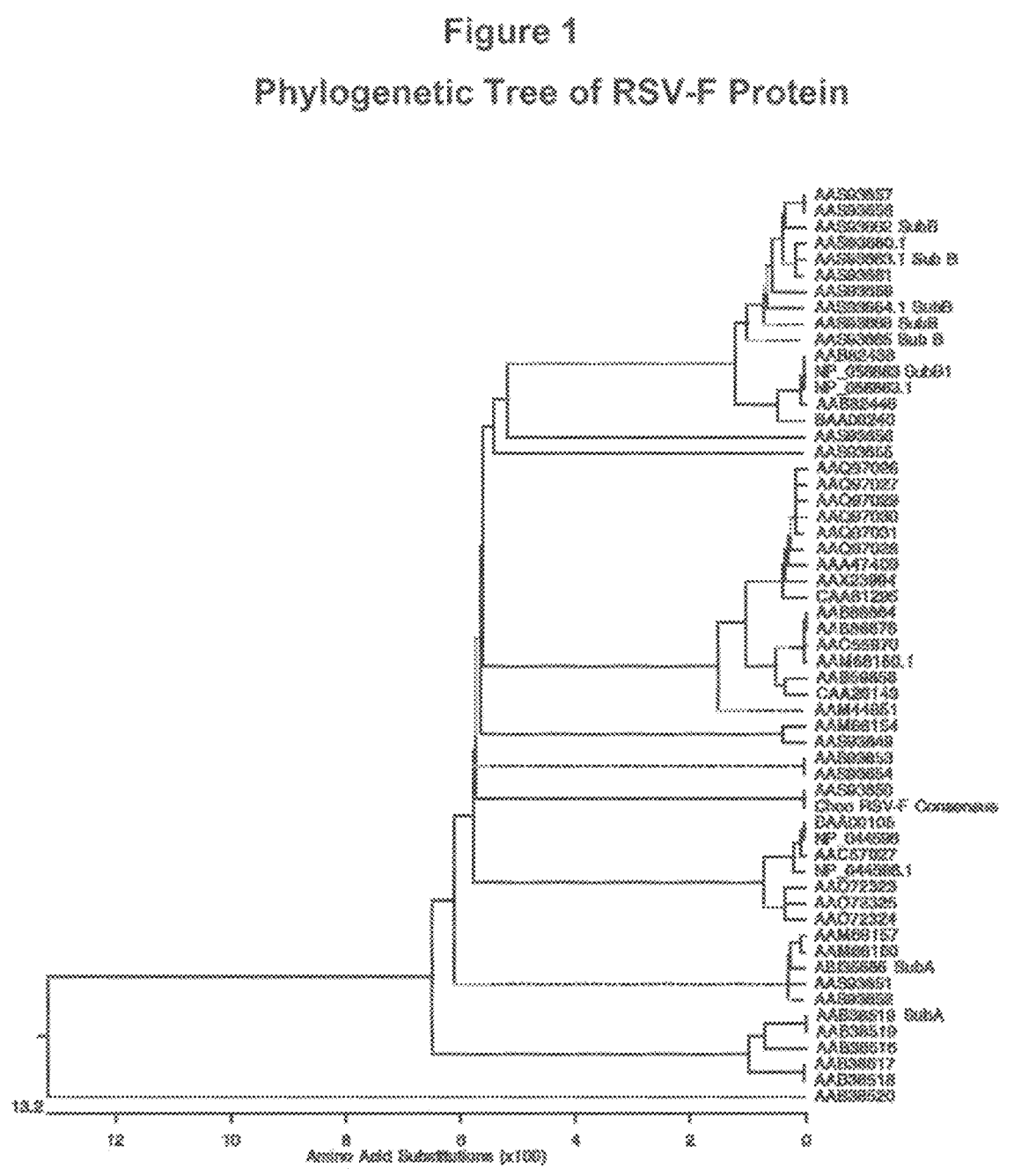

Using consensus sequences of both subtype A and B of RSV provides the basis to obtain broader protection against both strains of the virus. Such advantages make consensus RSV DNA vaccine much more beneficial and potentially more efficacious than any other approaches suggested in the past Major RSV proteins—fusion (F), glycoprotein (Ga), and glycoprotein (Ga) were chosen as targets for new RSV vaccines. Also chosen for evaluation was the second matrix protein (M2). As mentioned above, F and G proteins are expressed on the surface and are ideal targets for neutralizing antibodies. M2 protein contains the major immunodominant CD8 T cell epitope. For each of these RSV proteins, a single consensus sequence was generated based on the amino acid sequences provided by PUBMED for both subtype A and B of RSV (FIG. 1 shows the phylogenetic tree of RSV-F Protein, the consensus RSV F protein amino acid sequence is set forth in SEQ ID NO:2; FIG. 2 shows the phylogenetic tree of RSV M2-1 Protein, the consensus RSV M2-1 protein amino acid sequence is set forth in SEQ ID NO:4. In a preferred embodiments, codon and RNA optimized DNA sequences that encode the consensus protein sequences are produced and used to make DNA vaccines which may be delivered using electroporation.

Example 2

Successful expression of RSV consensus F protein was confirmed through immunofluorescence microscopy and/or western blot analysis. Constructs were used in immunization studies.

Mice were immunized with varying dosages of the different RSV DNA vaccine constructs. One group received the DNA vaccine backbone plasmid pVAX as a control. One group received 5 μg dose of plasmid RSV-F, one group received 15 μg dose of plasmid RSV-F; one group received 30 μg dose of plasmid RSV-F; and one group received 60 μg dose of plasmid RSV-F.

Figure 3:
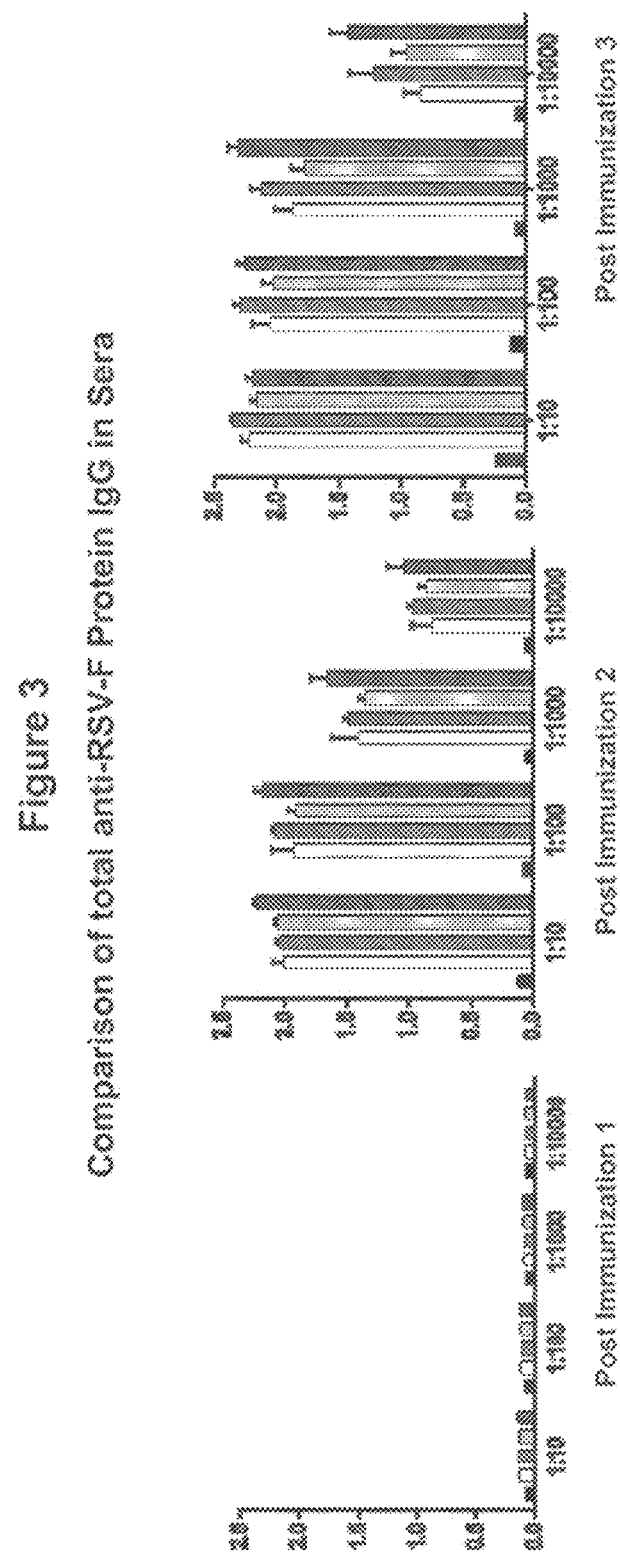
FIG. 3 shows results anti-RSV F protein IgG at various time points following immunization with RSV F vaccine.
Figure 4:
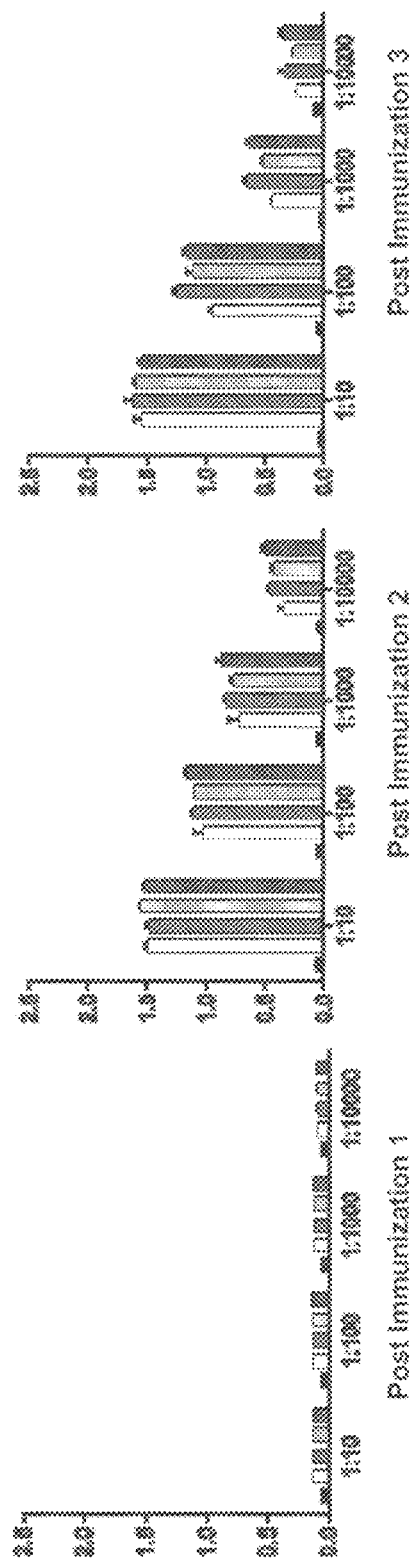
FIG. 4 shows results anti-RSV F protein IgA at various time points following immunization with RSV F vaccine.

Mice were immunized 2 weeks apart for a total of 3 immunizations (weeks 0, 2 and 4) intramuscularly with electroporation. Mice were bled at weeks 2, 4, 6 and 12 after each immunization and the total RSV F protein specific IgG and IgA antibody was measured in the sera. FIG. 3 shows anti-RSV F protein IgG after immunization 1 (i.e. at week 0), immunization 2 (i.e. week 2) and after immunizations 3 (i.e. week 4). FIG. 4 shows anti-RSV F protein IgA after immunization 1 (i.e. at week 0), immunization 2 (i.e. week 2) and after immunizations 3 (i.e. week 4). Mice were sacrificed at week 12. In addition to comparisons of total IgG in sera and of total IgA in sera, a comparison of IFN-γ production at different dosage of RSV-F vaccine approximately 8 weeks after last immunization was done.

Figure 5:
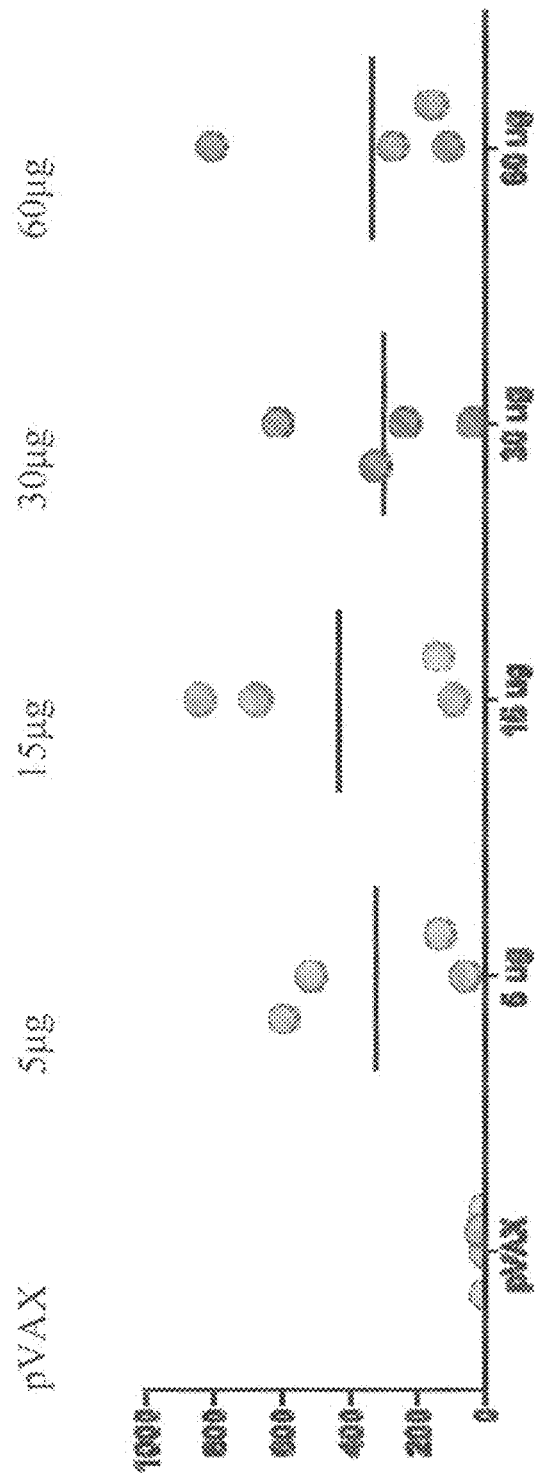
FIG. 5 shows results from a comparison of IFN-γ production at different dosage of RSV-F vaccine approximately 8 weeks after last immunization.

RSV-F DNA vaccine elicited high levels of both IgG and IgA in sera. Responses were detectable as early as 2 weeks after 2nd immunization for all dosage studied. The antibody responses induced appear to be strongly Th1 biased, thus avoiding prior issues of the side effects of Th2 immune responses to RSV. RSV-F specific CD8 T cells were observed even after 8 weeks after the last immunization. FIG. 5 shows results from a comparison of IFN-γ production at different dosage of RSV-F vaccine approximately 8 weeks after last immunization.

Example 3

Chemokines are a family of small proteins secreted by cells with ability to induce directed chemotaxis toward a higher concentration gradient in nearby responsive cells. Various groups have investigated the feasibility of using chemokines as immune adjuvants.

CCL28/MEC (mucosa-associated epithelial chemokine) which binds CCR10 is expressed on epithelial cells in the gut, lung, breast, and the salivary glands. Use of mucosal chemokines in previous studies showed their utility as immune adjuvants, inducing better immune response in the mucosal tissues after systemic immunization.

Experiments were performed to test the use of a CCL28 genetic construct as an adjuvant for the consensus RSV F protein DNA vaccine construct. A genetic construct that comprised nucleotide sequence encoding CCL20, also referred to a liver activation regulated chemokine (LARC) or Macrophage Inflammatory Protein-3 (MIP3A), was also tested as a possible adjuvant for the consensus RSV F protein DNA vaccine construct.

The immunization schedule for RSV-F plus chemokine experiments utilized three groups of mice: one receiving RSV-F construct only; one receiving RSV-F construct plus CCL20 construct; and one receiving RSV-F construct plus CCL28 construct. Mice were immunized a total of three times: at week 0, at week 2 and at week 4. Mice were bled at week 2, week 4 and week 5. At week 5, mice underwent vaginal wash to collect vaginal samples and were sacrificed after which lungs and spleens were collected.

Figure 6:
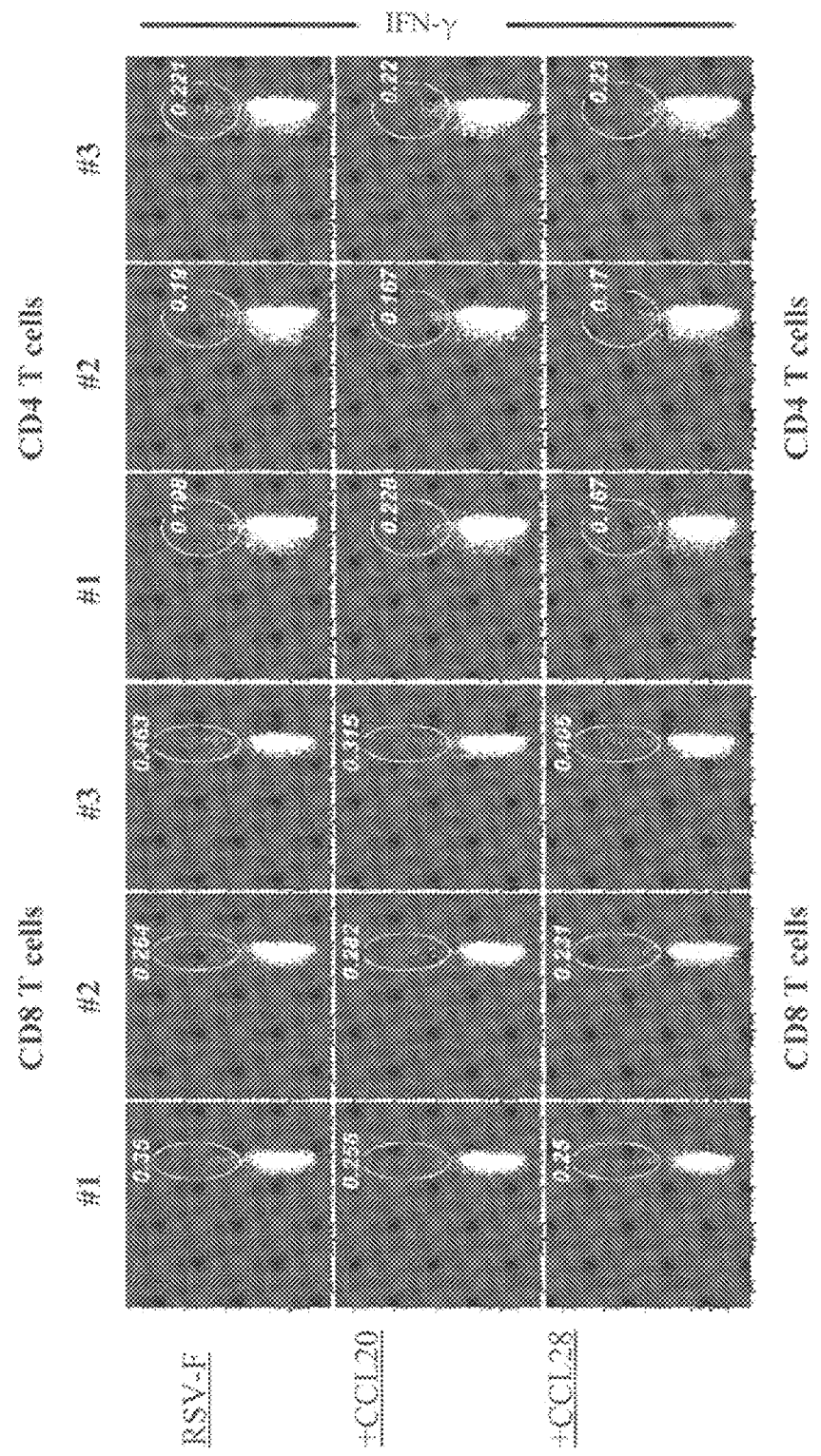
FIG. 6 shows results from a comparison of IFN-γ+ CD8 and CD4 T cells in spleen after RSV-F+/−chemokine immunization in the spleen.
Figure 7:
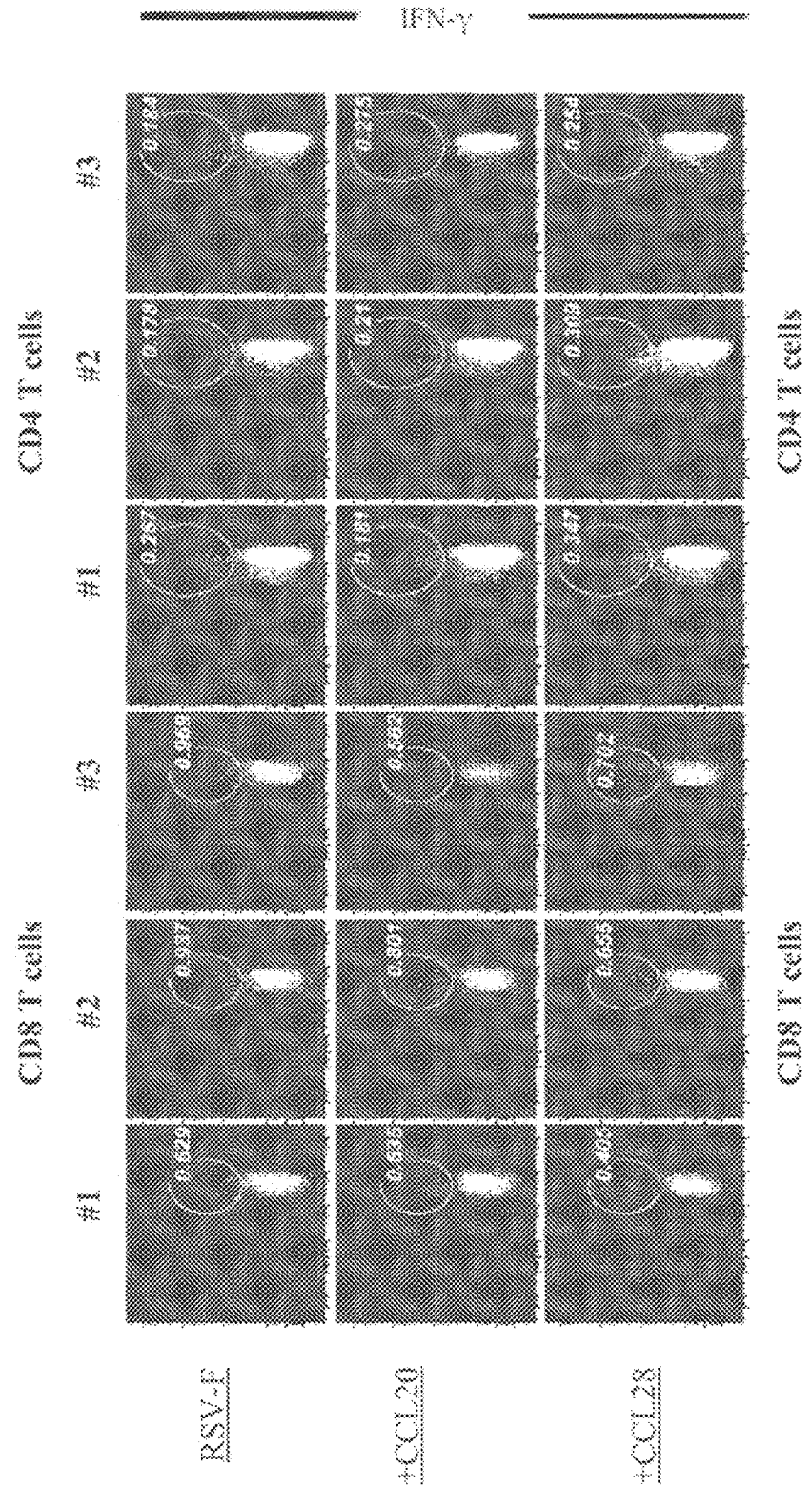
FIG. 7 shows results from a comparison of IFN-γ+ CD8 and CD4 T cells in spleen after RSV-F+/−chemokine immunization in the lung.

Comparisons were made of IFN-γ+ CD8 and CD4 T cells in spleen after RSV-F+/−chemokine immunization in the spleen (FIG. 6) and in lung (FIG. 7) after RSV-F+/−chemokine immunization.

Figure 8:
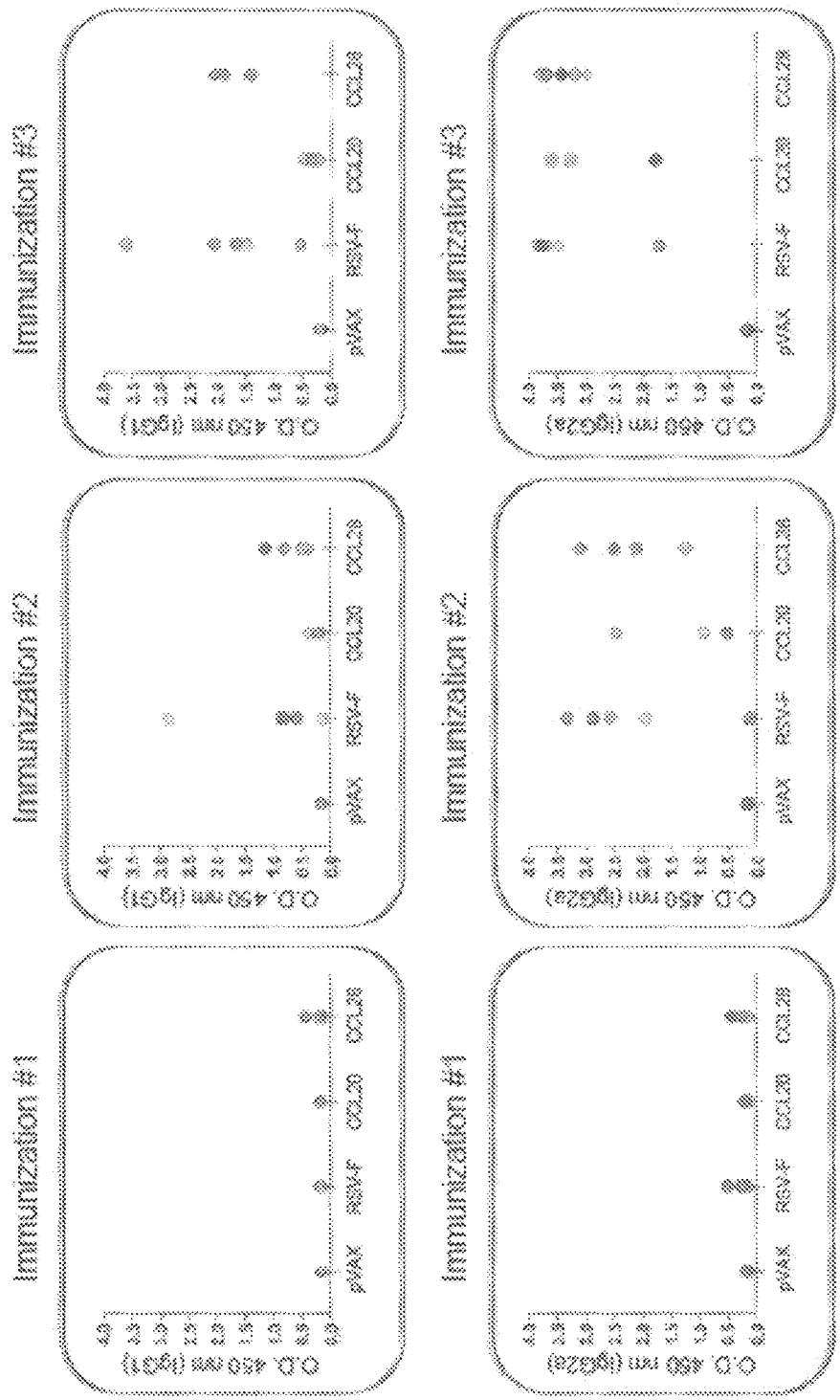
FIG. 8 shows results from a comparison of IgG Endpoint Titer in Sera and IgG subtypes (IgG1 vs IgG2a) in Sera.
Figure 9:
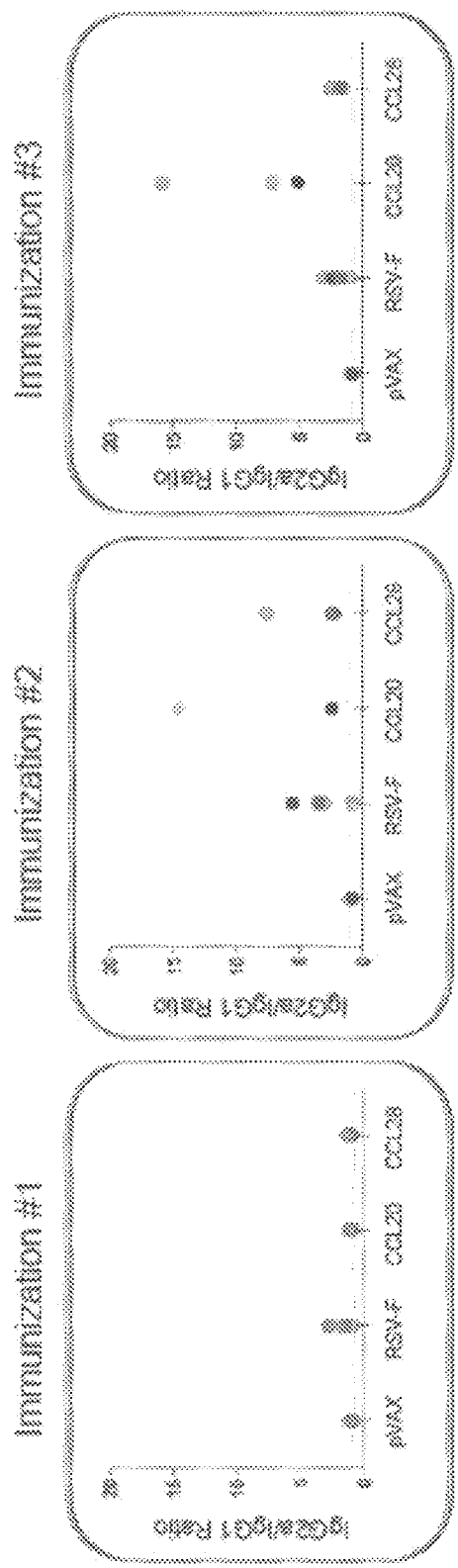
FIG. 9 shows a comparison of IgG2a/IgG1 ratio.

IgG Endpoint Titer in Sera was measured and IgG subtypes (IgG1 vs IgG2a) in Sera were compared (FIG. 8). A comparison of IgG2a/IgG1 ratio was also done (FIG. 9).

CCL20 and CCL28 chemokines did not appear to enhance CD8 and CD4 T cell immune responses after RSV-F DNA vaccination in either the spleen or the lung (based on IFN-γICS) although it is unclear if the dosage of chemokine construct was insufficient.

Animals receiving the CCL20 immune adjuvant exhibited a heavy bias towards a Th1 immune response (primarily IgG2a) after RSV-F DNA vaccination. Driving immune response away from Th2 and towards Th1 may be useful in order to avoid vaccine-associated enhanced disease after RSV infection.

Example 4

As noted above, administration of coding sequences that encode CCL20 led to a preferential Th1 immune response and away from Th2 immune responses. This property of CCL20 administration may be useful in the context of both an immunotherapeutic as well as a vaccine adjuvant for other targets in which a shift increasing Th1 immune responses and decreasing Th2 immune responses is desirable.

For example, CCL20 or administration of nucleic acid molecules that encode CCL20 may be useful to treat individuals who have autoimmune diseases or inflammatory conditions characterized by Th2 immune responses. The ability to decrease Th2 immune responses as shown herein can be used to reduce Th2 immune responses associated with certain autoimmune diseases or inflammatory conditions including for example.

In addition, CCL20 may be used as a vaccine adjuvant as described herein with vaccines targeting other infection diseases as well as cancer. The Th1 increasing/Th2 decreasing properties associated with the use of CCL20 as a vaccine adjuvant may be useful in vaccines. SEQ ID NO:18 and SEQ ID NO:20 contains high expression coding sequences for CCL20 with and without coding sequences encoding the IgE signal peptide. In some embodiments, SEQ ID NO:18 further comprises a start codon. SEQ ID NO:19 and SEQ ID NO:21 contains consensus sequences for CCL20 with and without coding sequences encoding the IgE signal peptide. In some embodiments, SEQ ID NO:19 further comprises an N terminal; methionine Example 5

The Luciferase Reporter Gene Assay in TZM-bl Cells is based on Single-Round Infection with Molecularly Cloned Env-Pseudotyped Viruses. TZM-bl (JC53-bl) is a genetically engineered HeLa cell line that expresses CD4, CXCR4 and CCR5 and contains Tat-inducible Luc and β-Gal reporter genes. The assay provides high success rate in single-round infections, increased assay capacity (2-day assay), increased precision (accurately measure 50% neutralization), improved level of standardization (stable cell line), and an optimized and validated assay platform. Montefiori, D. C. (2004) Current Protocols in Immunology, John Wiley & Sons, 12.11.1-12.11.15, which is incorporated herein by reference, described the assay.

Figure 10:
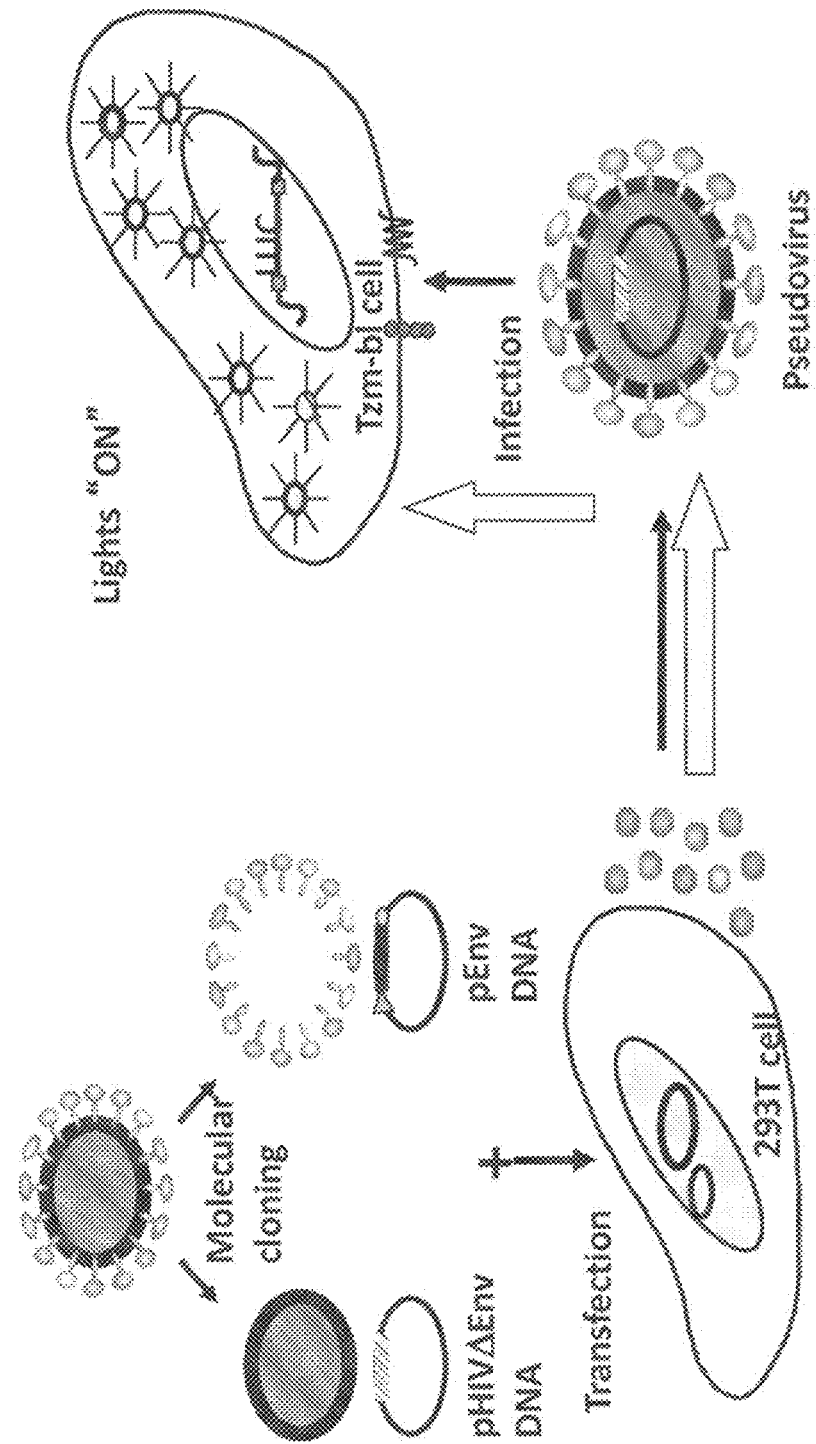
FIG. 10 depicts Env-Pseudotyped viruses in TZM-BL Cells/"ON".

FIG. 10 depicts Env-Pseudotyped viruses in TZM-BL Cells/"ON".

Figure 11:
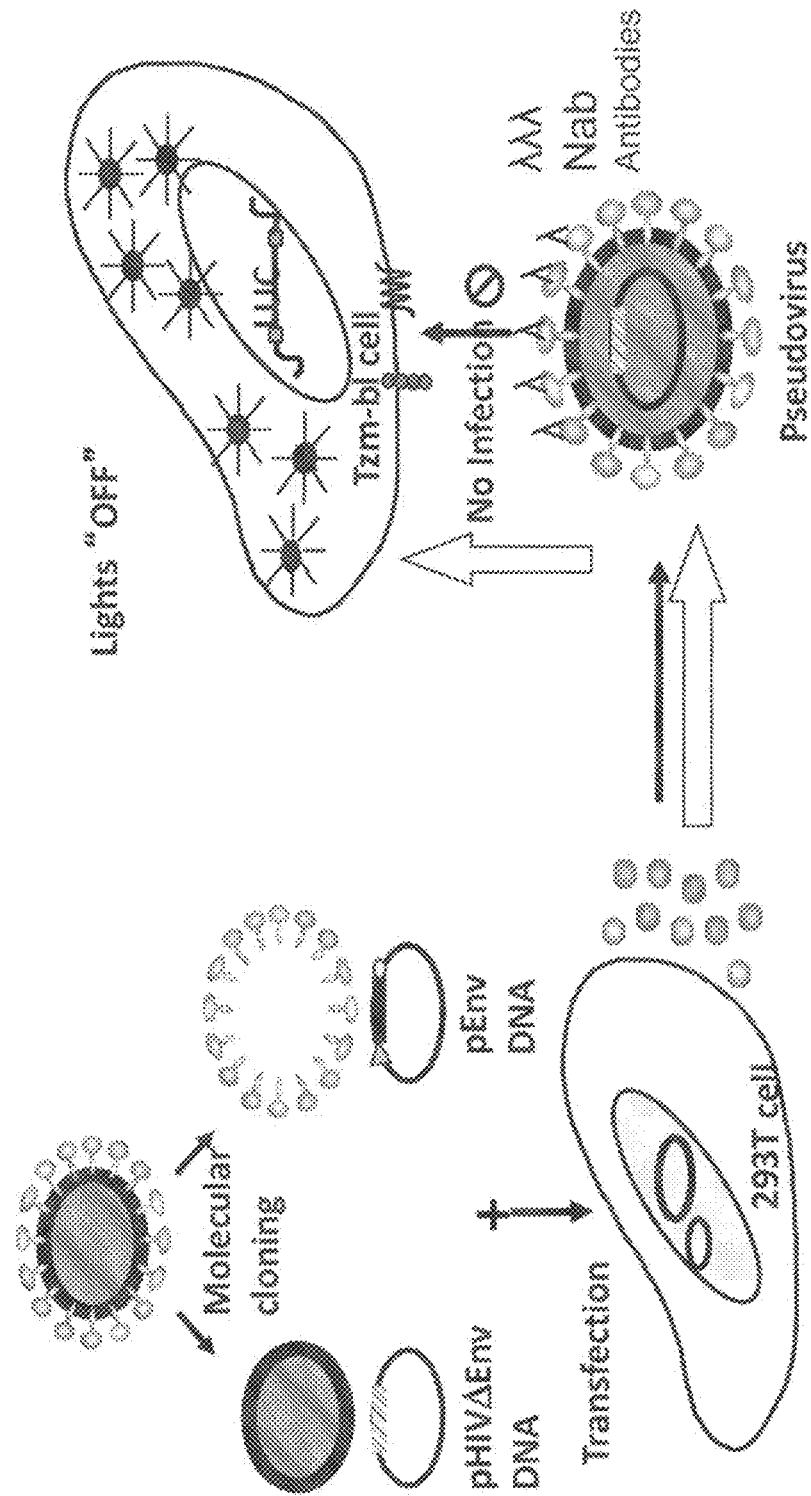
FIG. 11 depicts Env-Pseudotyped viruses in TZM-BL Cells/"OFF".

FIG. 11 depicts Env-Pseudotyped viruses in TZM-BL Cells/"OFF".

FIG. 12 depicts RSV-Fusion Pseudo viral production in 293T cells.

Figure 13:
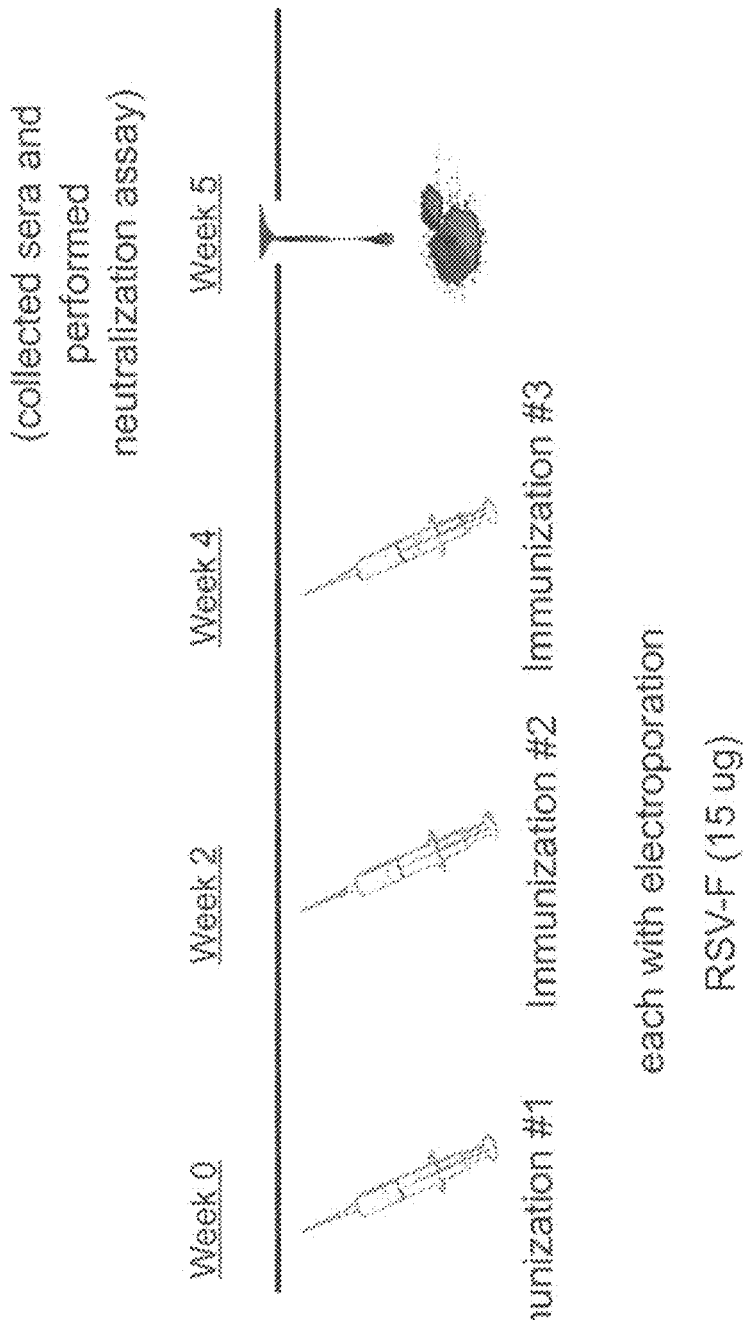
FIG. 13 shows the immunization protocol used for a RSV-F Neutralization Study using the assay.

FIG. 13 shows the immunization protocol used for a RSV-F Neutralization Study using the assay.

FIG. 14 shows data from quantification of RSV-F mediated infection in different target cells. Infectivity of pseudotypes bearing RSV-F proteins. Pseudotype viruses were pelleted, and the particle amounts were estimated by quantifying HIV p24 antigen. Cells were infected with pseudotype viruses or no envelope bearing a panel of diverse cell lines containing 10 ng of particulate HIV p24 antigen. At 72 h postinfection, cells supernatant and assayed for p24 antigen. Values are the means of triplicate wells with the standard deviations.

Figure 15:
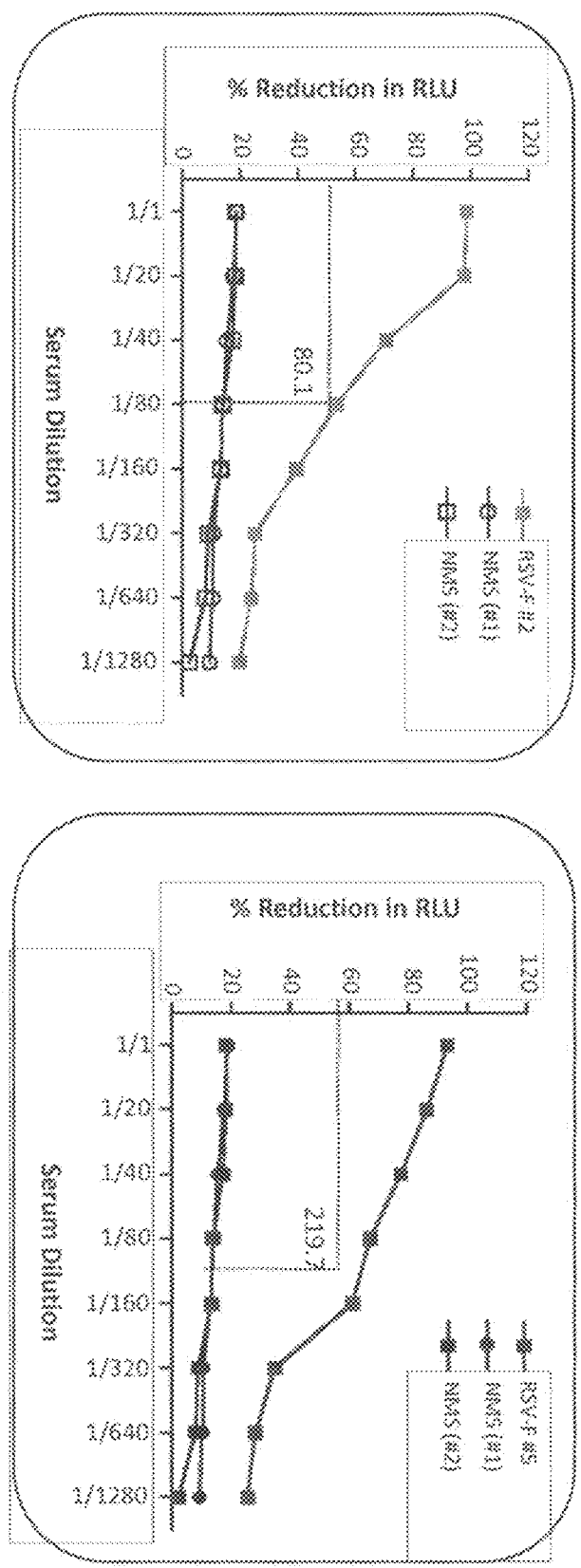
FIG. 15 shows data from quantification of RSV-F neutralization activity in TZM-bl HeLa cells.

FIG. 15 shows data from quantification of RSV-F neutralization activity in TZM-bl HeLa cells. The data show results of a comparison of neutralizing ability to RSV-F using luciferase assay from RSV-F immunized serum samples from DNA vaccinated animals that can block the HIV-Luc/FMDV pseudovirus from entering and infecting target cells. The titer is defined as the reciprocal of the dilution of plasma that produces 50% inhibition of virus. The ability of the serum sample from the vaccinated mice to neutralize and block the infectivity of HIV-1 Luc/RSV-F the absence of such blocking activity in normal mouse serum (NMS).

Figure 16:
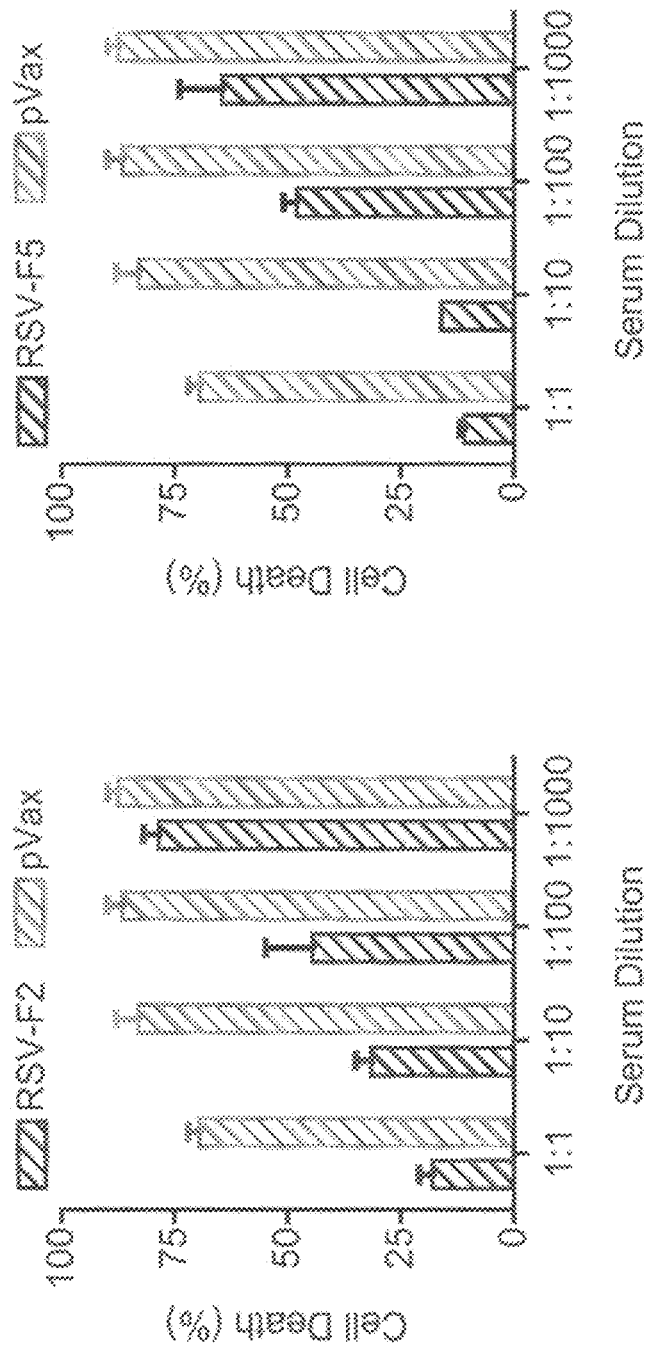
FIG. 16 shows data from quantification of cell death activity by RSV-F pseudo virus in HeLa cells.

FIG. 16 shows data from quantification of cell death activity by RSV-F pseudo virus in HeLa cells. The results show that consensus RSV-F DNA plasmid elicits potent humoral and cellular immune responses in mice after 3 vaccinations with electroporation. A high level of RSV-F specific IgG in sera was observed as early as 1 week post $2^{nd}$ immunization with just 5 ug DNA. Cell-mediated immune response were detectable as far out as 8 weeks post $3^{rd}$ immunization suggesting the long-term persistence of immune response after RSV-F DNA vaccination. Increase in RSV-F DNA concentration did not result in increased immune response. Antibodies generated after 3 vaccinations with RSV-F DNA plus electroporation were capable of neutralizing infection as measured by pseudo-virus neutralization assay. Results also showed mitigated RSV-F mediated apoptosis of target cells.

Example 6

Figure 17:
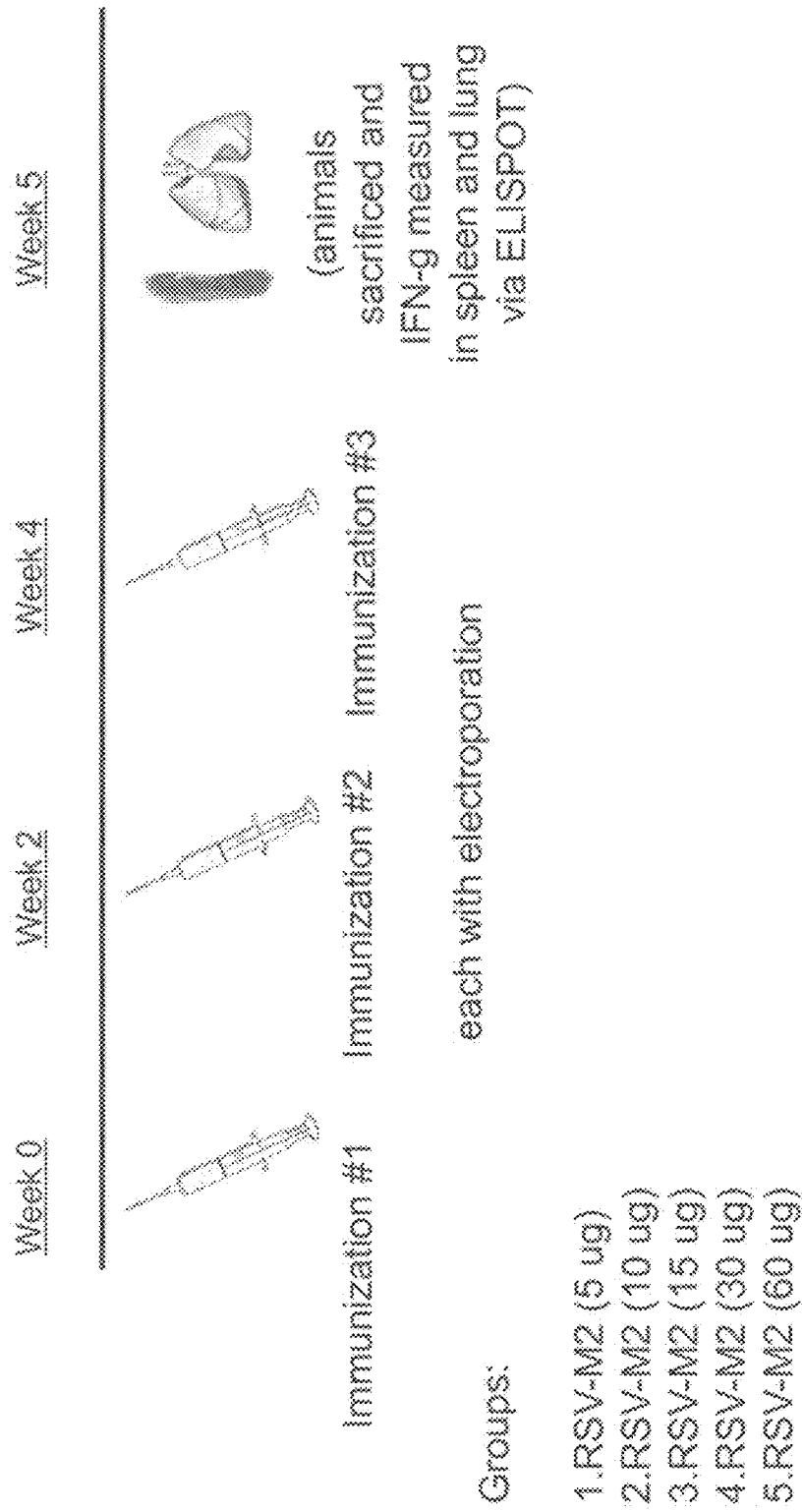
FIG. 17 shows the immunization schedule for RSV-M2 dosage study that was undertaken.

FIG. 17 shows the immunization schedule for RSV-M2 dosage study that was undertaken. Data collected from that study includes a comparison of IFN-g production at different dosages of RSV-M2 vaccine 1 week after last immunization (FIG. 18). The results showed that a consensus-based RSV-M2 DNA plasmid elicited significant cellular immune responses in mice after 3 vaccinations with electroporation. High level of IFN-g+ T cells specific for either the immunodominant or subdominant epitopes of RSV-M2 in both spleen and in lung were observed. Maximum immune response was observed with 60 ug DNA (however, response not much greater than that observed with 10 ug DNA).

Example 7

Further study was undertaken to evaluate CCL20 as potential immune adjuvant to enhance mucosal immune response after DNA immunization. CCL20 (liver activation regulated chemokine—LARC; macrophage inflammatory protein 3—MIP3a) binds to CCR6 and is expressed in lymph nodes, liver, appendix, fetal lung (lower levels in thymus, testis, prostate, and gut).

Figure 19:
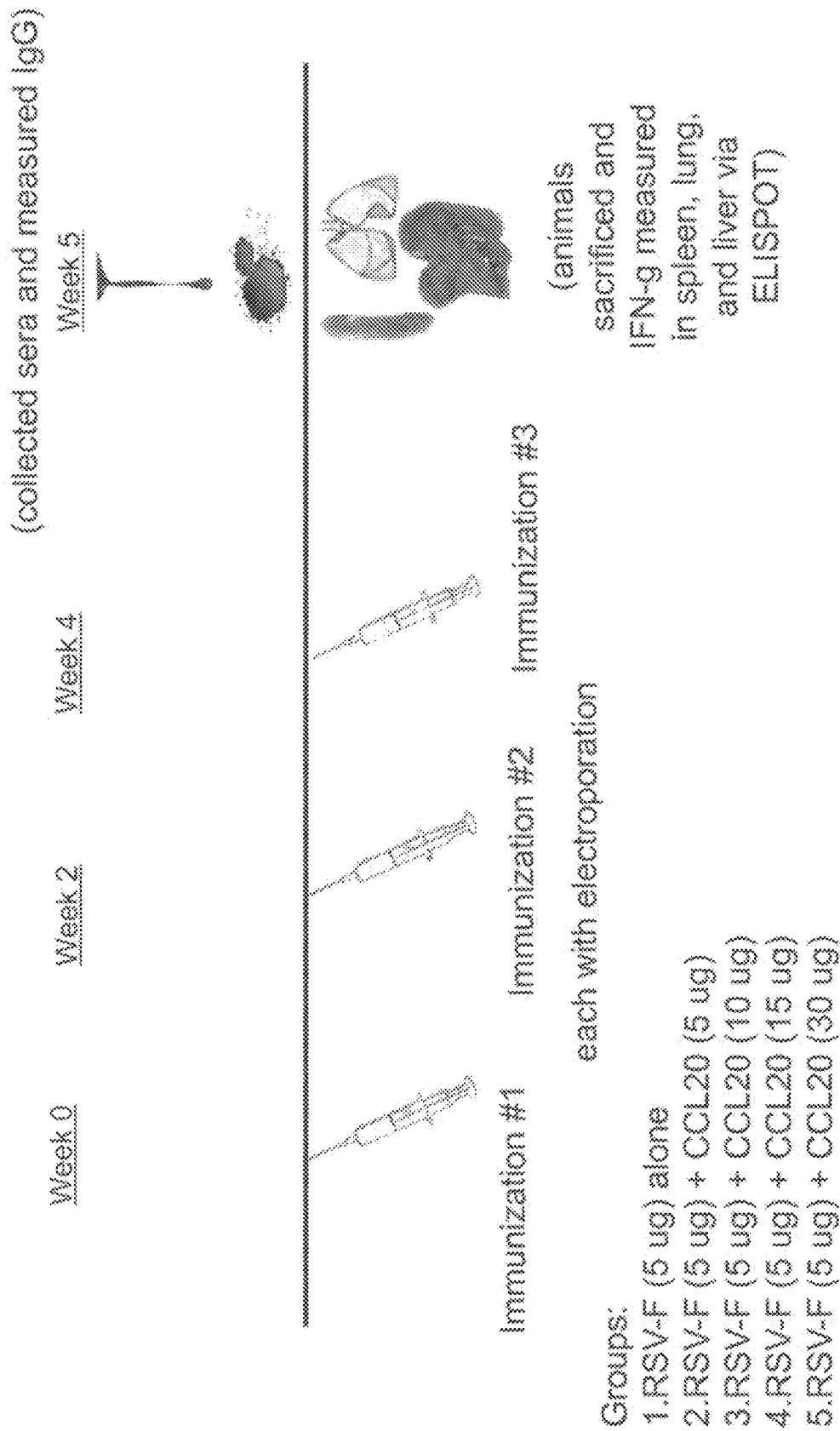
FIG. 19 depicts an immunization schedule for evaluation of the combination of RSV-F vaccine with CCL20.

FIG. 19 depicts an immunization schedule for evaluation of the combination of RSV-F vaccine with CCL20.

Figure 20:
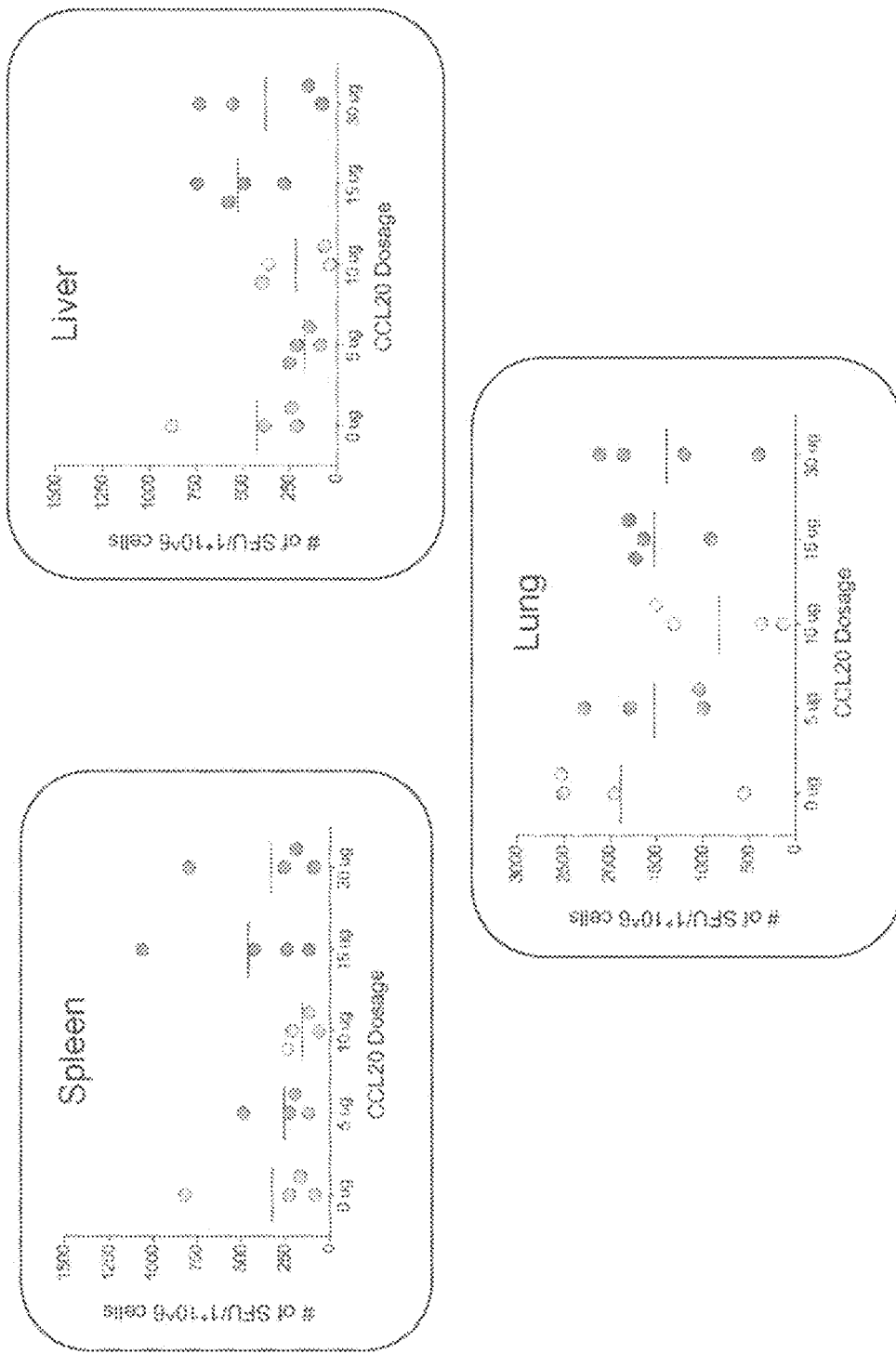
FIG. 20 shows data from the study including data from a comparison of IFN-g production in each of spleen, liver and lung with different dosages of CCL20 at 1 week after last immunization.

FIG. 20 shows data from the study including data from a comparison of IFN-g production in each of spleen, liver and lung with different dosages of CCL20 at 1 week after last immunization.

Figure 21:
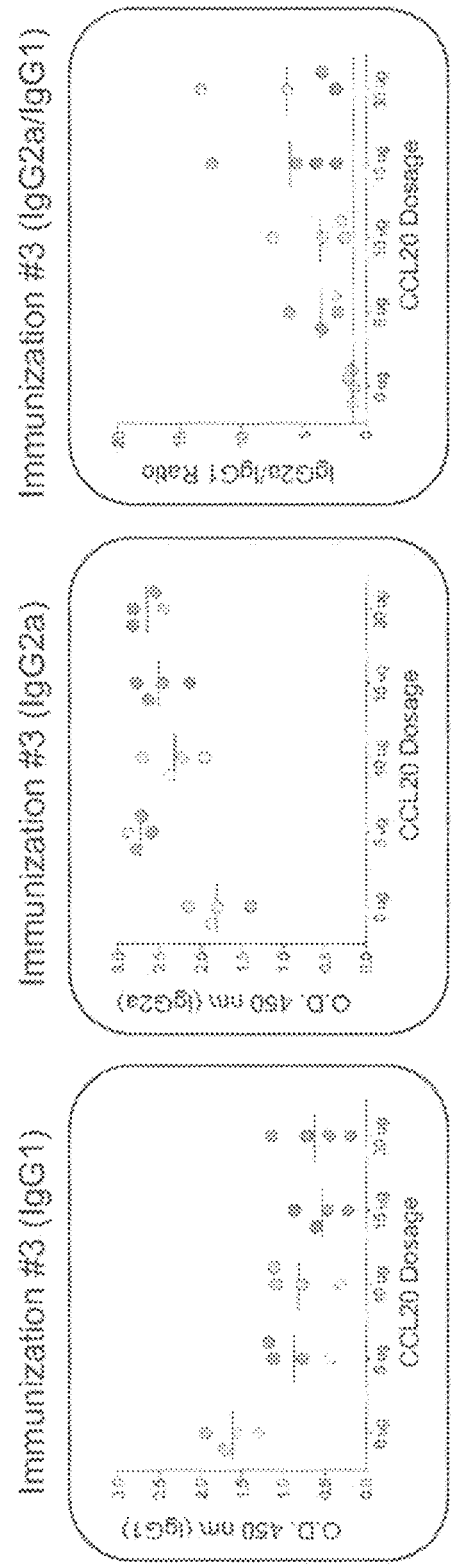
FIG. 21 shows data of a comparison of IgG subtypes (IgG1 vs IgG2a) in Sera.

FIG. 21 shows data of a comparison of IgG subtypes (IgG1 vs IgG2a) in Sera.

Results show that co-immunization with CCL20 does not enhance cell-mediated immune response in both the lung and the liver after RSV-F DNA immunization. CCL20 appeared to bias RSV-F specific IgG antibodies generated after DNA immunization towards a Th1-isotype. Less IgG1 and more IgG2a were observed in sera after CCL20+RSV-F co-immunization compared to RSV-F immunization alone.

Thus, provided are improved vaccines, improved methods for inducing immune such responses, including mucosal immune responses, and for prophylactically and/or therapeutically immunizing individuals against immunogens, particularly those associated with pathogens and other agents which enter the host via mucosal tissue. For examples, infectious agents commonly enter the host across a mucosal tissue such as the oral mucosa and other mucosa of the alimentary canal, the respiratory tract including olfactory and conjunctival mucosa, the mammary glands, and the genitourinary tract.

Composition comprising nucleic acid sequences that encodes an immunogen in combination with nucleic acid sequences that encodes CCL20 and functional fragments thereof are provided. The composition may comprise an isolated nucleic acid molecule that encodes both an immunogen and CCL20 and functional fragments thereof and/or compositions comprising an isolated nucleic acid molecule that encodes an immunogen in combination with an isolated nucleic acid molecule that encodes CCL20 and functional fragments thereof. Such compositions may be provided as injectable pharmaceutical.

The compositions may be used in methods of inducing an immune response in an individual against an immunogen, comprising administering to the individual such a composition.

Recombinant vaccines comprising a nucleotide sequence that encodes an immunogen operably linked to regulatory elements and a nucleotide sequences that CCL20 or functional fragments thereof are provided as are methods of inducing an immune response, including methods of inducing a mucosal immune response, in an individual against an immunogen comprising administering such a recombinant vaccine to an individual.

Live attenuated pathogens comprising a nucleotide sequence that CCL20 or functional fragments thereof, and to methods of inducing an immune response, including methods of inducing a mucosal immune response, in an individual against a pathogen comprising administering the live attenuated pathogen to an individual are also provided.

Methods of inducing an immune response in an individual against an immunogen comprising administering to said individual CCL20 protein or a functional fragment thereof in combination with an isolated nucleic acid molecule that encodes an immunogen; and/or a recombinant vaccine that encodes an immunogen and/or a subunit vaccine that comprises an immunogen and/or a live attenuated vaccine and/or a killed vaccine. Compositions comprising CCL20 protein or a functional fragments thereof in combination with one or more of an isolated nucleic acid molecule that encodes an immunogen; a recombinant vaccine comprising a nucleotide sequence that encodes an immunogen operably linked to regulatory elements; a live attenuated pathogen; and a killed pathogen are provided. As used herein, "functional fragment of CCL20" is meant to refer to a fragment of an iCCl20protein that, when delivered in conjunction with an immunogen, provides an modified immune response compared to the immune response that is induced when the immunogen is delivered without the fragment. Fragments are generally 10 or more amino acids in length. In some embodiments, functional fragments of CCL20 may comprise 20% or more, 25% or more, 30% or more, 35% or more, 40% or more, 45% or more, 50% or more, 55% or more, 60% or more, 65% or more, 70% or more, 75% or more, 80% or more, 85% or more, 90% or more, 91% or more, 92% or more, 93% or more, 94% or more, 95% or more, 96% or more, 97% or more, 98% or more, 99% or more percent of the length of the particular full length CCL20 protein.

When delivered in combination with an immunogen, CCL20 and functional fragments thereof, and combinations thereof modulates immune responses. Accordingly, a combination of these proteins may be delivered as components of a DNA or protein based vaccine in order to induce a therapeutic or prophylactic immune response or in compositions useful to induce an immune response. In some embodiments, the means to deliver the immunogen is a DNA vaccine, a recombinant vaccine, a protein subunit vaccine, an attenuated vaccine or a killed vaccine. In some embodiments, the means to deliver one or more of CCL20 and functional fragments thereof is by expression of coding sequences included in a DNA vaccine, a recombinant vaccine or an attenuated vaccine.

Immune responses result in the production of antigen specific antibodies and/or antigen specific T- and B-cells. Antigen specific antibodies and/or cells provide the means to protect against infection, to reduce or to clear existing infection. They can also be isolated from the individual and used in other applications such as passive immunity protocols, immunocolumns or as reagents.

In some embodiments, CCL20 is useful to induce mucosal immune responses, particularly increased Th1 responses characterized by increased IgG2a responses and decreased IgG1 responses, even in protocols where the composition is delivered systemically. Co-immunization with an immunogen such as by DNA vaccine or other means plasmid plus one or more of these chemokines, such as in a DNA vaccine or part of the coding sequence of another type of vaccine, will provide a unique adjuvanting property.

CCL20 protein and nucleotides which encode it can be obtained from many sources, natural and synthetic. In some embodiments for which protein is used, for example, one having ordinary skill in the art can, using well known techniques, isolates CCL20 protein from natural sources using, for example, immuno columns which contain antibodies that specifically bind to the protein. Alternatively, the protein may be separated using electrophoresis, isolated from the electrophoresis matrix and purified by for example dialysis to yield essentially pure protein. Other well known protein purification technologies can be employed to produce isolated, essentially pure protein. In some embodiments for which protein is used, for example, one having ordinary skill in the art can, using well known techniques, inserts DNA molecules that encode any of CCL20 and functional fragments thereof into a commercially available expression vector for use in well known expression systems. In addition to isolating proteins from natural sources or producing proteins by recombinant techniques, automated peptide synthesizers may also be employed to produce isolated, essentially pure protein.

According to some aspects of the present invention, compositions and methods are provided which prophylactically and/or therapeutically immunize an individual against an immunogen such as an allergen, a pathogen or abnormal, disease-related cells. The vaccine may be any type of vaccine such as, a live attenuated vaccine, a cell vaccine, a recombinant vaccine or a nucleic, acid or DNA vaccine. By delivering nucleic acid molecules that encode an immunogen and one or more of CL20 and functional fragments thereof the immune response induced by the vaccine may be modulated.

Compositions for delivering immunogens and CCL20 are provided, particularly those comprising one or more nucleic acid molecules that comprise a nucleotide sequence that encodes one or more of CCL20 and functional fragments thereof operably linked to regulatory elements in combination with a nucleotide sequence that encodes an immunogen operably linked to regulatory elements. The nucleic acid sequences encoding CCL20 and the immunogen may be one the same molecule or on separate molecules.

The nucleic acid molecules may be delivered using any of several well known technologies including DNA injection (also referred to as DNA vaccination), recombinant vectors such as recombinant adenovirus, recombinant adenovirus associated virus and recombinant vaccinia. In some embodiments, DNA vaccines are constructed as described herein and delivered using electroporation as described herein. The descriptions for RSV vaccines set forth herein, for example, may be applied to the use of CCL20 with other immunogens. DNA vaccines are described in U.S. Pat. Nos. 5,593,972, 5,739,118, 5,817,637, 5,830,876, 5,962,428, 5,981,505, 5,580,859, 5,703,055, 5,676,594, and the priority applications cited therein, which are each incorporated herein by reference. In addition to the delivery protocols described in those applications, alternative methods of delivering DNA are described in U.S. Pat. Nos. 4,945,050 and 5,036,006, which are both incorporated herein by reference. Routes of administration include, but are not limited to, intramuscular, intranasally, intraperitoneal, intradermal, subcutaneous, intravenous, intraarterially, intraocularly and oral as well as topically, transdermally, by inhalation or suppository or to mucosal tissue such as by lavage to vaginal, rectal, urethral, buccal and sublingual tissue. Preferred routes of administration include intramuscular, intraperitoneal, intradermal and subcutaneous injection. In some embodiments, nucleotide sequences that encode CCL20 or functional fragments thereof may be linked to IgE signal peptide. In some embodiments, the immunogen is a pathogen antigen, a cancer-associated antigen or an antigen linked to cells associated with autoimmune diseases. The present invention may be used to immunize an individual against all pathogens such as viruses, prokaryote and pathogenic eukaryotic organisms such as unicellular pathogenic organisms and multicellular parasites. The present invention is particularly useful to immunize an individual against those pathogens which infect cells and which are not encapsulated such as viruses, and prokaryote such as gonorrhea, listeria and shigella. In addition, the present invention is also useful to immunize an individual against protozoan pathogens that include a stage in the life cycle where they are intracellular pathogens. Examples of pathogens include the following. Viruses in the Picornavirus Family Genera such as rhinoviruses (responsible for—50% cases of the common cold). Etheroviruses, (include polioviruses, coxsackieviruses, echoviruses, and human enteroviruses such as hepatitis A virus), and Apthoviruses (Veterinary; target antigens include: VP1, VP2, VP3, VP4, VPG). Viruses in the Calcivirus Family Genera include Norwalk Group of Viruses (causative agent of epidemic gastroenteritis). Viruses of the Togavirus Family Genera include Alphaviruses: (examples include Senilis viruses, RossRiver virus and Eastern & Western, Equine encephalitis). Reovirus include Rubella virus. Flariviridue Family Examples include dengue, yellow fever, Japanese encephalitis, St. Louis encephalitis and tick borne encephalitis viruses. West Nile virus (Genbank NC001563, AF533540, AF404757, AF404756, AF404755, AF404754, AF404753, AF481864, M12294, AF317203, AF196835, AF260969, AF260968, AF260967, AF206518 and AF202541) Representative Target antigens: E NS5 C. Hepatitis C Virus. Coronavirus Family include infectious bronchitis virus, porcine transmissible gastroenteric virus, Porcine hemaglutinating encephalomyelitis virus, Feline infectious peritonitis virus, Feline enteric coronavirus, Canine coronavirus, SARS associated coronavirus, human respiratory coronaviruses cause ~40 cases of common cold. EX. 224E, OC43. Target antigens: E1—also called M or matrix protein E2—also called S or Spike protein E3—also called BE or hemagglutin-elterose glycoprotein N—nucleocapsid. Rhabdovirus Family Genera include Vesiliovirus Lyssavirus such as rabies. Target antigen: G protein N protein. Filoviridue Family includes Hemorrhagic fever viruses such as (Medical) Marburg and Ebola virus. Paramyxovirus Genera includes paramyxovirus: Family such as Mumps virus, New Castle disease virus, Morbillivirus such as Measles, canine distemper, Pneuminvirus such as Respiratory syncytial virus, Orthomyxovirus. The Influenza virus Family includes Bungavirus Family Genera such as bungavirus, California encephalitis, LA Crosse, Phlebovirus such as Rift Valley Fever, Hantavirus such as puremala, a hemahagin fever virus, Nairvirus, unassigned bungaviruses Arenavirus Family LCM, and Lassi fever virus. Reovirus Family Genera includes Reovirus, Rotavirus, Orbiviruses such as Colorado Tick fever, Lebombo, equine encephalosis, blue tongue. Retrovirus Family Sub-Family includes oncorivirinal such as leukemia virus, HTLVI and HTLVII, Lentivirinal such as HIV, feline immunodeficiency virus, equine infections, and anemia virus. Spumavirinal Papovavirus Family Sub-Family includes Polyomaviruses such as BKU and JCU viruses, Sub-Family Papillomavirus. Adenovirus such as EX AD7, ARD, O.B., 275. Parvovirus Family includes Feline parvovirus, Feline panleucopeniavirus, Canine parvovirus, Porcine parvovirus. Herpesvirus Family Sub-Family includes alpha-Genera Simplexvirus herpesviridue HSVI (Genbank X14112, NC001806), HSVII (NC001798) Varicellovinis, pseudorabies, varicella zoster. Sub-Family—beta-includes Genera Cytomegalovirus such as herpesviridue HCMV. Muromegalovirus Sub-Family includes Genera: Lymphocryptovirus, Gamma-EBV—(Burkitts lympho), herpesviridue. Rhadinovirus Poxvirus Family Sub-Family Genera Variola includes (Smallpox) Chordopoxviridue Vaccinia (Cowpox) (Parapoxivirus) Auipoxvirus, Capripoxvirus Leporipoxvirus. Suipoxviru's Sub-Family includes Enternopoxviridue Hepadnavirus, Hepatitis B virus Family Unclassified Hepatitis delta virus. Bacterial pathogens include pathogenic gram-positive cocci such as pneumococcal; staphylococcal; and streptococcal. Pathogenic gram-negative cocci include: meningococcal; and gonococcal. Pathogenic enteric gram-negative bacilli include: enterobacteriaceae; pseudomonas, acinetobacteria and eikenella, melioidosis; sahnonella; shigellosis; hemophilus; chancroid; brucellosis; tularemia; *Yersinia* (*Pasteurella*); *Streptobacillus mortiliformis* and *spirillum; Listeria monocytogenes; Erysipelothrix rhusiopathiae*; diphtheria, cholera, anthrax; donovanosis (granuloma inguinale); and bartonellosis. Pathogenic anaerobic bacteria include: tetanus; botulism; other clostridia; tuberculosis; leprosy; and other mycobacteria. Pathogenic spirochetal diseases include: syphilis;—treponematoses: yaws, pinta and endemic syphilis; and leptospirosis. Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma, and chromomycosis; and dermatophytosis. Rickettsial infections include rickettsial and rickettsioses. Examples of mycoplasma and chlarnydial infections include: *Mycoplasma pneumoniae;* lymphogranuloma venereum; psittacosis; and perinatal chlamydial infections. Pathogenic eukaryotes Pathogenic protozoans and helminths and infections thereby include: amebiasis; malaria; leishmaniasis; trypanosomiasis; toxoplasmosis; *Pneumocystis carinii*; babesiosis; giardiasis; trichinosis; filariasis; schistosomiasis; nematodes; trematodes or flukes; and cestode (tapeworm) infections. Vaccines can be made such as DNA constructs that comprise DNA sequences that encode the peptides that comprise at least an epitope identical or substantially similar to an epitope displayed on a pathogen antigen. In some embodiments, the methods of immunizing an individual against a pathogen are directed against RSV, HIV, HSV, HCV, WNV or HBV.

Methods of conferring a protective immune response against hyperproliferating cells utilize as immunogens proteins that are characteristic in hyperproliferative diseases. These are useful in vaccines and methods of treating individuals suffering from hyperproliferative diseases. Examples of hyperproliferative diseases include all forms of cancer and psoriasis. Examples of target proteins against hyperproliferative diseases include those which are proteins encoded by oncogenes such as myb, myc, fyn, and the translocation gene bcr/abl, ras, src, P53, neu, trk and EGRF. In addition to oncogene products as target antigens, target proteins for anti-cancer treatments and protective regimens include variable regions of antibodies made by B cell lymphomas and variable regions of T cell receptors of T cell lymphomas which, in some embodiments, are also used target antigens for autoimmune disease. Other tumor-associated proteins can be used as target proteins such as proteins that are found at higher levels in tumor cells including the protein recognized by monoclonal antibody 17-IA and folate binding proteins or PSA. Methods of treating individuals suffering from autoimmune diseases and disorders by conferring a broad based protective immune response against targets that are associated with autoimmunity including cell receptors and cells which produce "self"-directed antibodies are also provided. T cell mediated autoimmune diseases include Rheumatoid arthritis (RA), multiple sclerosis (MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells. In RA, several specific variable regions of T cell receptors (TCRs) that are involved in the disease have been characterized. These TCRs include V.beta.-3, V.beta.-14, 20 V.beta.-17 and V.alpha.-17. Thus, vaccination with a DNA construct that encodes at least one of these proteins will elicit an immune response that will target T cells involved in RA. See: Howell, M. D., et al., 1991 Proc. Nat. Acad. Sci. USA 88:10921-10925; Piliard, X., et al, 1991 Science 253:325-329; Williams, W. V., et al., 1992 J Clin. Invest. 90:326-333; each of which is incorporated herein by reference. In MS, several specific variable regions of TCRs that are involved in the disease have been characterized. These TCRs include VfP and V.alpha.-10. Thus, vaccination with a DNA construct that encodes at least one of these proteins will elicit an immune response that will target T cells involved in MS. See: Wucherpfennig, K. W., et al., 1990 Science 248:1016-1019; Oksenberg, J. R., et al, 1990 Nature 345:344-346; each of which is incorporated herein by reference. In scleroderma, several specific variable regions of TCRs that are involved in the disease have been characterized. These TCRs include V.beta.-6, V.beta.-g, V.beta.-14 and V.alpha.-16, V.alpha.-3C, V.alpha.-7, V.alpha.-14, V.alpha.-15, V.alpha.-16, V.alpha.-28 and V.alpha.-2. Thus, vaccination with a DNA construct that encodes at least one of these proteins will elicit an immune response that will target T cells involved in scleroderma. In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information. B cell mediated autoimmune diseases include Lupus (SLE), Grave's disease, myasthenia gravis, autoimmune hemolytic anemia, autoimmune thrombocytopenia, asthma, cryoglobulineinia, primary biliary sclerosis and pernicious anemia. Each of these diseases is characterized by antibodies that bind to endogenous antigens and initiate the inflammatory cascade associated with autoimmune diseases. Vaccination against the variable region of antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information. In the case of SLE, one antigen is believed to be DNA. Thus, in patients to be immunized against SLE, their sera can be screened for anti-DNA antibodies and a vaccine can be prepared which includes DNA constructs that encode the variable region of such anti-DNA antibodies found in the sera. Common structural features among the variable regions of both TCRs and antibodies are well known. The DNA sequence encoding a particular TCR or antibody can generally be found following well known methods such as those described in Kabat, et al 1987 Sequence of Proteins of Immunological Interest U.S. Department of Health and Human Services, Bethesda Md., which is incorporated herein by reference. In addition, a general method for cloning functional variable regions from antibodies can be found in Chaudhary. V. K., et al, 1990 Proc. Natl. Acad Sci. USA 87:1066, which is incorporated herein by reference.

In addition to using expressible forms of CCL20 protein coding sequence to improve DNA vaccines, improved attenuated live vaccines, improved killed vaccines and improved vaccines that use recombinant vectors to deliver foreign genes that encode antigens and well as subunit and glycoprotein vaccines are provided which comprise CCL20 protein or a functional fragment thereof and/or coding sequences that encode CCL20 or a functional fragment thereof. Examples of attenuated live vaccines, those using recombinant vectors to deliver foreign antigens, subunit vaccines and glycoprotein vaccines are described in U.S. Pat. Nos. 4,510,245; 4,797,368; 4,722,848; 4,790,987; 4,920,209; 5,017,487; 5,077,044; 5,110,587; 5,112,749; 5,174,993; 5,223,424; 5,225,336; 5,240,703; 5,242,829; 5,294,441; 5,294,548; 5,310,668; 5,387,744; 5,389,368; 5,424,065; 5,451,499; 5,453,364; 5,462,734; 5,470,734; 5,474,935; 5,482,713; 5,591,439; 5,643,579; 5,650,309; 5,698,202; 5,955,088; 6,034,298; 6,042,836; 6,156,319 and 6,589,529, which are each incorporated herein by reference.

Example 8

Using consensus sequences of RSV immunogens F, G(A) and G(B) provides the basis to obtain neutralizing immune responses. Such advantages make consensus RSV DNA vaccine much more beneficial and potentially more efficacious than any other approaches suggested in the past Major RSV proteins—fusion (F), glycoprotein (Ga), and glycoprotein (Ga) were chosen as targets for new RSV vaccines. As mentioned above, F and G proteins are expressed on the surface and are ideal targets for neutralizing antibodies. A cocktail DNA vaccine was prepared comprising plasmid, that have sequence which encode and express consensus RSV-F, plasmids that have sequence which encode and express consensus RSV-G(A) and plasmids that have sequence which encode and express consensus RSV-G(B). The individual plasmids as well as the cocktail were used in studies. The cocktail vaccine was used in studies with rabbits and non-human primates and the results of those studies show that high levels of neutralizing immune response are induced, indicating that the cocktail vaccine can be used in both prophylactic and therapeutic applications with particular value in protecting against RSV infection.

Figure 22A:
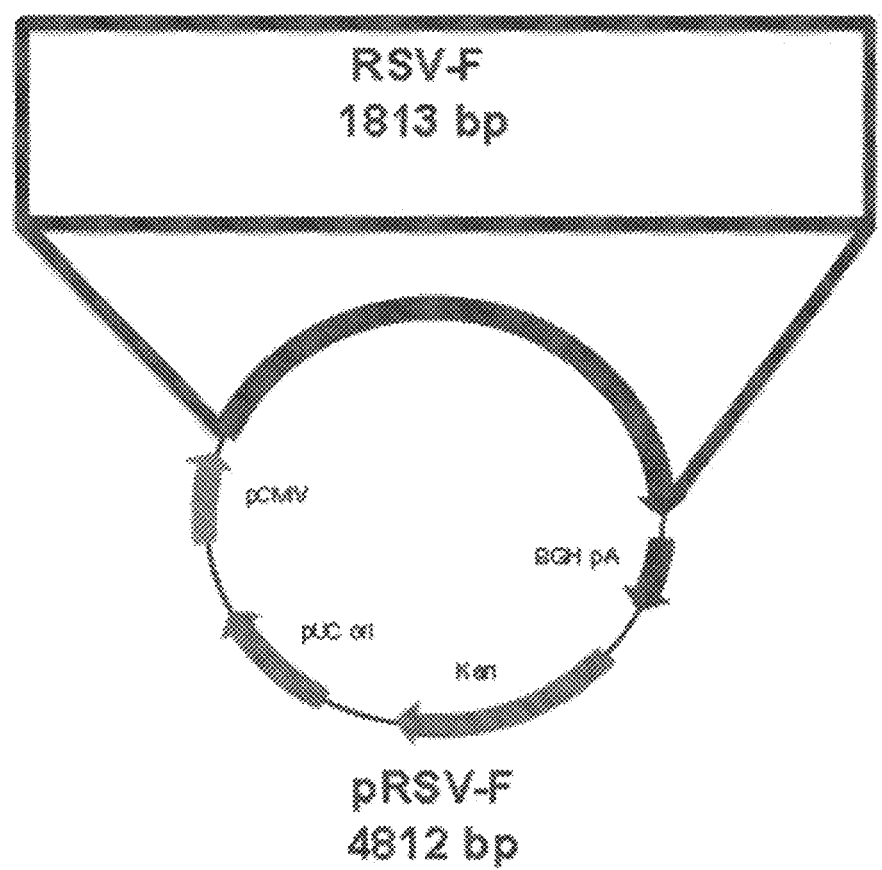

As shown in FIG. 22A, FIG. 22B and FIG. 22C, single insert plasmids for RSV-F, RSV-G(A), and RSV-G(B), respectively, were constructed using the pVAX vector. Consensus sequences for each respective plasmid were cloned into the pVAX vector between the BamHI and XhoI sites. The resulting plasmids were: pRSV-F, which comprises an 1813 base pair insert that encodes consensus RSV-F cloned into pVAX to produce a plasmid having 4812 base pairs; pRSV-G(A), which comprises a 945 base pair insert that encodes consensus RSV-G(A) cloned into pVAX to produce a plasmid having 3944 base pairs; and pRSV-G(B), which comprises a 930 base pair insert that encodes consensus RSV-G(B) cloned into pVAX to produce a plasmid having 3929 base pairs.

Figure 23:
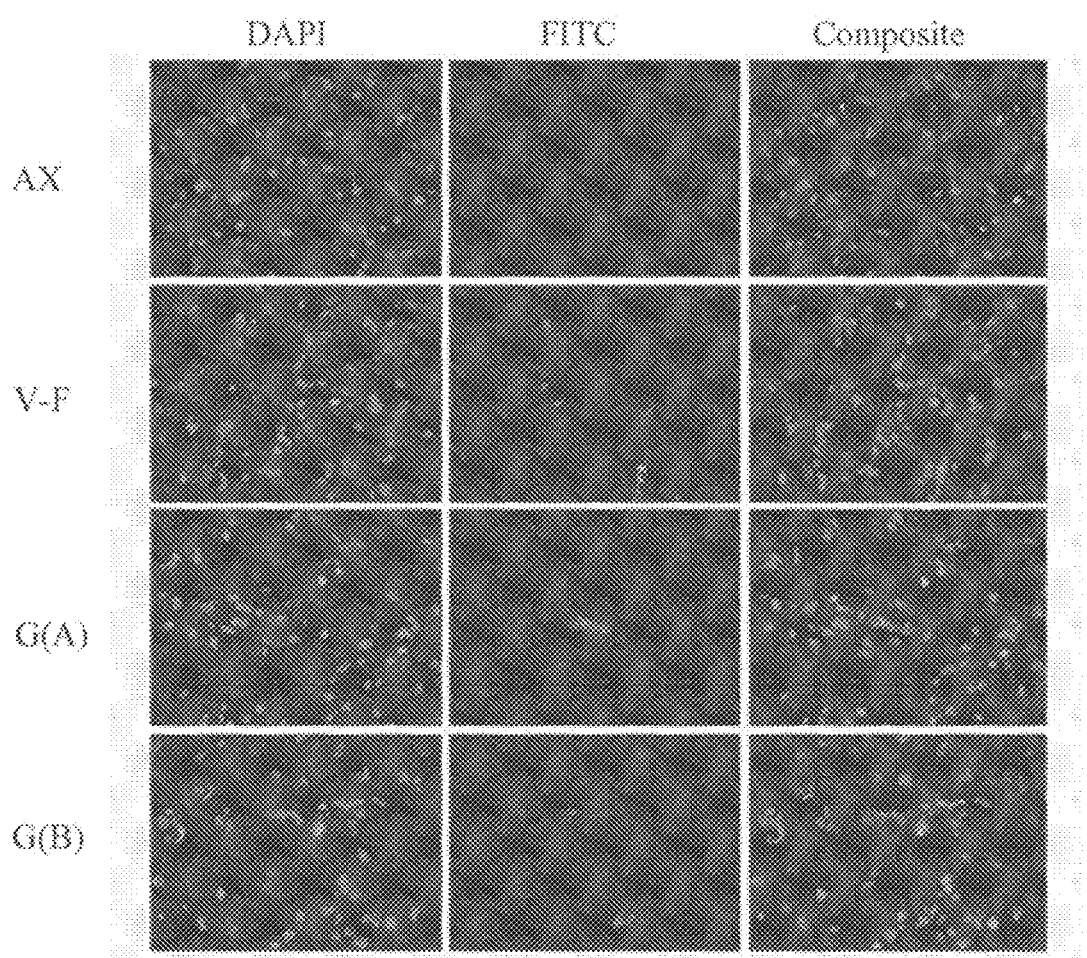
FIG. 23 shows results confirming in vitro expression of RSV-F, RSV-G(A), and RSV-G(B) constructs.

To confirm expression of RSV-F, RSV-G(A), and RSV-G(B) constructs, RD cells were transfected with pRSV-F, pRSV-G(A) and pRSV-G(B), respectively. Immunofluorescent evaluation was performed using immunized, pooled rabbit sera. RSV Immunogens were visualized by immunofluorescence by binding anti-RSV immunogen antibodies chemically conjugated with fluorescein isothiocyanate (FITC). DAPI was used as a nuclear counterstain. Results in FIG. 23 show RD cells transfected with pVAX showed no immunostaining by FITC labeled anti-RSV immunogen antibodies.

Figure 24:
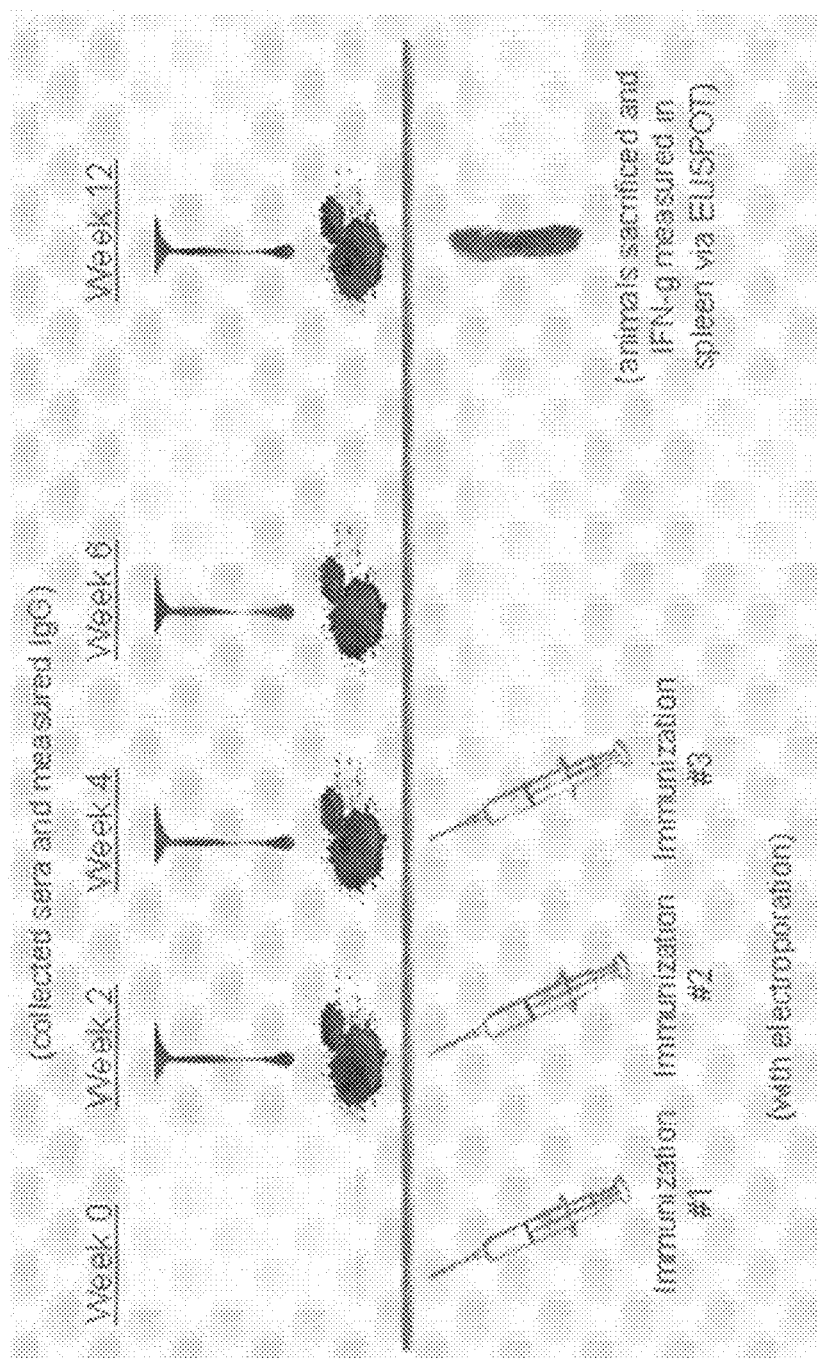
FIG. 24 shows the immunization schedule for an RSV-F Dosage Study.

An RSV-F Dosage Study was done using mice. The immunization schedule is shown in FIG. 24. Five groups of mice were used. Group 1 were control injected with pVAX. Group 2 were injected with 5 µg pRSV-F construct. Group 3 were injected with 15 µg pRSV-F construct. Group 4 were injected with 30 µg pRSV-F construct. Group 5 were injected with 60 µg pRSV-F construct. Animals were immunized a total of three times using electroporation: first immunization at Week 0, second immunization at Week 2 and third immunization at Week 4. Sera was collected and IgG measured a total of four times: first collection at Week 2, second collection at Week 4, third collection at Week 6 and fourth collection at Week 12. Animals were sacrificed at Week 12, spleens were harvested and IFN-gamma was measured via ELISPOT.

Figure 25:
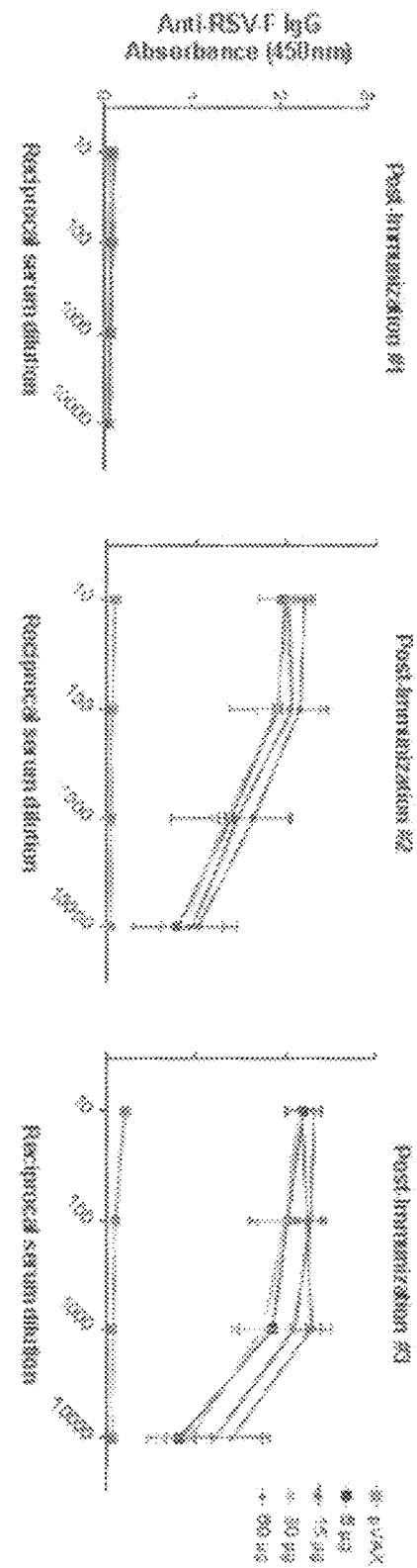
FIG. 25 shows IgG data from RSV-F Dosage Study.

FIG. 25 shows data from the RSV-F Dosage comparing total RSV-F IgG in Sera. Data is shown from sera collected after immunization #1, after immunization #2, and after immunization #3. Anti-RSV-F IgG was measured at reciprocal serum dilutions of 10, 100, 1,000 and 10,000. Data show pVAX did not induce antibodies after any immunization. Data show pRSV-F construct did not induce antibodies after first immunization. Data show pRSV-F construct induced antibodies after second and third immunization.

Figure 26:
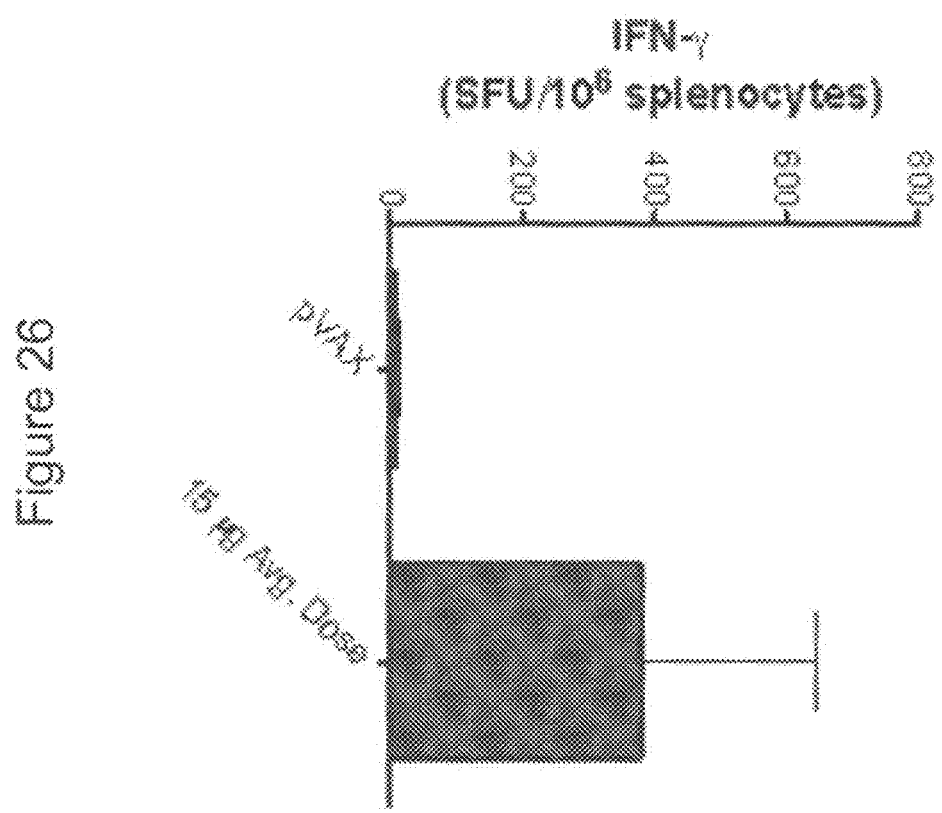
FIG. 26 shows IFN-γ data from RSV-F Dosage Study.

FIG. 26 shows data from the RSV-F Dosage comparing IFN-γ production induced by RSV-F vaccination approximately eight weeks after last immunization. Data is shown comparing IFN-γ production (SFU/106 splenocytes) from animals injected with pVAX and 15 µg average dose pRSV-F construct.

Figure 27:
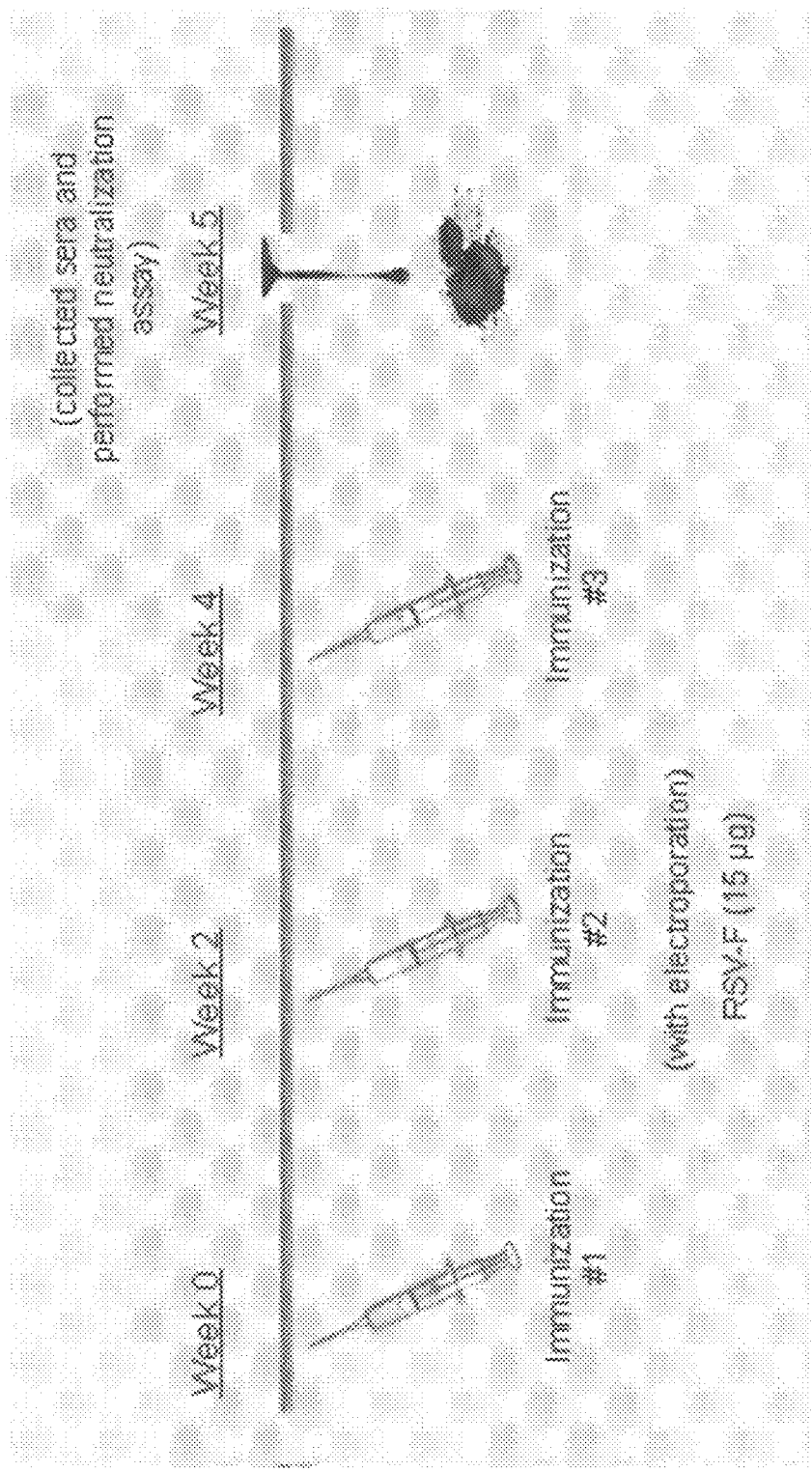
FIG. 27 shows the immunization schedule for a RSV-F PSEUDO Neutralization Study.

An RSV-F PSEUDO Neutralization Study was done using mice. The immunization schedule is shown in FIG. 27. Mice were immunized with 15 µg pRSV-F construct. Animals were immunized a total of three times using electroporation: first immunization at Week 0, second immunization at Week 2 and third immunization at Week 4. Sera was collected and neutralization assay performed at Week 5.

Figure 28:
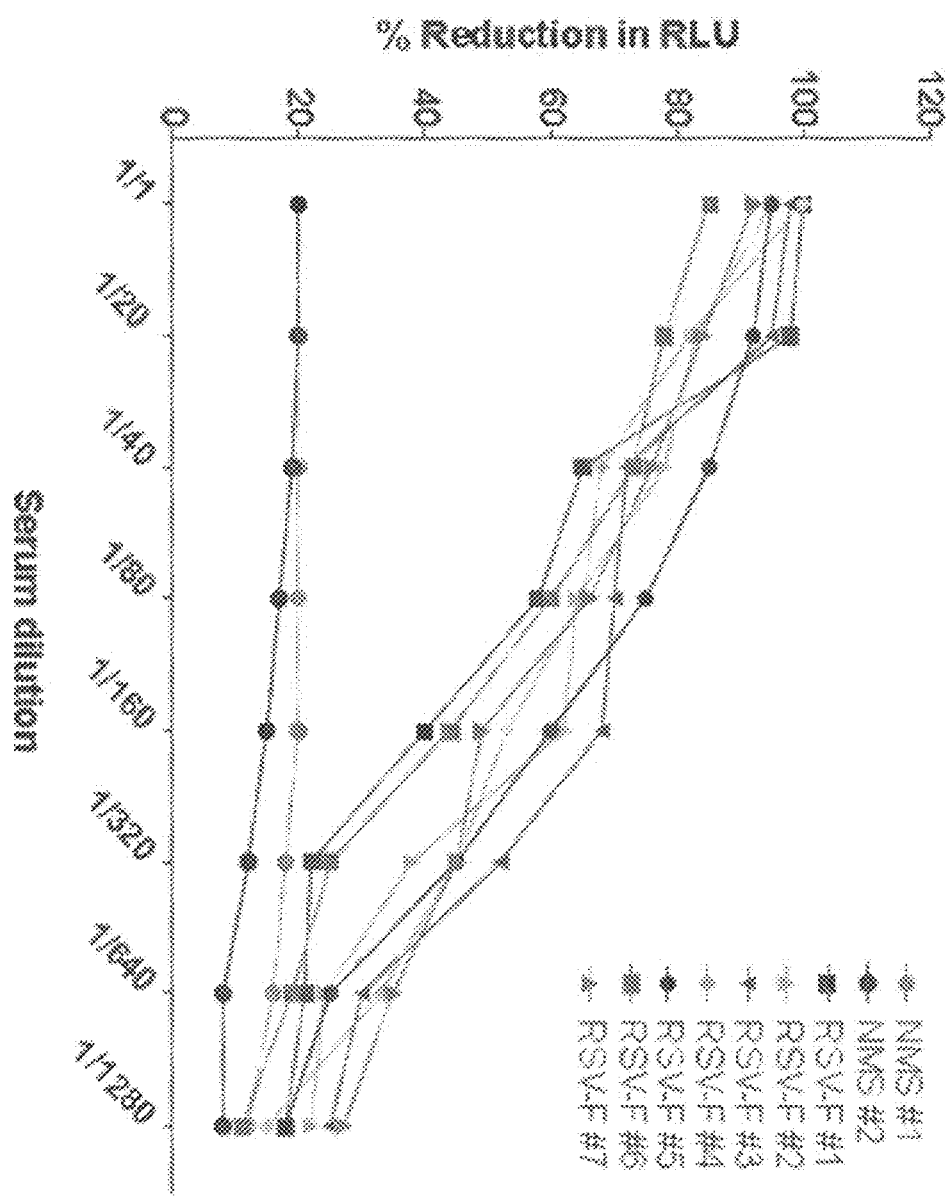
FIG. 28 shows data from the RSV-F PSEUDO Neutralization Study.

Data from the RSV-F PSEUDO Neutralization Study is shown in FIG. 28. RSV-F pseudo-type neutralization activity in TZM-bl HeLa cells was quantified. A comparison of neutralizing ability of RSV-F using luciferase assay from RSV-F immunized serum samples from DNA vaccinated animals that can block the HIV-Luc/RSV-F pseudovirus from entering and infecting target cells. The titer is defined as the reciprocal of the dilution of plasma that produces 50% inhibition of virus. Note the ability of the serum sample from the vaccinated mice to neutralize and block infectivity of HIV-Luc/RSV-F in the absence of such blocking activity in normal mouse serum (NMS).

Figure 29:
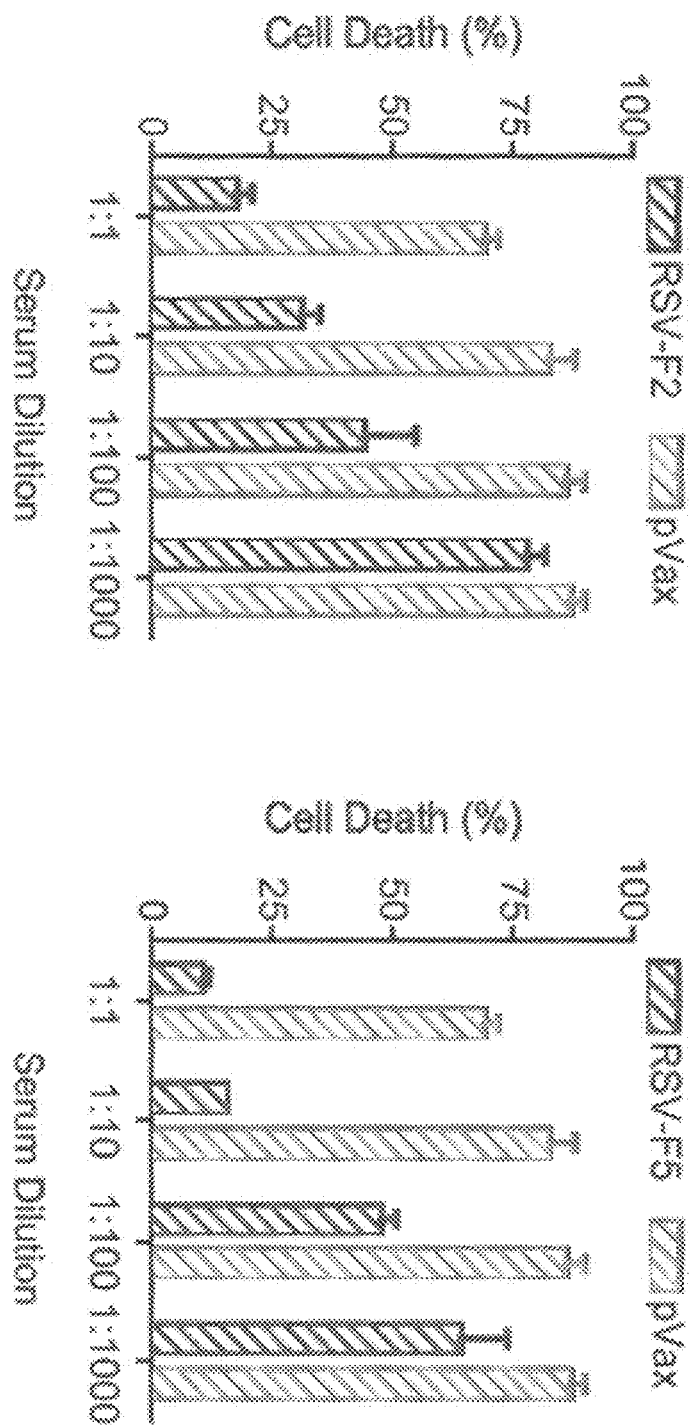
FIG. 29 shows data from two comparisons to determine inhibition of apoptotic cell death activity by RSV-F pseudovirus in HeLa cells.

As shown in FIG. 29, two comparison were done using sera from two animals vaccinated with pRSV-F (RSV-F2 and RSV-F5) versus sera from pVAX vaccinated animals to determine inhibition of apoptotic cell death activity by RSV-F pseudovirus in HeLa cells. For each comparison, sera was diluted 1:1, 1:10, 1:100 and 1:1000. The level of cell death expressed as a percentage was determined showing that sera from animals vaccinated with pRSV-F inhibited apoptotic cell death of HeLa cell exposed to RSV-F pseudovirus in the presence of sera.

An RSV-G(A) and RSV-(B) Dosage Study was done using mice. The immunization schedule is shown in FIG. 30. Six groups of mice were used. Group 1 were control injected with pVAX. Group 2 were injected with 1 µg pRSV-G(A) or pRSV-G(B) construct. Group 3 were injected with 5 µg pRSV-G(A) or pRSV-G(B) construct. Group 4 were injected with 10 µg pRSV-G(A) or pRSV-G(B) construct. Group 5 were injected with 20 µg pRSV-G(A) or pRSV-G(B) construct. Group 6 were injected with 40 µg pRSV-G(A) or pRSV-G(B) construct. Animals were immunized a total of three times using electroporation: first immunization at Week 0, second immunization at Week 2 and third immunization at Week 4. Sera was collected and IgG measured a total of two times: first collection at Week 4, and the second collection at Week 6.

Figure 31:
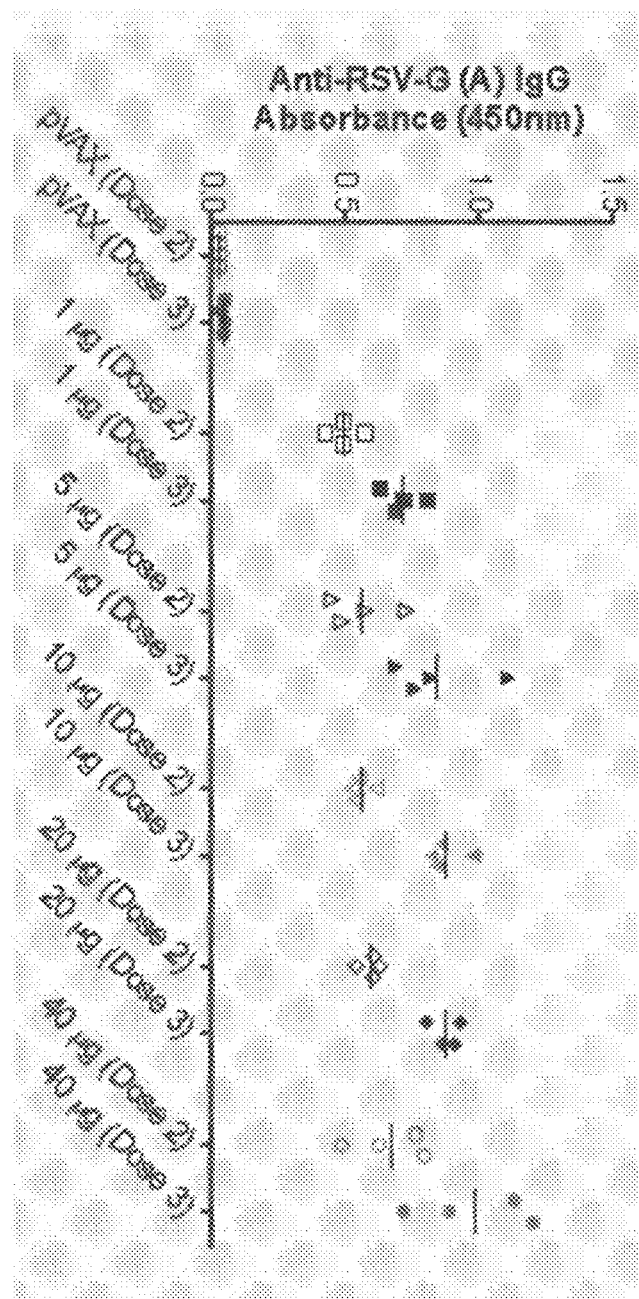
FIG. 31 shows IgG data from RSV-G(A) from the RSV-G(A) and RSV-(B) Dosage Study.

FIG. 31 shows data for IgG in sera after RSV-G(A) DNA immunization in the RSV(A) or RSV-G(B) Dosage Study. Total anti-RSV-G(A) IgG in Sera was measured from the Dosage Study. Data is shown from sera collected at various doses as set out in the x-axis of the graph in FIG. 31. Anti-RSV-G(A) IgG was measured at serum dilution of 1:100.

Figure 32:
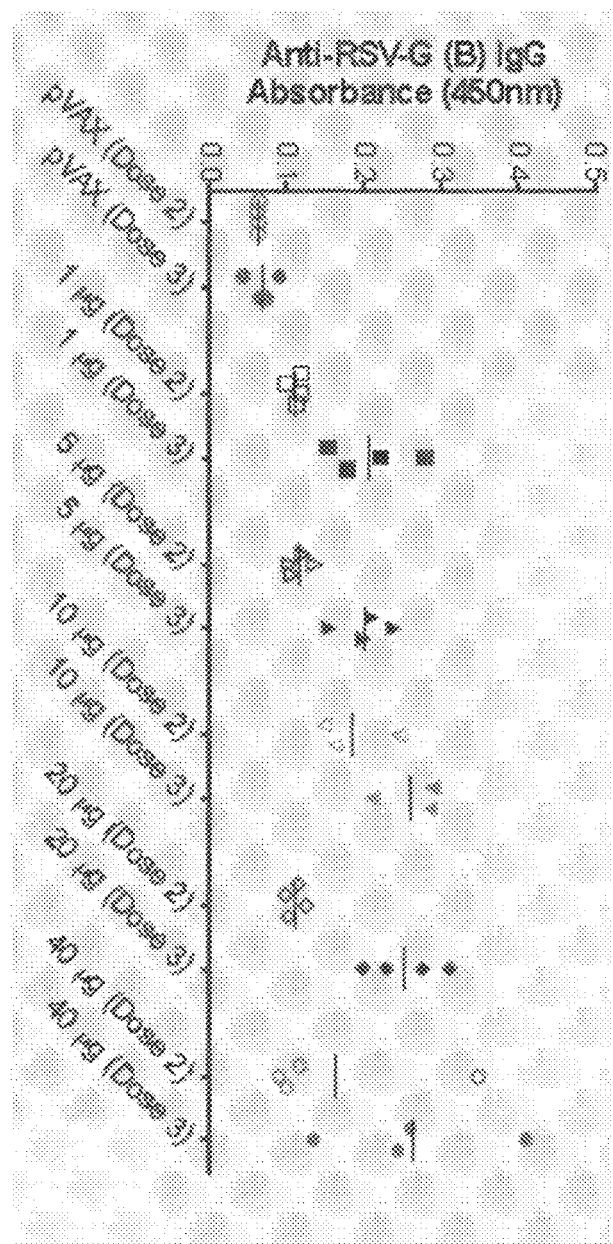
FIG. 32 shows IgG data from RSV-G(A) from the RSV-G(A) and RSV-(B) Dosage Study.

FIG. 32 shows data for IgG in sera after RSV-G(B) DNA immunization in the RSV(A) or RSV-G(B) Dosage Study. Total anti-RSV-G(B)IgG in Sera was measured from the Dosage Study. Data is shown from sera collected at various doses as set out in the x-axis of the graph in FIG. 31. Anti-RSV-G(B) IgG was measured at serum dilution of 1:100.

Figure 33:
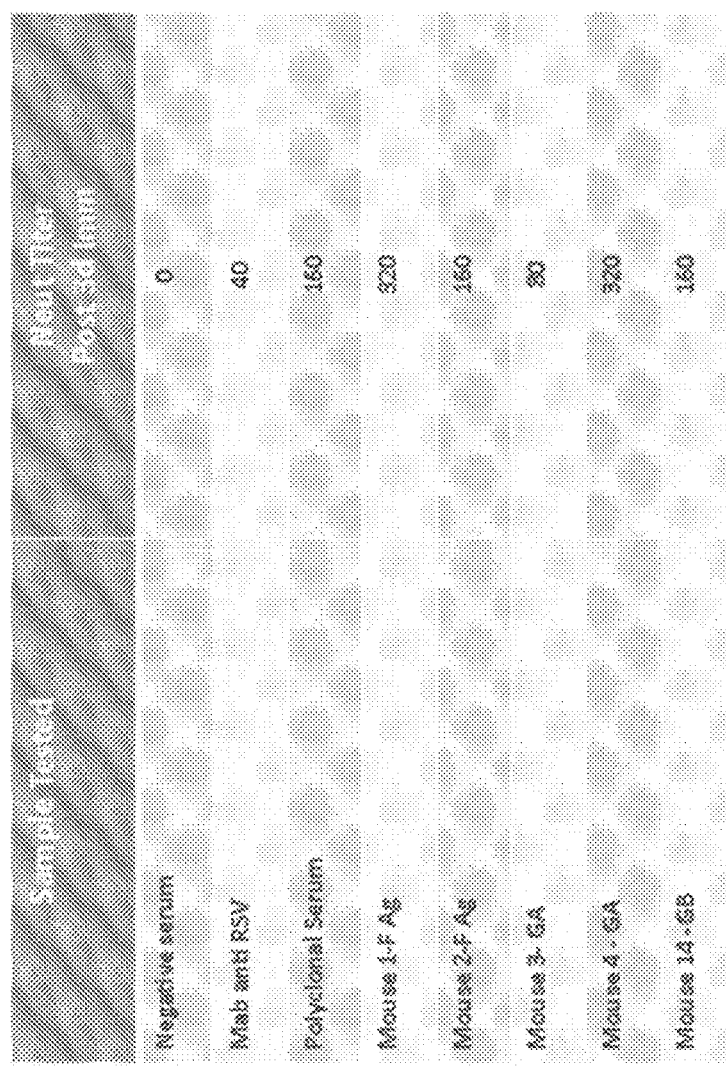
FIG. 33 is a chart showing a summary of RSV Preliminary Neutralization results using Mono Vaccines in Mouse Studies.

FIG. 33 is a chart showing s summary of RSV Preliminary Neutralization results using Mono Vaccines in Mouse Studies. Neutralization titers from sera collected 3 days post immunization were measured. Negative serum was used as a negative control. Positive controls included an anti-RSV monoclonal antibody and anti-RSV polyclonal serum. Neutralization titers were measured for controls and for sera from two mice vaccinated with pRSV-F, two mice vaccinated with pRSV-G(A) and one mouse vaccinated with pRSV-G(B).

Figure 34:
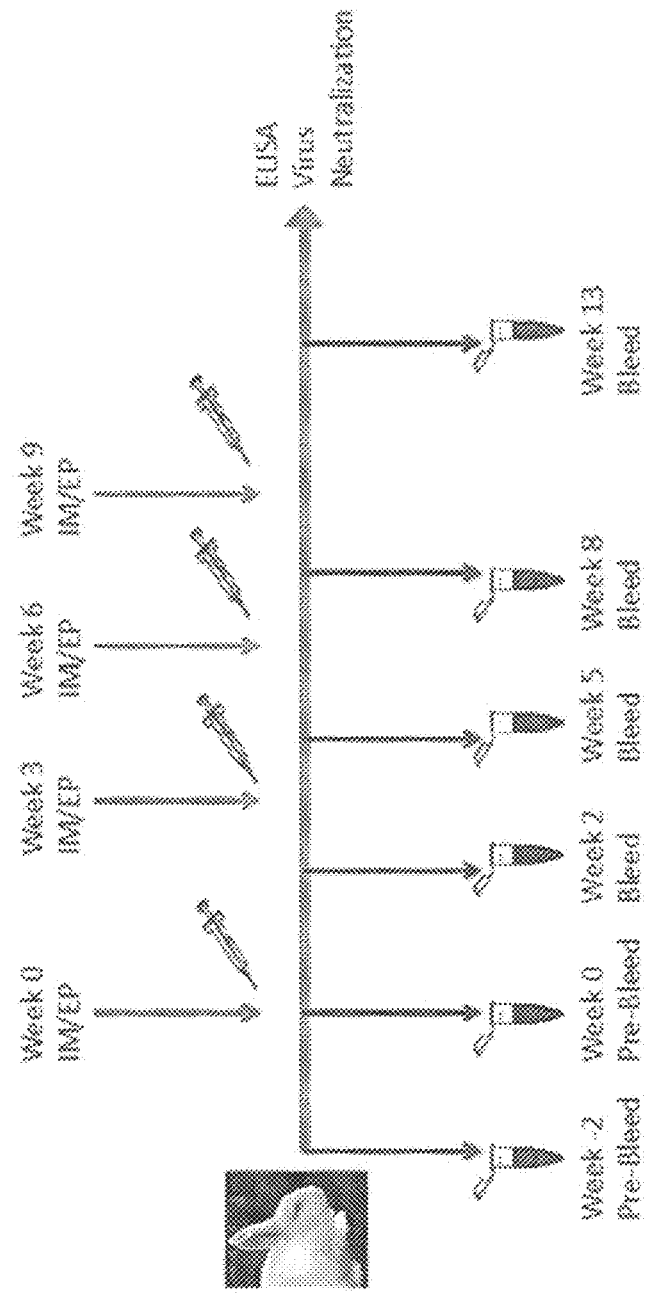
FIG. 34 shows the RSV Rabbit Study Design that was followed.

An RSV Rabbit Study was designed and undertaken. The RSV Rabbit Study Design is shown in FIG. 34. Four female New Zealand white (NZW) rabbits were immunized with a cocktail containing pRSV-F, pRSV-G(A), and pRSV-G(B). Each animal received 200 µg/plasmid in a final 100 µl volume. Animals were immunized a total of four times using intramuscular/electroporation immunization. The first immunization was done at Week 0, the second immunization at Week 3, the third immunization at Week 6 and the fourth at Week 9. Blood was collected from animals six times: Week −2 (Pre-bleed—2 weeks prior to first immunization), Week 0 (Pre-bleed prior to first immunization), Week 2, Week 5, Week 8 and Week 13. Blood was analyzed using ELISA and virus neutralization assays.

Figure 35:
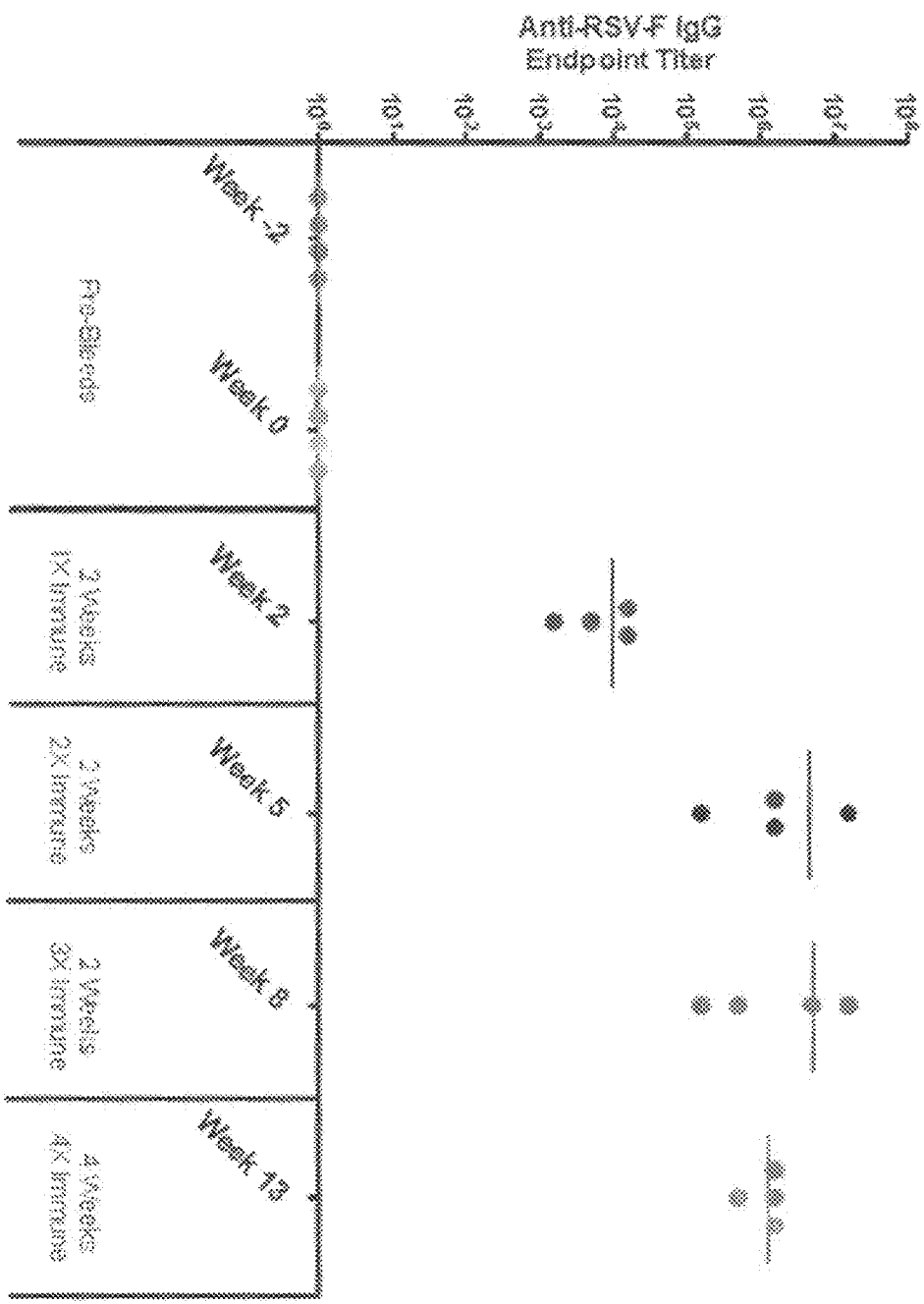
FIG. 35 shows data from the RSV Rabbit Study of measured humoral immunity against RSV-F.

Data from the Rabbit Study is shown in FIG. 35. Humoral immunity against RSV-F was measured. Anti-RSV-F IgG from pre-bleed samples taken at Weeks −2 and 0 and from samples taken at Week 2, at Week 5, at Week 8 and at Week 13. At Week 2, animals from which samples were collected had been immunized one time and the sample was collected 2 weeks post immunization. At Week 5, animals from which samples were collected had been immunized two times and the sample was collected 2 weeks after the second immunization. At Week 8, animals from which samples were collected had been immunized three times and the sample was collected 2 weeks after the third immunization. At Week 13, animals from which samples were collected had been immunized four times and the sample was collected 4 weeks after the fourth immunization.

Figure 36:
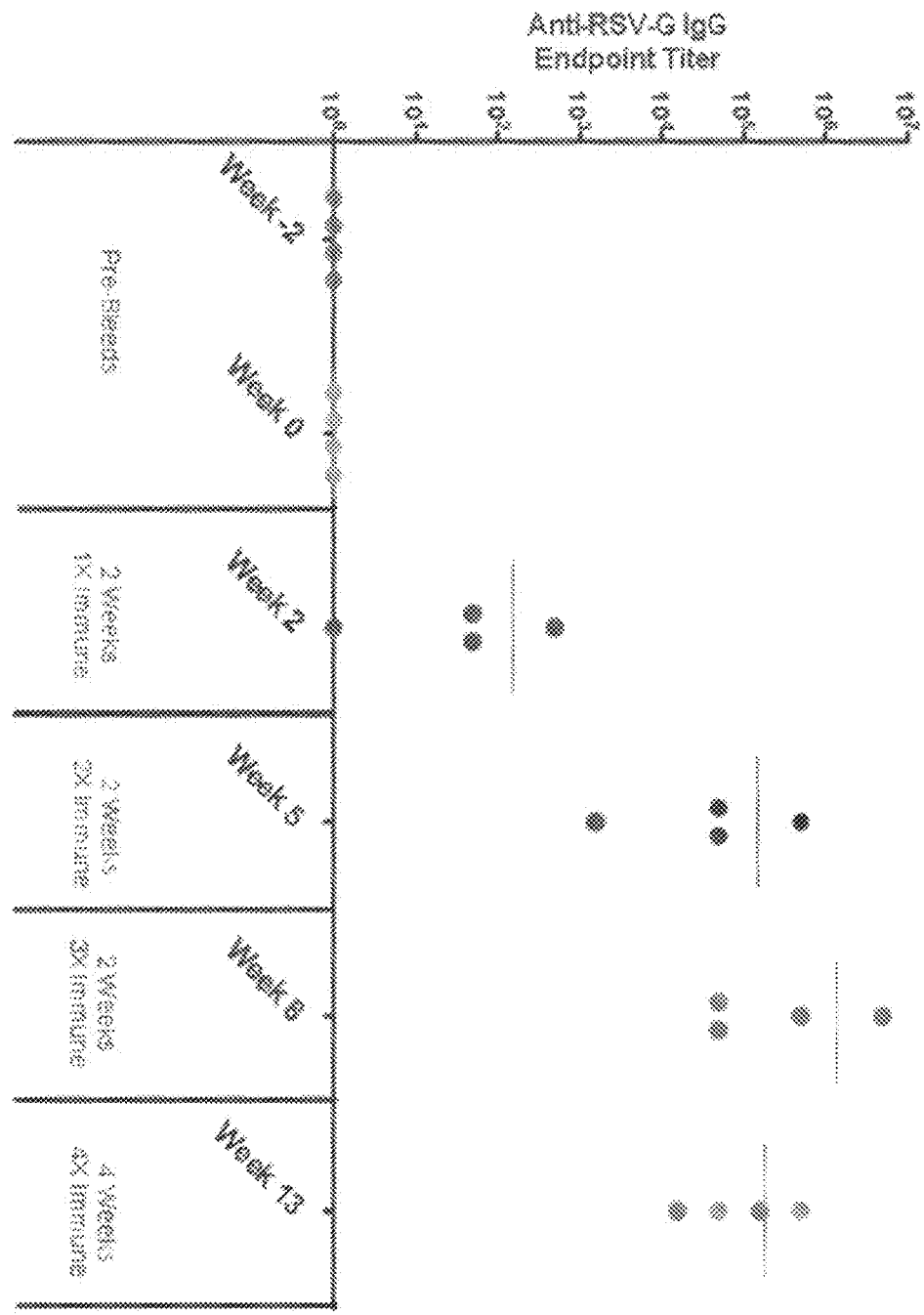
FIG. 36 shows data from the RSV Rabbit Study of measured humoral immunity against RSV-G.

Data from the Rabbit Study is shown in FIG. 36. Humoral immunity against RSV-G was measured. Anti-RSV-G IgG from pre-bleed samples taken at Weeks −2 and 0 and from samples taken at Week 2, at Week 5, at Week 8 and at Week 13. At Week 2, animals from which samples were collected had been immunized one time and the sample was collected 2 weeks post immunization. At Week 5, animals from which samples were collected had been immunized two times and the sample was collected 2 weeks after the second immunization. At Week 8, animals from which samples were collected had been immunized three times and the sample was collected 2 weeks after the third immunization. At Week 13, animals from which samples were collected had been immunized four times and the sample was collected 4 weeks after the fourth immunization.

Figure 37:
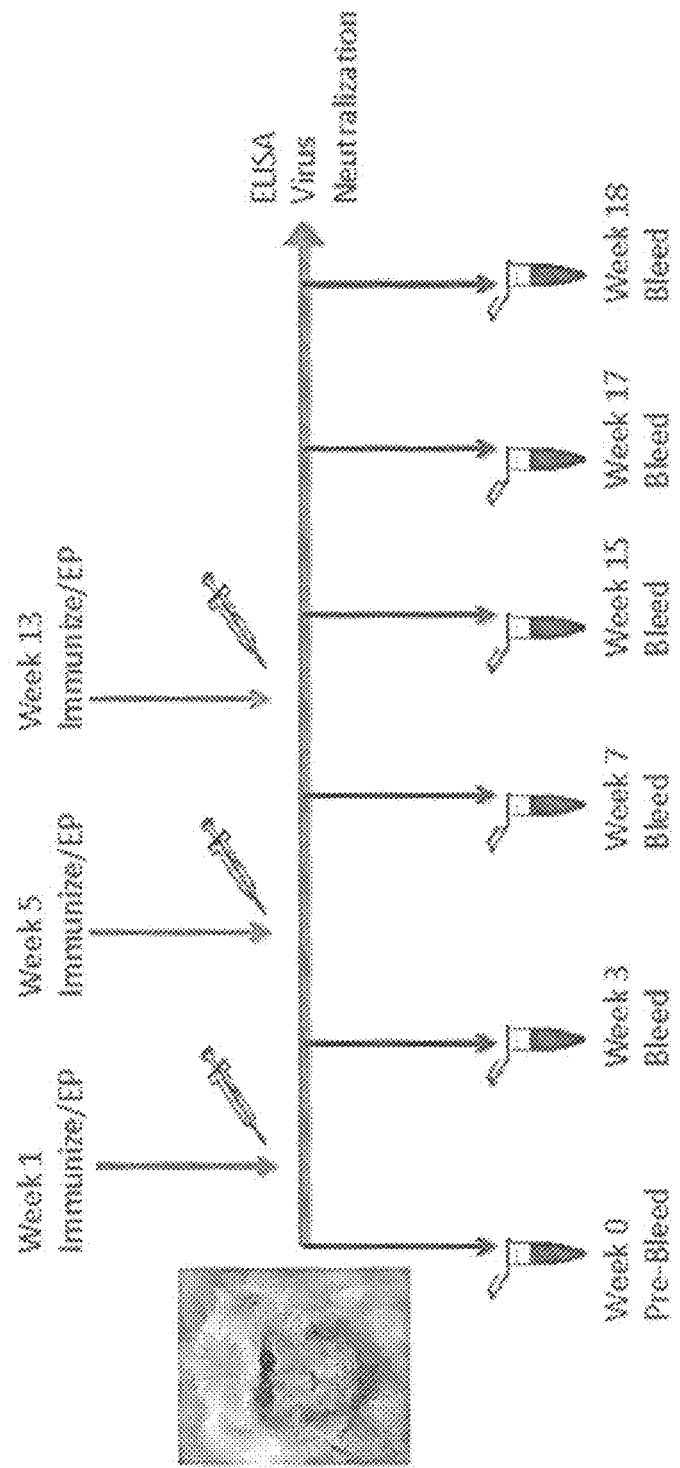
FIG. 37 shows the RSV Non-Human Primate Study Design that was followed.

An RSV Non-human Primate Study was undertaken. The purpose of the study was to evaluate the humoral immunogenicity of the single-insert pDNA RSV vaccines administered as a cocktail in the non-human primate (NHP). Also, the study was used to evaluate and determine whether factors such as multiple site delivery of the vaccine, electroporation method, and delivery with an adjuvant would increase the breadth of the humoral responses. The experiments were performed to determine if the synthetic DNA vaccines against RSV-F, RSV-G(A), and RSV-G(B) stimulate high titer of anti-RSV antibodies, to analyze the specific immune responses in animals vaccinated with the RSV cocktail and to evaluate in the effect of adjuvant and/or multiple site delivery on the immune responses generated. The RSV Non-Human Primate Study Design is shown in FIG. 37. The non-human primate used were Rhesus macaques. In the study, 15 Rhesus macaques were divided into 4 groups: three groups contained four animals each and one group contained three animals. The groups in which n=4 were treated groups, i.e. they were vaccinated. The group in which n=3 was the untreated group which served as a control. The groups were treated as follows.

Group 1 (n=4): each animal was administered a cocktail of 1 mg RSV-F, 1 mg RSV-G(A), 1 mg RSV-G(B), mixed and delivered IM in 1 site.

Group 2 (n=4): each animal was administered a cocktail of 1 mg RSV-F, 1 mg RSV-G(A), 1 mg RSV-G(B), 1 mg rhMEC, mixed and delivered IM in 1 site.

Group 3 (n=4): each animal was administered a cocktail of 1 mg RSV-F, 1 mg RSV-G(A), 1 mg RSV-G(B), mixed and delivered ID in 3 sites.

Group 4 (n=3): each animal was untreated.

Animals were immunized a total of three times using electroporation. The first immunization was done at Week 1, the second immunization at Week 5, and the third immunization at Week 13. Blood was collected from animals six times: Week 0 (Pre-bleed prior to first immunization), Week 3, Week 7, Week 15, Week 17 and Week 18. Blood was analyzed using ELISA and virus neutralization assays.

Figure 38A:
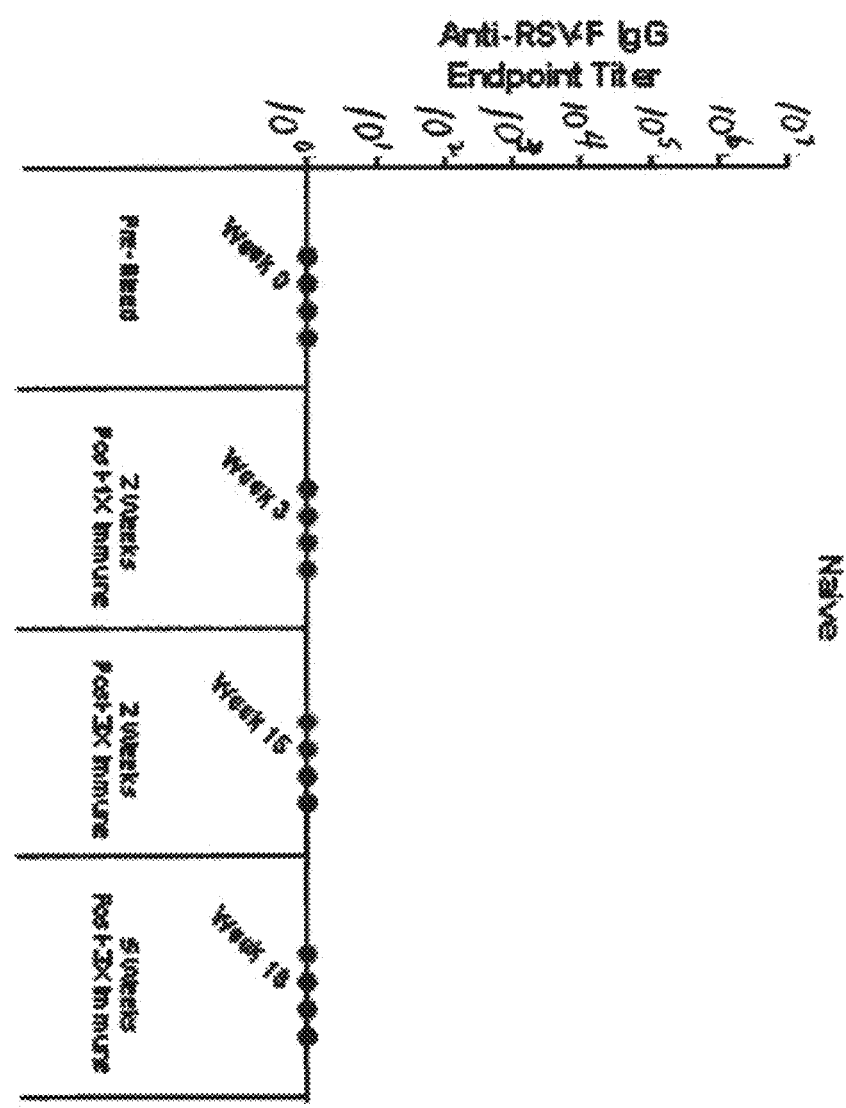
Figure 38B:
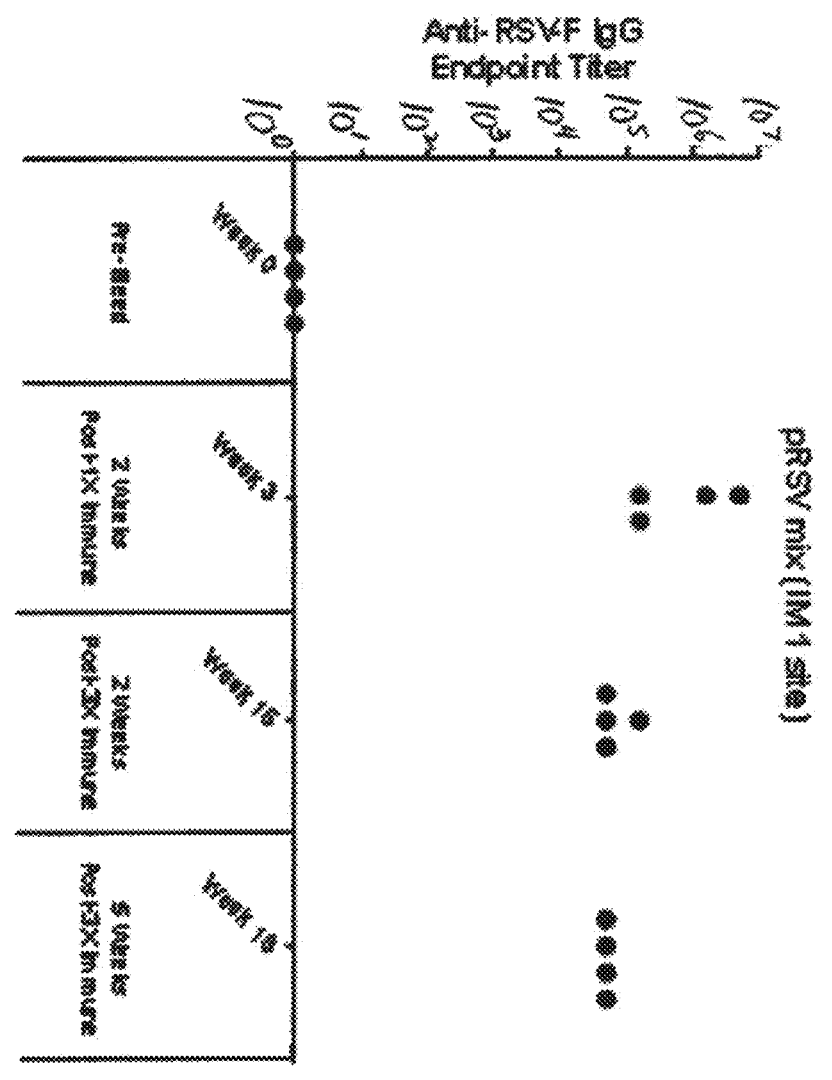
Figure 38C:
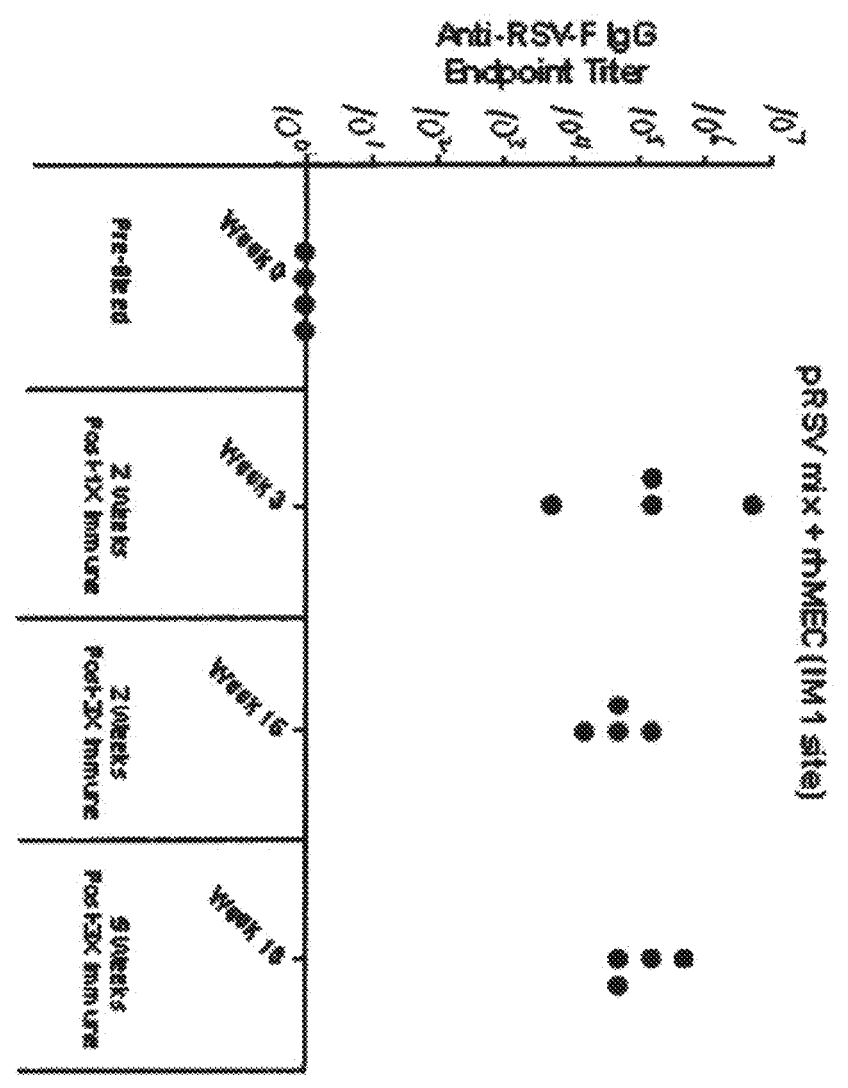
Figure 38D:
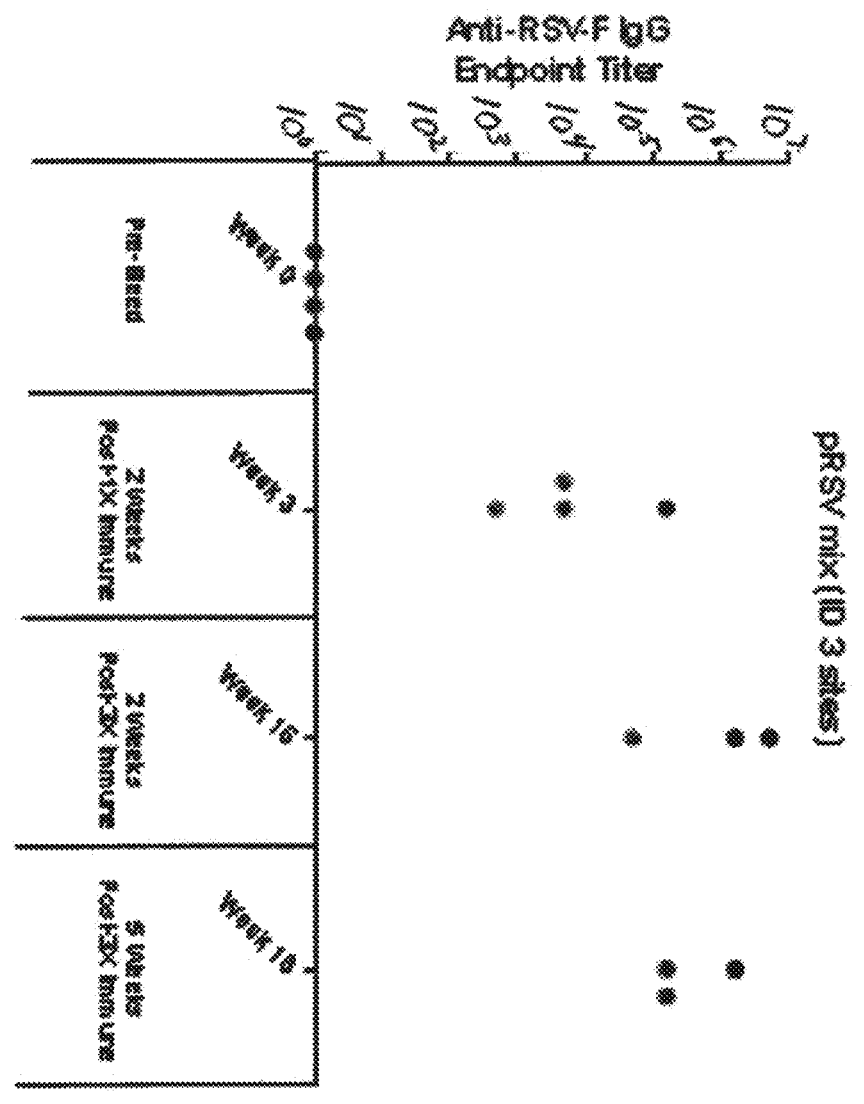

FIG. 38A-38D show data from the RSV Non-Human Primate Study of measured humoral immunity against RSV-F. FIG. 38A shows data from measured humoral immunity against RSV-F in naïve animals. FIG. 38B shows data from measured humoral immunity against RSV-F in animals who received the cocktail vaccine IM at one site. FIG. 38C shows data from measured humoral immunity against RSV-F in animals who received the cocktail vaccine plus rhMEC construct IM at one site. FIG. 38D shows data from measured humoral immunity against RSV-F in animals who received the cocktail vaccine ID at three sites. Anti-RSV-F IgG from pre-bleed samples taken at Week 0 and from samples taken at Week 3, at Week 15 and at Week 18. At Week 3, animals from which samples were collected had been immunized one time and the sample was collected 2 weeks post immunization. At Week 15, animals from which samples were collected had been immunized three times and the sample was collected 2 weeks after the third immunization. At Week 18, animals from which samples were collected had been immunized three times and the sample was collected 5 weeks after the third immunization.

Figure 39A:
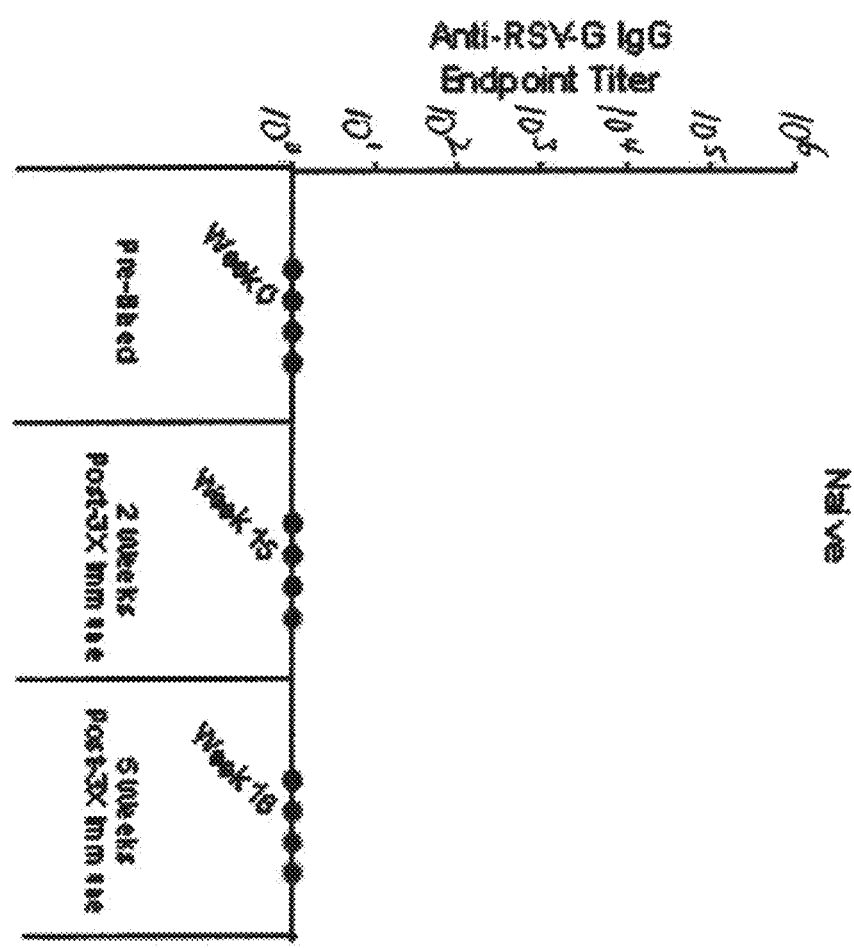
Figure 39C:
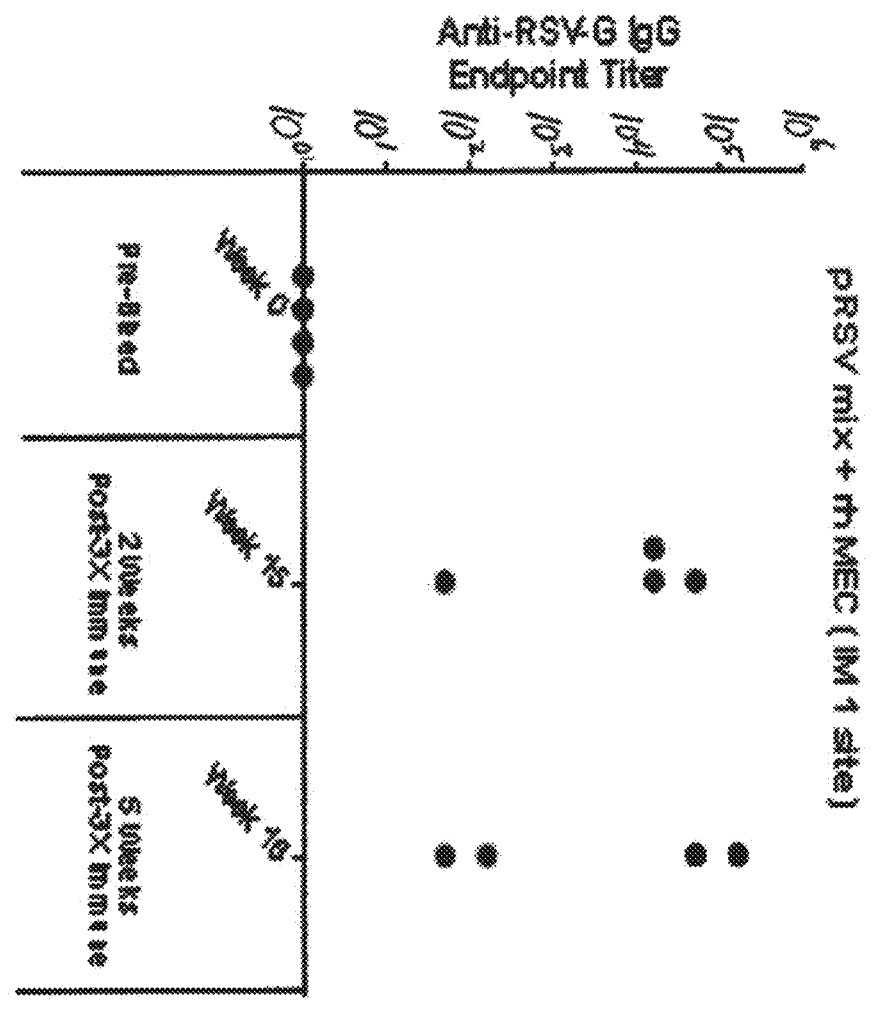

FIG. 39A-39D show data from the RSV Non-Human Primate Study of measured humoral immunity against RSV-G. FIG. 39A shows data from measured humoral immunity against RSV-G in naïve animals. FIG. 39B shows data from measured humoral immunity against RSV-G in animals who received the cocktail vaccine IM at one site. FIG. 39C shows data from measured humoral immunity against RSV-G in animals who received the cocktail vaccine plus rhMEC construct IM at one site. FIG. 39D shows data from measured humoral immunity against RSV-G in animals who received the cocktail vaccine ID at three sites. Anti-RSV-G IgG from pre-bleed samples taken at Week 0 and from samples taken at Week 3, at Week 15 and at Week 18. At Week 3, animals from which samples were collected had been immunized one time and the sample was collected 2 weeks post immunization. At Week 15, animals from which samples were collected had been immunized three times and the sample was collected 2 weeks after the third immunization. At Week 18, animals from which samples were collected had been immunized three times and the sample was collected 5 weeks after the third immunization.

Figure 40:
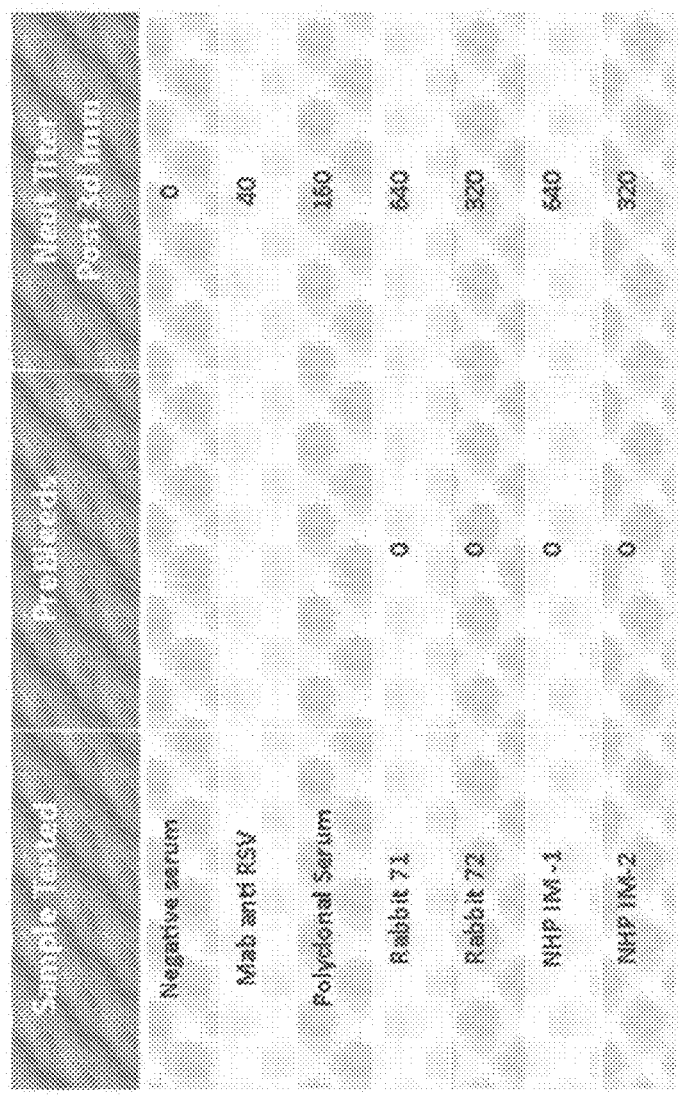
FIG. 40 is a chart showing a summary of RSV Preliminary Neutralization results using cocktail vaccines in Rabbit Non-Human Primate Studies.

FIG. 40 is a chart showing a summary of RSV Preliminary Neutralization results using a cocktail vaccines in Rabbit Non-Human Primate Studies. Neutralization titers from sera collected 3 days post immunization were measured. Negative serum was used as a negative control. Positive controls included an anti-RSV monoclonal antibody and anti-RSV polyclonal serum. Neutralization titers were measured for controls and for sera from two rabbits vaccinated with the cocktail vaccine and two non-human primates vaccinated with the cocktail vaccine. Data from pre-bleeds shows that neutralization titers in the rabbits and the non-human primates were generated post vaccination.

The invention claimed is:

1. A composition comprising a nucleic acid coding sequence that encodes an RSV M2-1 immunogen, wherein the nucleic acid coding sequence that encodes the RSV M2-1 immunogen is selected from the group consisting of:
   a nucleic acid sequence encoding SEQ ID NO:4 and optionally further comprising coding sequence that encodes a signal peptide operably linked to the sequence that encodes SEQ ID NO:4;
   a nucleic acid sequence that encodes a fragment of SEQ ID NO:4 that is at least 120 or more amino acids and optionally further comprising a coding sequence that encodes a signal peptide operably linked to the sequence that encodes the fragment of SEQ ID NO:4; and
   a nucleic acid sequence that encodes a protein that is at least 99% identical to SEQ ID NO:4 and optionally further comprising a coding sequence that encodes a signal peptide operably linked to the coding sequence that encodes the protein that is at least 99% identical to SEQ ID NO:4.

2. The composition of claim 1 comprising a nucleic acid coding sequence that encodes an RSV M2-1 immunogen, wherein the nucleic acid coding sequence that encodes the RSV M2-1 immunogen is selected from the group consisting of:
  a nucleic acid sequence comprising SEQ ID NO:3 and optionally further comprising coding sequence that encodes a signal peptide operably linked to SEQ ID NO:3;
  a nucleic acid sequence comprising a fragment of SEQ ID NO:3 encoding at least 25 or more amino acids and optionally further comprising coding sequence that encodes a signal peptide operably linked to SEQ ID NO:3;
  a nucleic acid sequence at least 98% homologous to SEQ ID NO:3 and optionally further comprises coding sequence that encodes a signal peptide operably linked to coding sequence at least 98% homologous to SEQ ID NO:3; and
  a fragment of a nucleic acid sequence that is at least 98% homologous to SEQ ID NO:3 encoding at least 25 or more amino acids and optionally further comprises coding sequence that encodes a signal peptide operably linked to coding sequence of the fragment of a nucleic acid sequence that is at least 98% homologous to SEQ ID NO:3.

3. The composition of claim 1 comprising a nucleic acid coding sequence that encodes an RSV M2-1 immunogen comprising SEQ ID NO:4 and optionally further comprising coding sequence that encodes a signal peptide operably linked to SEQ ID NO:4.

4. The composition of claim 3 comprising a nucleic acid coding sequence that encodes an RSV M2-1 immunogen, the coding sequence comprising SEQ ID NO:3 and optionally further comprising coding sequence that encodes a signal peptide operably linked to SEQ ID NO:3.

5. The composition of claim 3 comprising a nucleic acid sequence that encodes SEQ ID NO:12.

6. The composition of claim 3 comprising a nucleic acid sequence comprising SEQ ID NO:11.

7. The composition of claim 1 comprising a nucleic acid coding sequence that encodes an RSV M2-1 immunogen comprising a fragment of SEQ ID NO:4 having at least 130 or more amino acids and optionally further comprising a coding sequence that encodes a signal peptide operably linked to SEQ ID NO:4.

8. The composition of claim 7 comprising a nucleic acid coding sequence that encodes an RSV M2-1 immunogen, comprising a fragment of SEQ ID NO:3 encoding at least 130 or more amino acids and optionally further comprising coding sequence that encodes a signal peptide operably linked to SEQ ID NO:3, or a fragment of a nucleic acid sequence that is at least 98% homologous to SEQ ID NO:3 encoding at least 130 or more amino acids and optionally further comprises coding sequence that encodes a signal peptide operably linked to coding sequence of the fragment of a nucleic acid sequence that is at least 98% homologous to SEQ ID NO:3.

9. The composition of claim 1 comprising a nucleic acid coding sequence that encodes an RSV M2-1 immunogen comprising a fragment of SEQ ID NO:4 having at least 165 or more amino acids and optionally further comprising a coding sequence that encodes a signal peptide operably linked to SEQ ID NO:4.

10. The composition of claim 9 comprising a nucleic acid coding sequence that encodes an RSV M2-1 immunogen, comprising a fragment of SEQ ID NO:3 encoding at least 165 or more amino acids and optionally further comprising coding sequence that encodes a signal peptide operably linked to SEQ ID NO:3, or a fragment of a nucleic acid sequence that is at least 98% homologous to SEQ ID NO:3 encoding at least 165 or more amino acids and optionally further comprises coding sequence that encodes a signal peptide operably linked to coding sequence of the fragment of a nucleic acid sequence that is at least 98% homologous to SEQ ID NO:3.

11. The composition of claim 1 comprising a nucleic acid coding sequence that encodes the RSV M2-1 immunogen at least 99% homologous to SEQ ID NO:4 and further comprising a coding sequence that encodes a signal peptide operably linked to coding sequence that encodes the RSV M2-1 immunogen at least 99% homologous to SEQ ID NO:4.

12. The composition of claim 11 comprising nucleic acid coding sequence that encodes the RSV M2-1 immunogen, the coding sequence being at least 99% homologous to SEQ ID NO:3 and optionally further comprises coding sequence that encodes a signal peptide operably linked to coding sequence at least 99% homologous to SEQ ID NO:3.

13. A composition of claim 1 comprising nucleic acid sequences selected from the group consisting of:
  a nucleic acid coding sequence that encodes an RSV M2-1 immunogen,
  a nucleic acid coding sequence that encodes an RSV F immunogen and a nucleic acid coding sequence that encodes an RSV M2-1 immunogen,
  a nucleic acid coding sequence that encodes an RSV M2-1 immunogen and a nucleic acid coding sequence that encodes an RSV Ga immunogen,
  a nucleic acid coding sequence that encodes an RSV M2-1 immunogen and a nucleic acid coding sequence that encodes an RSV Gb immunogen,
  a nucleic acid coding sequence that encodes an RSV F immunogen, a nucleic acid coding sequence that encodes an RSV M2-1 immunogen and a nucleic acid coding sequence that encodes an RSV Ga immunogen,
  a nucleic acid coding sequence that encodes an RSV F immunogen, a nucleic acid coding sequence that encodes an RSV M2-1 immunogen and a nucleic acid coding sequence that encodes an RSV Gb immunogen,
  a nucleic acid coding sequence that encodes an RSV M2-1 immunogen, a nucleic acid coding sequence that encodes an RSV Ga immunogen and a nucleic acid coding sequence that encodes an RSV Gb immunogen, and
  a nucleic acid coding sequence that encodes an RSV F immunogen, a nucleic acid coding sequence that encodes an RSV M2-1 immunogen, a nucleic acid coding sequence that encodes an RSV Ga immunogen and a nucleic acid coding sequence that encodes an RSV Gb immunogen.

14. The composition of claim 1 further comprising a nucleic acid coding sequence that encodes CCL20.

15. The composition of claim 1 formulated for delivery to an individual using electroporation.

16. The composition of claim 1 further comprising nucleic acid sequences that encode one or more proteins selected from the group consisting of: IL-12, IL-15 and IL-28.

17. The composition of claim 1 wherein said one or more nucleic acid coding sequences are part of one or more plasmids.

18. The composition of claim 1 wherein each of the one or more nucleic acid coding sequences are part of incorporated into a separate plasmid.

19. A method of inducing an immune response against RSV comprising administering the composition of claim 3 to an individual in an amount effective to induce an immune response in said individual.

20. A protein selected from the group consisting of: SEQ ID NO:4 and SEQ ID NO:12.

* * * * *

SEQUENCE LISTING

<160> NUMBER OF SEQ ID NOS: 31

<210> SEQ ID NO 1
<211> LENGTH: 1725
<212> TYPE: DNA
<213> ORGANISM: Artificial
<220> FEATURE:
<223> OTHER INFORMATION: Synthetic Sequence

<400> SEQUENCE: 1
gagctgccca tcctgaaaac aaacgccatc accaccatcc tggccgccgt gaccctgtgc      60
ttcgccagca gccagaacat caccgaggaa ttctaccaga gcacctgtag cgccgtgtcc     120

```
aagggctacc tgtctgccct gcggaccggc tggtacacca gcgtgatcac catcgagctg      180
agcaacatca agaaaacaa gtgcaacggc accgacgcca agtgaagct gatcaagcag        240 gaactggaca gtacaagaa cgccgtgacc gagctgcagc tgctgatgca gagcacccct       300
gccgccaaca cagagccag acgcgagctg ccccggttca tgaactacac cctgaacaac       360
accaagaaca ccaacgtgac cctgagcaag aagcggaagc ggcggttcct gggattcctg      420
ctgggcgtgg cagcgccat tgcctctgga atcgctgtgt ctaaggtgct gcacctggaa       480
ggcgaagtga acaagatcaa gtccgccctg ctgagcacca caaggccgt ggtgtccctg       540 agcaacggcg tgtccgtgct gaccagcaag gtgctggatc tgaagaacta catcgacaag     600
cagctgctgc ctatcgtgaa caagcagagc tgcagcatca gcaacatcga gacagtgatc     660
gagttccagc agaagaacaa ccggctgctg gaaatcaccc gcgagttcag cgtgaacgcc     720
ggcgtgacca ccccgtgtc cacctacatg ctgaccaaca gcgagctgct gagcctgatc     780
aacgacatgc ccatcaccaa cgaccagaaa aagctgatga gcaacaacgt gcagatcgtg     840
cggcagcaga gctactccat catgtccatc atcaaagaag aggtgctggc ctacgtggtg      900
cagctgcccc tgtacggcgt gatcgacacc ccctgctgga agctgcacac cagcccctg      960 tgcaccacca caccaaaga gggcagcaac atctgcctga cccggaccga ccggggctgg     1020
tactgcgata tgccggcag cgtgtcattc tttccacagg ccgagacatg caaggtgcag      1080
agcaaccggg tgttctgcga caccatgaac agcctgaccc tgccctccga agtgaacctg     1140
tgcaacatcg acatcttcaa ccctaagtac gactgcaaga tcatgacctc caagaccgac     1200
gtgtccagct ccgtgatcac ctccctgggc gccatcgtgt cctgctacgg caagaccaag     1260
tgcaccgcca gcaacaagaa ccggggcatc atcaagacct cagcaacgg ctgcgactac     1320 gtgtccaaca aggggtgga caccgtgtcc gtgggcaaca ccctgtacta cgtgaacaaa     1380
caggaaggca agagcctgta cgtgaaggc gagcccatca tcaacttcta cgacccctg      1440 gtgttcccca gcgacgagtt cgacgccagc atcagccagg tgaacgagaa gatcaaccag     1500
agcctggcct tcatcagaaa gagcgacgag ctgctgcaca atgtgaatgc cggcaagagc     1560
accaccaata tcatgatcac cacaatcatc atcgtgatca ttgtgatcct gctgtccctg     1620
atcgccgtgg gcctgctgct gtactgcaag gcccggtcca cccctgtgac cctgtccaag     1680
gaccagctga gcggaatcat caacaatatc gccttctcca actga                    1725
```

<210> SEQ ID NO 2
<211> LENGTH: 574
<212> TYPE: PRT
<213> ORGANISM: Artificial
<220> FEATURE:
<223> OTHER INFORMATION: Synthetic Sequence

<400> SEQUENCE: 2

```
Glu Leu Pro Ile Leu Lys Thr Asn Ala Ile Thr Thr Ile Leu Ala Ala
1               5                   10                  15

Val Thr Leu Cys Phe Ala Ser Ser Gln Asn Ile Thr Glu Glu Phe Tyr
            20                  25                  30

Gln Ser Thr Cys Ser Ala Val Ser Lys Gly Tyr Leu Ser Ala Leu Arg
        35                  40                  45

Thr Gly Trp Tyr Thr Ser Val Ile Thr Ile Glu Leu Ser Asn Ile Lys
    50                  55                  60

Glu Asn Lys Cys Asn Gly Thr Asp Ala Lys Val Lys Leu Ile Lys Gln
65                  70                  75                  80
```

-continued

```
Glu Leu Asp Lys Tyr Lys Asn Ala Val Thr Glu Leu Gln Leu Leu Met
                 85                  90                  95
Gln Ser Thr Pro Ala Ala Asn Asn Arg Ala Arg Arg Glu Leu Pro Arg
            100                 105                 110
Phe Met Asn Tyr Thr Leu Asn Asn Thr Lys Asn Thr Asn Val Thr Leu
        115                 120                 125
Ser Lys Lys Arg Lys Arg Arg Phe Leu Gly Phe Leu Leu Gly Val Gly
    130                 135                 140
Ser Ala Ile Ala Ser Gly Ile Ala Val Ser Lys Val Leu His Leu Glu
145                 150                 155                 160
Gly Glu Val Asn Lys Ile Lys Ser Ala Leu Leu Ser Thr Asn Lys Ala
                165                 170                 175
Val Val Ser Leu Ser Asn Gly Val Ser Val Leu Thr Ser Lys Val Leu
            180                 185                 190
Asp Leu Lys Asn Tyr Ile Asp Lys Gln Leu Leu Pro Ile Val Asn Lys
        195                 200                 205
Gln Ser Cys Ser Ile Ser Asn Ile Glu Thr Val Ile Glu Phe Gln Gln
    210                 215                 220
Lys Asn Asn Arg Leu Leu Glu Ile Thr Arg Glu Phe Ser Val Asn Ala
225                 230                 235                 240
Gly Val Thr Thr Pro Val Ser Thr Tyr Met Leu Thr Asn Ser Glu Leu
                245                 250                 255
Leu Ser Leu Ile Asn Asp Met Pro Ile Thr Asn Asp Gln Lys Lys Leu
            260                 265                 270
Met Ser Asn Asn Val Gln Ile Val Arg Gln Gln Ser Tyr Ser Ile Met
        275                 280                 285
Ser Ile Ile Lys Glu Glu Val Leu Ala Tyr Val Val Gln Leu Pro Leu
    290                 295                 300
Tyr Gly Val Ile Asp Thr Pro Cys Trp Lys Leu His Thr Ser Pro Leu
305                 310                 315                 320
Cys Thr Thr Asn Thr Lys Glu Gly Ser Asn Ile Cys Leu Thr Arg Thr
                325                 330                 335
Asp Arg Gly Trp Tyr Cys Asp Asn Ala Gly Ser Val Ser Phe Phe Pro
            340                 345                 350
Gln Ala Glu Thr Cys Lys Val Gln Ser Asn Arg Val Phe Cys Asp Thr
        355                 360                 365
Met Asn Ser Leu Thr Leu Pro Ser Glu Val Asn Leu Cys Asn Ile Asp
    370                 375                 380
Ile Phe Asn Pro Lys Tyr Asp Cys Lys Ile Met Thr Ser Lys Thr Asp
385                 390                 395                 400
Val Ser Ser Ser Val Ile Thr Ser Leu Gly Ala Ile Val Ser Cys Tyr
                405                 410                 415
Gly Lys Thr Lys Cys Thr Ala Ser Asn Lys Asn Arg Gly Ile Ile Lys
            420                 425                 430
Thr Phe Ser Asn Gly Cys Asp Tyr Val Ser Asn Lys Gly Val Asp Thr
        435                 440                 445
Val Ser Val Gly Asn Thr Leu Tyr Tyr Val Asn Lys Gln Glu Gly Lys
    450                 455                 460
Ser Leu Tyr Val Lys Gly Glu Pro Ile Ile Asn Phe Tyr Asp Pro Leu
465                 470                 475                 480
Val Phe Pro Ser Asp Glu Phe Asp Ala Ser Ile Ser Gln Val Asn Glu
                485                 490                 495
Lys Ile Asn Gln Ser Leu Ala Phe Ile Arg Lys Ser Asp Glu Leu Leu
```

```
                500              505              510
His Asn Val Asn Ala Gly Lys Ser Thr Thr Asn Ile Met Ile Thr Thr
            515              520              525

Ile Ile Ile Val Ile Ile Val Ile Leu Leu Ser Leu Ile Ala Val Gly
        530              535              540

Leu Leu Leu Tyr Cys Lys Ala Arg Ser Thr Pro Val Thr Leu Ser Lys
545              550              555              560

Asp Gln Leu Ser Gly Ile Ile Asn Asn Ile Ala Phe Ser Asn
            565              570
```

<210> SEQ ID NO 3
<211> LENGTH: 577
<212> TYPE: DNA
<213> ORGANISM: Artificial
<220> FEATURE:
<223> OTHER INFORMATION: Synthetic Sequence

<400> SEQUENCE: 3

```
agcagacgga acccctgcaa gttcgagatc cggggccact gcctgaacgg caagcggtgc    60
cacttcagcc acaactactt cgagtggccc cctcacgccc tgctggtgcg ccagaacttc   120
atgctgaaca gaatcctgaa gtccatggac aagagcatcg acaccctgag cgagatcagc   180
ggagccgccg agctggaccg gaccgaggaa tatgccctgg gcgtggtggg agtgctggaa   240
agctacatcg gcagcatcaa caacatcacc aagcagagcg cctgcgtggc catgagcaag   300
ctgctgaccg agctgaacag cgacgacatc aagaagctgc gggacaacga ggaacccaac   360
agccccaaga tccgggtgta caacaccgtg atcagctaca tcgagagcaa ccggaagaac   420
aacaagcaga ccatccatct gctgaagcgg ctgcccgccg acgtgctgaa gaaaaccatc   480
aagaacaccc tggacatcca agtccatc accatcaaca ccccaaaga agcaccgtg   540
tccgacacca acgaccacgc caagaacaac gacacca                            577
```

<210> SEQ ID NO 4
<211> LENGTH: 194
<212> TYPE: PRT
<213> ORGANISM: Artificial
<220> FEATURE:
<223> OTHER INFORMATION: Synthetic Sequence

<400> SEQUENCE: 4

```
Ser Arg Arg Asn Pro Cys Lys Phe Glu Ile Arg Gly His Cys Leu Asn
1               5                  10                  15

Gly Lys Arg Cys His Phe Ser His Asn Tyr Phe Glu Trp Pro Pro His
            20                  25                  30

Ala Leu Leu Val Arg Gln Asn Phe Met Leu Asn Arg Ile Leu Lys Ser
        35                  40                  45

Met Asp Lys Ser Ile Asp Thr Leu Ser Glu Ile Ser Gly Ala Ala Glu
    50                  55                  60

Leu Asp Arg Thr Glu Glu Tyr Ala Leu Gly Val Val Gly Val Leu Glu
65                  70                  75                  80

Ser Tyr Ile Gly Ser Ile Asn Asn Ile Thr Lys Gln Ser Ala Cys Val
            85                  90                  95

Ala Met Ser Lys Leu Leu Thr Glu Leu Asn Ser Asp Asp Ile Lys Lys
            100                 105                 110

Leu Arg Asp Asn Glu Glu Pro Asn Ser Pro Lys Ile Arg Val Tyr Asn
        115                 120                 125

Thr Val Ile Ser Tyr Ile Glu Ser Asn Arg Lys Asn Asn Lys Gln Thr
```

```
            130                 135                 140
Ile His Leu Leu Lys Arg Leu Pro Ala Asp Val Leu Lys Lys Thr Ile
145                 150                 155                 160

Lys Asn Thr Leu Asp Ile His Lys Ser Ile Thr Ile Asn Asn Pro Lys
                165                 170                 175

Glu Ser Thr Val Ser Asp Thr Asn Asp His Ala Lys Asn Asn Asp Thr
                180                 185                 190

Thr Gly

<210> SEQ ID NO 5
<211> LENGTH: 894
<212> TYPE: DNA
<213> ORGANISM: Artificial
<220> FEATURE:
<223> OTHER INFORMATION: Synthetic Sequence

<400> SEQUENCE: 5
tccaagaata aggatcagag gaccgcgaaa acgcttgaga ggacgtggga cacgctgaac      60
cacctcctgt tcatctcctc gtgtctctac aagctcaacc ttaagtccat cgcgcagatc    120
accttgagca ttctcgccat gatcatctcc accagcctta tcattgccgc aatcatcttc    180
atcgcatccg ccaaccataa ggtgacattg actacagcga ttatccaaga cgctactagc    240
cagatcaaga ataccacgcc gacctatttg acgcaaaatc ctcagttggg aattagcttc    300
tcgaatctct cggaaaccac gtcgcagccg actacaattc ttgcgtcaac gactccatcg    360
gccaaatcaa caccacaatc gactaccgta aaaacgaaga acacgactac aacacagatt    420
cagccttcaa agcccacgac caaacagaga cagaataagc cgcccaacaa gcccaacaat    480
gattttcact tcgaggtgtt taacttcgtg ccctgttcga tttgcagcaa taaccccacg    540
tgctgggcga tttgcaagcg aatcccgaat aagaagcccg ggaaaaagac cacgacgaaa    600
ccgacaaaga agccgacaat caagacaacg aaaaaggatc ttaaacctca gacgacaaag    660
cctaaggaag tcttgacaac gaagcctacg gaaaaaccca ctatcaatac taccaagact    720
aacatccgga caaacactgc tgacgagcaat accacgggaa acccggagct cacatcgcag    780
aaagagacac tccattcgac atcctccgag ggtaaccctt cgcccagcca ggtgtatacg    840
acgtcagaat accctagcca accctcatcg ccctcaaata cgacccggca atga           894

<210> SEQ ID NO 6
<211> LENGTH: 297
<212> TYPE: PRT
<213> ORGANISM: Artificial
<220> FEATURE:
<223> OTHER INFORMATION: Synthetic Sequence

<400> SEQUENCE: 6

Ser Lys Asn Lys Asp Gln Arg Thr Ala Lys Thr Leu Glu Arg Thr Trp
1               5                   10                  15

Asp Thr Leu Asn His Leu Leu Phe Ile Ser Ser Cys Leu Tyr Lys Leu
                20                  25                  30

Asn Leu Lys Ser Ile Ala Gln Ile Thr Leu Ser Ile Leu Ala Met Ile
            35                  40                  45

Ile Ser Thr Ser Leu Ile Ile Ala Ala Ile Ile Phe Ile Ala Ser Ala
        50                  55                  60

Asn His Lys Val Thr Leu Thr Thr Ala Ile Ile Gln Asp Ala Thr Ser
65                  70                  75                  80

Gln Ile Lys Asn Thr Thr Pro Thr Tyr Leu Thr Gln Asn Pro Gln Leu
```

```
                    85                  90                  95
Gly Ile Ser Phe Ser Asn Leu Ser Glu Thr Thr Ser Gln Pro Thr Thr
                100                 105                 110

Ile Leu Ala Ser Thr Thr Pro Ser Ala Lys Ser Thr Pro Gln Ser Thr
            115                 120                 125

Thr Val Lys Thr Lys Asn Thr Thr Thr Gln Ile Gln Pro Ser Lys
        130                 135                 140

Pro Thr Thr Lys Gln Arg Gln Asn Lys Pro Pro Asn Lys Pro Asn Asn
145                 150                 155                 160

Asp Phe His Phe Glu Val Phe Asn Phe Val Pro Cys Ser Ile Cys Ser
                165                 170                 175

Asn Asn Pro Thr Cys Trp Ala Ile Cys Lys Arg Ile Pro Asn Lys Lys
            180                 185                 190

Pro Gly Lys Lys Thr Thr Thr Lys Pro Thr Lys Pro Thr Ile Lys
        195                 200                 205

Thr Thr Lys Lys Asp Leu Lys Pro Gln Thr Thr Lys Pro Lys Glu Val
210                 215                 220

Leu Thr Thr Lys Pro Thr Glu Lys Pro Thr Ile Asn Thr Thr Lys Thr
225                 230                 235                 240

Asn Ile Arg Thr Thr Leu Leu Thr Ser Asn Thr Thr Gly Asn Pro Glu
                245                 250                 255

Leu Thr Ser Gln Lys Glu Thr Leu His Ser Thr Ser Ser Glu Gly Asn
            260                 265                 270

Pro Ser Pro Ser Gln Val Tyr Thr Thr Ser Glu Tyr Pro Ser Gln Pro
        275                 280                 285

Ser Ser Pro Ser Asn Thr Thr Arg Gln
        290                 295

<210> SEQ ID NO 7
<211> LENGTH: 876
<212> TYPE: DNA
<213> ORGANISM: Artificial
<220> FEATURE:
<223> OTHER INFORMATION: Synthetic Sequence

<400> SEQUENCE: 7
agcaaaaaca aaaccaaag  gacggctcgg acgcttgaga aaacatggga cacgcttaat    60
caccttattg tgatctcatc gtgtttgtac cggttgaatc tcaagagcat cgcccagatt   120
gcgctgtcag tcctggccat gattatctcg acatcactca tcatcgcagc catcatcttt   180
atcatttcag cgaatcacaa ggtaacgctt acaacagtca cggtgcagac catcaagaat   240
cataccgaaa agaatatcac aacctacctc acccaagtca gcccggagag agtaagcccc   300
tcaaaacagc ctactacgac acctcccatc cacacgaact cggcgaccat ctcaccgaat   360
accaaatcag aaacgcatca tacgaccgca cagacaaagg gacgaaccac tacacccaca   420
cagaacaaca aacccagcac caagccgagg ccaaagaatc cgcccaagaa gccgaaagat   480
gactatcact ttgaagtgtt caacttcgta ccgtgttcga tttgcgggaa taatcagttg   540
tgcaaatcca tttgcaagac gatcccatcc aacaaaccga agaagaaacc taccatcaag   600
cccacaaaca agccaacgac aaaaacaacg aacagcgcg  atcccaaaac gctcgcgaaa   660
acgttgaaga aggaaacgac gacaaaccct acgaagaaac ccacgcccaa gaccactgag   720
agagacacct ccacctcgca atcgacggta cttgacacga ctacgagcaa gcacactatc   780
cagcaacagt ccctgcactc aaccacgccc gagaatacac caaactcaac acagactccg   840
```
acagcttcag agccttccac ttcgaattcc acatga        876

<210> SEQ ID NO 8
<211> LENGTH: 291
<212> TYPE: PRT
<213> ORGANISM: Artificial
<220> FEATURE:
<223> OTHER INFORMATION: Synthetic Sequence

<400> SEQUENCE: 8

```
Ser Lys Asn Lys Asn Gln Arg Thr Ala Arg Thr Leu Glu Lys Thr Trp
1               5                   10                  15

Asp Thr Leu Asn His Leu Ile Val Ile Ser Ser Cys Leu Tyr Arg Leu
            20                  25                  30

Asn Leu Lys Ser Ile Ala Gln Ile Ala Leu Ser Val Leu Ala Met Ile
        35                  40                  45

Ile Ser Thr Ser Leu Ile Ile Ala Ala Ile Ile Phe Ile Ile Ser Ala
    50                  55                  60

Asn His Lys Val Thr Leu Thr Thr Val Thr Val Gln Thr Ile Lys Asn
65                  70                  75                  80

His Thr Glu Lys Asn Ile Thr Thr Tyr Leu Thr Gln Val Ser Pro Glu
                85                  90                  95

Arg Val Ser Pro Ser Lys Gln Pro Thr Thr Thr Pro Pro Ile His Thr
            100                 105                 110

Asn Ser Ala Thr Ile Ser Pro Asn Thr Lys Ser Glu Thr His His Thr
        115                 120                 125

Thr Ala Gln Thr Lys Gly Arg Thr Thr Thr Pro Thr Gln Asn Asn Lys
    130                 135                 140

Pro Ser Thr Lys Pro Arg Pro Lys Asn Pro Pro Lys Lys Pro Lys Asp
145                 150                 155                 160

Asp Tyr His Phe Glu Val Phe Asn Phe Val Pro Cys Ser Ile Cys Gly
                165                 170                 175

Asn Asn Gln Leu Cys Lys Ser Ile Cys Lys Thr Ile Pro Ser Asn Lys
            180                 185                 190

Pro Lys Lys Lys Pro Thr Ile Lys Pro Thr Asn Lys Pro Thr Thr Lys
        195                 200                 205

Thr Thr Asn Lys Arg Asp Pro Lys Thr Leu Ala Lys Thr Leu Lys Lys
    210                 215                 220

Glu Thr Thr Thr Asn Pro Thr Lys Lys Pro Thr Pro Lys Thr Thr Glu
225                 230                 235                 240

Arg Asp Thr Ser Thr Ser Gln Ser Thr Val Leu Asp Thr Thr Thr Ser
                245                 250                 255

Lys His Thr Ile Gln Gln Gln Ser Leu His Ser Thr Thr Pro Glu Asn
            260                 265                 270

Thr Pro Asn Ser Thr Gln Thr Pro Thr Ala Ser Glu Pro Ser Thr Ser
        275                 280                 285

Asn Ser Thr
    290
```

<210> SEQ ID NO 9
<211> LENGTH: 840
<212> TYPE: DNA
<213> ORGANISM: Artificial
<220> FEATURE:
<223> OTHER INFORMATION: Synthetic Sequence

<400> SEQUENCE: 9

```
ctggcctacg tggtgcagct gccccctgtac ggcgtgatcg acaccccctg ctggaagctg    60
cacaccagcc ccctgtgcac caccaacacc aaagagggca gcaacatctg cctgacccgg   120
accgaccggg gctggtactg cgataatgcc ggcagcgtgt cattctttcc acaggccgag   180
acatgcaagg tgcagagcaa ccgggtgttc tgcgacacca tgaacagcct gaccctgccc   240
tccgaagtga acctgtgcaa catcgacatc ttcaacccta gtacgactg caagatcatg   300 acctccaaga ccgacgtgtc cagctccgtg atcacctccc tgggcgccat cgtgtcctgc   360
tacggcaaga ccaagtgcac cgccagcaac aagaaccggg gcatcatcaa gaccttcagc   420
aacggctgcg actacgtgtc caacaagggg gtggacaccg tgtccgtggg caacaccctg   480
tactacgtga caaacagga aggcaagagc ctgtacgtga agggcgagcc catcatcaac   540
ttctacgacc ccctggtgtt ccccagcgac gagttcgacg ccagcatcag ccaggtgaac   600
gagaagatca accagagcct ggccttcatc agaaagagcg acgagctgct gcacaatgtg   660
aatgccggca agagcaccac caatatcatg atcaccacaa tcatcatcgt gatcattgtg   720
atcctgctgt ccctgatcgc cgtgggcctg ctgctgtact gcaaggcccg gtccaccccc   780
gtgaccctgt ccaaggacca gctgagcgga atcatcaaca atatcgcctt ctccaactga   840
```

```
<210> SEQ ID NO 10
<211> LENGTH: 592
<212> TYPE: PRT
<213> ORGANISM: Artificial
<220> FEATURE:
<223> OTHER INFORMATION: Synthetic Sequence

<400> SEQUENCE: 10
```

Met Asp Trp Thr Trp Ile Leu Phe Leu Val Ala Ala Thr Arg Val
1               5                   10                  15

His Ser Glu Leu Pro Ile Leu Lys Thr Asn Ala Ile Thr Thr Ile Leu
            20                  25                  30

Ala Ala Val Thr Leu Cys Phe Ala Ser Ser Gln Asn Ile Thr Glu Glu
        35                  40                  45

Phe Tyr Gln Ser Thr Cys Ser Ala Val Ser Lys Gly Tyr Leu Ser Ala
    50                  55                  60

Leu Arg Thr Gly Trp Tyr Thr Ser Val Ile Thr Ile Glu Leu Ser Asn
65                  70                  75                  80

Ile Lys Glu Asn Lys Cys Asn Gly Thr Asp Ala Lys Val Lys Leu Ile
                85                  90                  95

Lys Gln Glu Leu Asp Lys Tyr Lys Asn Ala Val Thr Glu Leu Gln Leu
            100                 105                 110

Leu Met Gln Ser Thr Pro Ala Ala Asn Asn Arg Ala Arg Arg Glu Leu
        115                 120                 125

Pro Arg Phe Met Asn Tyr Thr Leu Asn Asn Thr Lys Asn Thr Asn Val
    130                 135                 140

Thr Leu Ser Lys Lys Arg Lys Arg Arg Phe Leu Gly Phe Leu Leu Gly
145                 150                 155                 160

Val Gly Ser Ala Ile Ala Ser Gly Ile Ala Val Ser Lys Val Leu His
                165                 170                 175

Leu Glu Gly Glu Val Asn Lys Ile Lys Ser Ala Leu Leu Ser Thr Asn
            180                 185                 190

Lys Ala Val Val Ser Leu Ser Asn Gly Val Ser Val Leu Thr Ser Lys
        195                 200                 205

Val Leu Asp Leu Lys Asn Tyr Ile Asp Lys Gln Leu Leu Pro Ile Val
    210                 215                 220

Asn Lys Gln Ser Cys Ser Ile Ser Asn Ile Glu Thr Val Ile Glu Phe
225                 230                 235                 240

Gln Gln Lys Asn Asn Arg Leu Leu Glu Ile Thr Arg Glu Phe Ser Val
            245                 250                 255

Asn Ala Gly Val Thr Thr Pro Val Ser Thr Tyr Met Leu Thr Asn Ser
        260                 265                 270

Glu Leu Leu Ser Leu Ile Asn Asp Met Pro Ile Thr Asn Asp Gln Lys
    275                 280                 285

Lys Leu Met Ser Asn Asn Val Gln Ile Val Arg Gln Gln Ser Tyr Ser
290                 295                 300

Ile Met Ser Ile Ile Lys Glu Glu Val Leu Ala Tyr Val Val Gln Leu
305                 310                 315                 320

Pro Leu Tyr Gly Val Ile Asp Thr Pro Cys Trp Lys Leu His Thr Ser
                325                 330                 335

Pro Leu Cys Thr Thr Asn Thr Lys Glu Gly Ser Asn Ile Cys Leu Thr
            340                 345                 350

Arg Thr Asp Arg Gly Trp Tyr Cys Asp Asn Ala Gly Ser Val Ser Phe
        355                 360                 365

Phe Pro Gln Ala Glu Thr Cys Lys Val Gln Ser Asn Arg Val Phe Cys
370                 375                 380

Asp Thr Met Asn Ser Leu Thr Leu Pro Ser Glu Val Asn Leu Cys Asn
385                 390                 395                 400

Ile Asp Ile Phe Asn Pro Lys Tyr Asp Cys Lys Ile Met Thr Ser Lys
                405                 410                 415

Thr Asp Val Ser Ser Val Ile Thr Ser Leu Gly Ala Ile Val Ser
            420                 425                 430

Cys Tyr Gly Lys Thr Lys Cys Thr Ala Ser Asn Lys Asn Arg Gly Ile
        435                 440                 445

Ile Lys Thr Phe Ser Asn Gly Cys Asp Tyr Val Ser Asn Lys Gly Val
    450                 455                 460

Asp Thr Val Ser Val Gly Asn Thr Leu Tyr Tyr Val Asn Lys Gln Glu
465                 470                 475                 480

Gly Lys Ser Leu Tyr Val Lys Gly Glu Pro Ile Ile Asn Phe Tyr Asp
                485                 490                 495

Pro Leu Val Phe Pro Ser Asp Glu Phe Asp Ala Ser Ile Ser Gln Val
            500                 505                 510

Asn Glu Lys Ile Asn Gln Ser Leu Ala Phe Ile Arg Lys Ser Asp Glu
        515                 520                 525

Leu Leu His Asn Val Asn Ala Gly Lys Ser Thr Thr Asn Ile Met Ile
    530                 535                 540

Thr Thr Ile Ile Ile Val Ile Ile Val Ile Leu Leu Ser Leu Ile Ala
545                 550                 555                 560

Val Gly Leu Leu Leu Tyr Cys Lys Ala Arg Ser Thr Pro Val Thr Leu
                565                 570                 575

Ser Lys Asp Gln Leu Ser Gly Ile Ile Asn Asn Ile Ala Phe Ser Asn
            580                 585                 590

<210> SEQ ID NO 11
<211> LENGTH: 631
<212> TYPE: DNA
<213> ORGANISM: Artificial
<220> FEATURE:
<223> OTHER INFORMATION: Synthetic Sequence

<400> SEQUENCE: 11

```
atggactgga cctggattct gttcctggtg gccgctgcta cccgggtgca cagcagcaga    60
cggaacccct gcaagttcga gatccggggc cactgcctga acggcaagcg gtgccacttc   120
agccacaact acttcgagtg gccccctcac gccctgctgg tgcgccagaa cttcatgctg   180
aacagaatcc tgaagtccat ggacaagagc atcgacaccc tgagcgagat cagcggagcc   240
gccgagctgg accggaccga ggaatatgcc ctgggcgtgg tgggagtgct ggaaagctac   300
atcggcagca tcaacaacat caccaagcag agcgcctgcg tggccatgag caagctgctg   360
accgagctga cagcgacga catcaagaag ctgcgggaca cgaggaaccc aacagcccc    420 aagatccggg tgtacaacac cgtgatcagc tacatcgaga gcaaccggaa gaacaacaag   480
cagaccatcc atctgctgaa gcggctgccc gccgacgtgc tgaagaaaac catcaagaac   540
accctggaca tccacaagtc catcaccatc aacaacccca agaaagcac cgtgtccgac    600 accaacgacc acgccaagaa caacgacacc a                                   631
```

<210> SEQ ID NO 12
<211> LENGTH: 212
<212> TYPE: PRT
<213> ORGANISM: Artificial
<220> FEATURE:
<223> OTHER INFORMATION: Synthetic Sequence

<400> SEQUENCE: 12

```
Met Asp Trp Thr Trp Ile Leu Phe Leu Val Ala Ala Thr Arg Val
1               5                   10                  15

His Ser Ser Arg Arg Asn Pro Cys Lys Phe Glu Ile Arg Gly His Cys
        20                  25                  30

Leu Asn Gly Lys Arg Cys His Phe Ser His Asn Tyr Phe Glu Trp Pro
            35                  40                  45

Pro His Ala Leu Leu Val Arg Gln Asn Phe Met Leu Asn Arg Ile Leu
        50                  55                  60

Lys Ser Met Asp Lys Ser Ile Asp Thr Leu Ser Glu Ile Ser Gly Ala
65                  70                  75                  80

Ala Glu Leu Asp Arg Thr Glu Glu Tyr Ala Leu Gly Val Val Gly Val
                85                  90                  95

Leu Glu Ser Tyr Ile Gly Ser Ile Asn Asn Ile Thr Lys Gln Ser Ala
            100                 105                 110

Cys Val Ala Met Ser Lys Leu Leu Thr Glu Leu Asn Ser Asp Asp Ile
        115                 120                 125

Lys Lys Leu Arg Asp Asn Glu Glu Pro Asn Ser Pro Lys Ile Arg Val
    130                 135                 140

Tyr Asn Thr Val Ile Ser Tyr Ile Glu Ser Asn Arg Lys Asn Asn Lys
145                 150                 155                 160

Gln Thr Ile His Leu Leu Lys Arg Leu Pro Ala Asp Val Leu Lys Lys
                165                 170                 175

Thr Ile Lys Asn Thr Leu Asp Ile His Lys Ser Ile Thr Ile Asn Asn
            180                 185                 190

Pro Lys Glu Ser Thr Val Ser Asp Thr Asn Asp His Ala Lys Asn Asn
        195                 200                 205

Asp Thr Thr Gly
    210
```

<210> SEQ ID NO 13
<211> LENGTH: 948
<212> TYPE: DNA

<213> ORGANISM: Artificial
<220> FEATURE:
<223> OTHER INFORMATION: Synthetic Sequence

<400> SEQUENCE: 13

| | | | | | |
|---|---|---|---|---|---|
| atggactgga | catggatctt | gtttcttgta | gcggcagcaa | cacgcgtcca | ctcctccaag | 60 |
| aataaggatc | agaggaccgc | gaaaacgctt | gagaggacgt | gggacacgct | gaaccacctc | 120 |
| ctgttcatct | cctcgtgtct | ctacaagctc | aaccttaagt | ccatcgcgca | gatcaccttg | 180 |
| agcattctcg | ccatgatcat | ctccaccagc | cttatcattg | ccgcaatcat | cttcatcgca | 240 |
| tccgccaacc | ataaggtgac | attgactaca | gcgattatcc | aagacgctac | tagccagatc | 300 |
| aagaatacca | cgccgaccta | tttgacgcaa | aatcctcagt | tgggaattag | cttctcgaat | 360 |
| ctctcggaaa | ccacgtcgca | gccgactaca | attcttgcgt | caacgactcc | atcggccaaa | 420 |
| tcaacaccac | aatcgactac | cgtaaaaacg | aagaacacga | ctacaacaca | gattcagcct | 480 |
| tcaaagccca | cgaccaaaca | gagacagaat | aagccgccca | acaagcccaa | caatgatttt | 540 |
| cacttcgagg | tgtttaactt | cgtgccctgt | tcgatttgca | gcaataaccc | cacgtgctgg | 600 |
| gcgatttgca | agcgaatccc | gaataagaag | cccgggaaaa | agaccacgac | gaaaccgaca | 660 |
| aagaagccga | caatcaagac | aacgaaaaag | gatcttaaac | ctcagacgac | aaagcctaag | 720 |
| gaagtcttga | caacgaagcc | tacggaaaaa | cccactatca | atactaccaa | gactaacatc | 780 |
| cggacaacac | tgctgacgag | caataccacg | ggaaacccgg | agctcacatc | gcagaaagag | 840 |
| acactccatt | cgacatcctc | cgagggtaac | ccttcgccca | gccaggtgta | tacgacgtca | 900 |
| gaataccctg | ccaacccctc | atcgccctca | aatacgaccc | ggcaatga | | 948 |

<210> SEQ ID NO 14
<211> LENGTH: 315
<212> TYPE: PRT
<213> ORGANISM: Artificial
<220> FEATURE:
<223> OTHER INFORMATION: Synthetic Sequence

<400> SEQUENCE: 14

Met Asp Trp Thr Trp Ile Leu Phe Leu Val Ala Ala Thr Arg Val
1               5                   10                  15

His Ser Ser Lys Asn Lys Asp Gln Arg Thr Ala Lys Thr Leu Glu Arg
            20                  25                  30

Thr Trp Asp Thr Leu Asn His Leu Leu Phe Ile Ser Ser Cys Leu Tyr
        35                  40                  45

Lys Leu Asn Leu Lys Ser Ile Ala Gln Ile Thr Leu Ser Ile Leu Ala
    50                  55                  60

Met Ile Ile Ser Thr Ser Leu Ile Ile Ala Ala Ile Ile Phe Ile Ala
65                  70                  75                  80

Ser Ala Asn His Lys Val Thr Leu Thr Thr Ala Ile Ile Gln Asp Ala
                85                  90                  95

Thr Ser Gln Ile Lys Asn Thr Thr Pro Thr Tyr Leu Thr Gln Asn Pro
            100                 105                 110

Gln Leu Gly Ile Ser Phe Ser Asn Leu Ser Glu Thr Thr Ser Gln Pro
        115                 120                 125

Thr Thr Ile Leu Ala Ser Thr Thr Pro Ser Ala Lys Ser Thr Pro Gln
    130                 135                 140

Ser Thr Thr Val Lys Thr Lys Asn Thr Thr Thr Gln Ile Gln Pro
145                 150                 155                 160

Ser Lys Pro Thr Thr Lys Gln Arg Gln Asn Lys Pro Pro Asn Lys Pro

```
                165                 170                 175
Asn Asn Asp Phe His Phe Glu Val Phe Asn Phe Val Pro Cys Ser Ile
            180                 185                 190

Cys Ser Asn Asn Pro Thr Cys Trp Ala Ile Cys Lys Arg Ile Pro Asn
            195                 200                 205

Lys Lys Pro Gly Lys Lys Thr Thr Lys Pro Thr Lys Lys Pro Thr
            210                 215                 220

Ile Lys Thr Thr Lys Lys Asp Leu Lys Pro Gln Thr Thr Lys Pro Lys
225                 230                 235                 240

Glu Val Leu Thr Thr Lys Pro Thr Glu Lys Pro Thr Ile Asn Thr Thr
                245                 250                 255

Lys Thr Asn Ile Arg Thr Thr Leu Leu Thr Ser Asn Thr Thr Gly Asn
            260                 265                 270

Pro Glu Leu Thr Ser Gln Lys Glu Thr Leu His Ser Thr Ser Ser Glu
            275                 280                 285

Gly Asn Pro Ser Pro Ser Gln Val Tyr Thr Thr Ser Glu Tyr Pro Ser
            290                 295                 300

Gln Pro Ser Ser Pro Ser Asn Thr Thr Arg Gln
305                 310                 315

<210> SEQ ID NO 15
<211> LENGTH: 926
<212> TYPE: DNA
<213> ORGANISM: Artificial
<220> FEATURE:
<223> OTHER INFORMATION: Synthetic Sequence

<400> SEQUENCE: 15
atggattgga cttggatttt gttcttggtg gcagcggcca ctcgcgtcca ttccagcaaa    60
aacaaaaacc aaaggacggc tcggacgctt gagaaaacat gggacacgct taatcacctt   120
attgtgatct catcgtgttt gtaccggttg aatctcaaga gcatcgccca gattgcgctg   180
tcagtcctgg ccatgattat ctcgacatca ctcatcatcg cagccatcat ctttatcatt   240
tcagcgaatc acaaggtaac gcttacaaca gtcacggtgc agaccatcaa gaatcatacc   300
aaaagaatat cacaacctac ctcacccaag tcagcccgga gagagtaagc ccctcaaaac   360
agcctactac gacaccctcc atccacacga actcggcgac catctcaccg aataccaaac   420
agaaacgcat catacgaccg cacagacaaa gggacgaacc actacaccca cacagaacac   480
aaacccagca ccaagccgag gccaaagaat ccgcccaaga agccgaaaga tgactatcac   540
tttgaagtgt tcaacttcgt accgtgttcg atttgcggga ataatcagtt gtgcaaatcc   600
atttgcaaga cgatcccatc caacaaaccg aagaagaaac ctaccatcaa gcccacaaac   660
aagccaacga caaaaacaac gaacaagcgc gatcccaaaa cgctcgcgaa aacgttgaga   720
aggaaacgac gacaaaccct acgaagaaac ccacgcccaa gaccactgag agagacacct   780
ccacctcgca atcgcggta cttgacacga ctacagcaa gcacactatc cagcaacagt   840
ccctgcactc aaccacgccc gagaatacac caaactcaac acagactccg acagcttcag   900
agccttccac ttcgaattcc acatga                                       926

<210> SEQ ID NO 16
<211> LENGTH: 309
<212> TYPE: PRT
<213> ORGANISM: Artificial
<220> FEATURE:
<223> OTHER INFORMATION: Synthetic Sequence
```

```
<400> SEQUENCE: 16

Met Asp Trp Thr Trp Ile Leu Phe Leu Val Ala Ala Ala Thr Arg Val
1               5                   10                  15

His Ser Ser Lys Asn Lys Asn Gln Arg Thr Ala Arg Thr Leu Glu Lys
            20                  25                  30

Thr Trp Asp Thr Leu Asn His Leu Ile Val Ile Ser Cys Leu Tyr
        35                  40                  45

Arg Leu Asn Leu Lys Ser Ile Ala Gln Ile Ala Leu Ser Val Leu Ala
    50                  55                  60

Met Ile Ile Ser Thr Ser Leu Ile Ile Ala Ala Ile Phe Ile Ile
65                  70                  75                  80

Ser Ala Asn His Lys Val Thr Leu Thr Thr Val Thr Val Gln Thr Ile
                85                  90                  95

Lys Asn His Thr Glu Lys Asn Ile Thr Thr Tyr Leu Thr Gln Val Ser
                100                 105                 110

Pro Glu Arg Val Ser Pro Ser Lys Gln Pro Thr Thr Thr Pro Pro Ile
            115                 120                 125

His Thr Asn Ser Ala Thr Ile Ser Pro Asn Thr Lys Ser Glu Thr His
        130                 135                 140

His Thr Thr Ala Gln Thr Lys Gly Arg Thr Thr Thr Pro Thr Gln Asn
145                 150                 155                 160

Asn Lys Pro Ser Thr Lys Pro Arg Pro Lys Asn Pro Pro Lys Lys Pro
                165                 170                 175

Lys Asp Asp Tyr His Phe Glu Val Phe Asn Phe Val Pro Cys Ser Ile
            180                 185                 190

Cys Gly Asn Asn Gln Leu Cys Lys Ser Ile Cys Lys Thr Ile Pro Ser
        195                 200                 205

Asn Lys Pro Lys Lys Pro Thr Ile Lys Pro Thr Asn Lys Pro Thr
    210                 215                 220

Thr Lys Thr Thr Asn Lys Arg Asp Pro Lys Thr Leu Ala Lys Thr Leu
225                 230                 235                 240

Lys Lys Glu Thr Thr Thr Asn Pro Thr Lys Lys Pro Thr Pro Lys Thr
                245                 250                 255

Thr Glu Arg Asp Thr Ser Thr Ser Gln Ser Thr Val Leu Asp Thr Thr
            260                 265                 270

Thr Ser Lys His Thr Ile Gln Gln Gln Ser Leu His Ser Thr Thr Pro
        275                 280                 285

Glu Asn Thr Pro Asn Ser Thr Gln Thr Pro Thr Ala Ser Glu Pro Ser
    290                 295                 300

Thr Ser Asn Ser Thr
305

<210> SEQ ID NO 17
<211> LENGTH: 18
<212> TYPE: PRT
<213> ORGANISM: Human

<400> SEQUENCE: 17

Met Asp Trp Thr Trp Ile Leu Phe Leu Val Ala Ala Ala Thr Arg Val
1               5                   10                  15

His Ser

<210> SEQ ID NO 18
<211> LENGTH: 291
<212> TYPE: DNA
```

<213> ORGANISM: Human

<400> SEQUENCE: 18

```
gcctgcggcg gcaagagact gctgttcctg gccctggcct gggtgctgct ggcccacctg    60
tgttctcagg ccgaggccag caactacgac tgctgcctga gctacatcca gaccccctg   120
cccagcagag ccatcgtggg cttcaccaga cagatggccg acgaggcctg cgacatcaac   180
gccatcatct ccacaccaa gaaacgcaag agcgtgtgcg ccgacccaa gcagaactgg    240
gtcaagagag ccgtgaacct gctgagcctg agagtgaaga aaatgtgatg a            291
```

<210> SEQ ID NO 19
<211> LENGTH: 95
<212> TYPE: PRT
<213> ORGANISM: Human

<400> SEQUENCE: 19

```
Ala Cys Gly Gly Lys Arg Leu Leu Phe Leu Ala Leu Ala Trp Val Leu
 1               5                  10                  15
Leu Ala His Leu Cys Ser Gln Ala Glu Ala Ser Asn Tyr Asp Cys Cys
                20                  25                  30
Leu Ser Tyr Ile Gln Thr Pro Leu Pro Ser Arg Ala Ile Val Gly Phe
            35                  40                  45
Thr Arg Gln Met Ala Asp Glu Ala Cys Asp Ile Asn Ala Ile Ile Phe
        50                  55                  60
His Thr Lys Lys Arg Lys Ser Val Cys Ala Asp Pro Lys Gln Asn Trp
    65                  70                  75                  80
Val Lys Arg Ala Val Asn Leu Leu Ser Leu Arg Val Lys Lys Met
                85                  90                  95
```

<210> SEQ ID NO 20
<211> LENGTH: 345
<212> TYPE: DNA
<213> ORGANISM: Artificial
<220> FEATURE:
<223> OTHER INFORMATION: Synthetic Sequence

<400> SEQUENCE: 20

```
atggactgga cctggattct gttcctggtg gccgctgcta caagagtgca ctctgcctgc    60
ggcggcaaga gactgctgtt cctggccctg gcctgggtgc tgctggccca cctgtgttct   120
caggccgagg ccagcaacta cgactgctgc ctgagctaca tccagacccc cctgcccagc   180
agagccatcg tgggcttcac cagacagatg gccgacgagg cctgcgacat caacgccatc   240
atcttccaca ccaagaaacg caagagcgtg tgcgccgacc ccaagcagaa ctgggtcaag   300
agagccgtga acctgctgag cctgagagtg aagaaaatgt gatga                   345
```

<210> SEQ ID NO 21
<211> LENGTH: 113
<212> TYPE: PRT
<213> ORGANISM: Artificial
<220> FEATURE:
<223> OTHER INFORMATION: Synthetic Sequence

<400> SEQUENCE: 21

```
Met Asp Trp Thr Trp Ile Leu Phe Leu Val Ala Ala Thr Arg Val
 1               5                  10                  15
His Ser Ala Cys Gly Gly Lys Arg Leu Leu Phe Leu Ala Leu Ala Trp
                20                  25                  30
Val Leu Leu Ala His Leu Cys Ser Gln Ala Glu Ala Ser Asn Tyr Asp
```

```
            35                  40                  45
Cys Cys Leu Ser Tyr Ile Gln Thr Pro Leu Pro Ser Arg Ala Ile Val
     50                  55                  60
Gly Phe Thr Arg Gln Met Ala Asp Glu Ala Cys Asp Ile Asn Ala Ile
 65                  70                  75                  80
Ile Phe His Thr Lys Lys Arg Lys Ser Val Cys Ala Asp Pro Lys Gln
                 85                  90                  95
Asn Trp Val Lys Arg Ala Val Asn Leu Leu Ser Leu Arg Val Lys Lys
                100                 105                 110
Met
```

```
<210> SEQ ID NO 22
<211> LENGTH: 9
<212> TYPE: PRT
<213> ORGANISM: Respiratory Syncytial Virus

<400> SEQUENCE: 22

Lys Tyr Lys Asn Ala Val Thr Glu Leu
 1               5
```

```
<210> SEQ ID NO 23
<211> LENGTH: 18
<212> TYPE: PRT
<213> ORGANISM: Respiratory Syncytial Virus

<400> SEQUENCE: 23

Ile Glu Thr Val Ile Glu Phe Gln Gln Lys Asn Asn Arg Leu Leu Glu
 1               5                  10                  15
Ile Thr
```

```
<210> SEQ ID NO 24
<211> LENGTH: 9
<212> TYPE: PRT
<213> ORGANISM: Respiratory Syncytial Virus

<400> SEQUENCE: 24

Tyr Met Leu Thr Asn Ser Glu Leu Leu
 1               5
```

```
<210> SEQ ID NO 25
<211> LENGTH: 70
<212> TYPE: PRT
<213> ORGANISM: Respiratory Syncytial Virus

<400> SEQUENCE: 25

Ser Val Gly Asn Thr Leu Tyr Tyr Val Asn Lys Gln Glu Gly Lys Ser
 1               5                  10                  15
Leu Tyr Val Lys Gly Glu Pro Ile Ile Asn Phe Tyr Asp Pro Leu Val
                20                  25                  30
Phe Pro Ser Asp Glu Phe Asp Ala Ser Ile Ser Gln Val Asn Glu Lys
                35                  40                  45
Ile Asn Gln Ser Leu Ala Phe Ile Arg Lys Ser Asp Glu Leu Leu His
     50                  55                  60
Asn Val Asn Ala Gly Lys
 65                  70
```

```
<210> SEQ ID NO 26
<211> LENGTH: 5
<212> TYPE: PRT
<213> ORGANISM: Respiratory Syncytial Virus
```

```
<400> SEQUENCE: 26

Arg Ala Arg Arg Glu
1               5

<210> SEQ ID NO 27
<211> LENGTH: 7
<212> TYPE: PRT
<213> ORGANISM: Respiratory Syncytial Virus

<400> SEQUENCE: 27

Lys Lys Arg Lys Arg Arg Phe
1               5

<210> SEQ ID NO 28
<211> LENGTH: 15
<212> TYPE: PRT
<213> ORGANISM: Respiratory Syncytial Virus

<400> SEQUENCE: 28

Leu Leu Gly Val Gly Ser Ala Ile Ala Ser Gly Ile Ala Val Ser
1               5                   10                  15

<210> SEQ ID NO 29
<211> LENGTH: 42
<212> TYPE: PRT
<213> ORGANISM: Respiratory Syncytial Virus

<400> SEQUENCE: 29

Ser Leu Ile Asn Asp Met Pro Ile Thr Asn Asp Gln Lys Lys Leu Met
1               5                   10                  15

Ser Asn Asn Val Gln Ile Val Arg Gln Gln Ser Tyr Ser Ile Met Ser
                20                  25                  30

Ile Ile Lys Glu Glu Val Leu Ala Tyr Val
                35                  40

<210> SEQ ID NO 30
<211> LENGTH: 9
<212> TYPE: PRT
<213> ORGANISM: Respiratory Syncytial Virus

<400> SEQUENCE: 30

Ser Tyr Ile Gly Ser Ile Asn Asn Ile
1               5

<210> SEQ ID NO 31
<211> LENGTH: 9
<212> TYPE: PRT
<213> ORGANISM: Respiratory Syncytial Virus

<400> SEQUENCE: 31

Asn Tyr Phe Glu Trp Pro Pro His Ala
1               5
```